US012385028B2

(12) United States Patent
Sohn et al.

(10) Patent No.: US 12,385,028 B2
(45) Date of Patent: Aug. 12, 2025

(54) NON-TOXIC PROTEASE HAVING IMPROVED PRODUCTIVITY

(71) Applicant: NC BIT INC., Gyeonggi-do (KR)

(72) Inventors: Young Doug Sohn, Gyeonggi-do (KR); Ho-Jun Kim, Seoul (KR); Ui Jung Kwon, Gyeonggi-do (KR); Jong-Tak Kim, Seoul (KR); Kyoung Soo Kim, Gyeonggi-do (KR)

(73) Assignee: NC BIT INC., Gyeonggi-Do (KR)

( * ) Notice: Subject to any disclaimer, the term of this patent is extended or adjusted under 35 U.S.C. 154(b) by 826 days.

(21) Appl. No.: 17/617,290

(22) PCT Filed: Apr. 28, 2020

(86) PCT No.: PCT/KR2020/005623
§ 371 (c)(1),
(2) Date: Dec. 7, 2021

(87) PCT Pub. No.: WO2020/251163
PCT Pub. Date: Dec. 17, 2020

(65) Prior Publication Data

US 2022/0251531 A1 Aug. 11, 2022

(30) Foreign Application Priority Data

Jun. 12, 2019 (KR) ........................ 10-2019-0069259

(51) Int. Cl.
*C12N 9/52* (2006.01)
*A61P 21/00* (2006.01)

(52) U.S. Cl.
CPC ................ *C12N 9/52* (2013.01); *A61P 21/00* (2018.01)

(58) Field of Classification Search
CPC .................................. C12N 9/52; A61P 21/00
See application file for complete search history.

(56) References Cited

U.S. PATENT DOCUMENTS

| | | | |
|---|---|---|---|
| 2006/0258847 A1 | 11/2006 | Johnson et al. |
| 2012/0128649 A1 | 5/2012 | Chaddock et al. |

FOREIGN PATENT DOCUMENTS

| | | | |
|---|---|---|---|
| EP | 2524963 A1 | 11/2012 |
| KR | 1019940701061 A | 4/1994 |
| KR | 1020100088683 A | 8/2010 |

(Continued)

OTHER PUBLICATIONS

Cabrita, L.D., et al., "Protein expression and refolding—a practical guide to getting the most out of inclusion bodies", Biotechnology Annual Review, 2004, pp. 31-50; DOI:10.1016/S1387-2656(04)10002-1, vol. 10, Publisher: Elsevier.

(Continued)

*Primary Examiner* — David W Berke-Schlessel
*Assistant Examiner* — Trent R Clarke
(74) *Attorney, Agent, or Firm* — HULTQUIST, PLLC; Steven J. Hultquist

(57) ABSTRACT

The present invention relates to a mutated non-toxic protease in which the amino acid cysteine (Cys) at position 430 of a non-toxic protease represented by the amino acid sequence of SEQ ID NO: 1 is substituted with an amino acid other than cysteine. According to the present invention, it is possible to recover a refolded non-toxic protease from an insoluble fraction from which the non-toxic protease was almost impossible to recover in the prior art, and thus it is possible to produce the non-toxic protease with significantly improved productivity.

19 Claims, 21 Drawing Sheets

Specification includes a Sequence Listing.

(56) References Cited

FOREIGN PATENT DOCUMENTS

| | | | |
|---|---|---|---|
| KR | 1020120034927 | A | 4/2012 |
| KR | 2020120034927 | A | 4/2012 |
| KR | 1020140036239 | A | 3/2014 |
| KR | 101636846 | B1 | 6/2016 |

OTHER PUBLICATIONS

Clark, E. De B., "Refolding of recombinant proteins", Current Opinion in Biotechnology, 1998, pp. 157-163, vol. 9, Publisher: Current Biology.
Dhaked, R.K., et al., Indian J Med Res, 2010, pp. 489-503, vol. 132.
Fonfria, E., et al., "Engineering Botulinum Toxins to Improve and Expand Targeting and Snare Cleavage Activity", Toxins, 2018, pp. 278; doi:.3390/toxins10070278, vol. 10, No. 7, Publisher: www.mdpi.com/journal/toxins.
Masuyer, G., et al., "Engineered Botulinum Neurotoxins as New Therapeutics", Annual Review of Pharmacology and Toxicology, 2013, pp. 27-51, vol. 53, No. 3.
Mauskop, A., "The Use of Botulinum Toxin in the Treatment of Headaches", Current Pain and Headache Reports, 2002, pp. 320-323, vol. 6, Publisher: Current Science Inc.
Mauskop, A., "Botulinum toxin in headache treatment: the end of the road?", Cephalgia, , pp. 769-771, vol. 26, Publisher: Blackwell Publishing Ltd.
Saffarian, P., et al., "Expression and purification of recombinant TAT-BoNT/A (1-448) under denaturing and native conditions", Bioengineered, 2016, pp. 478-483, vol. 7, No. 6.
Turton, K. et al., "Botulinum and tetanus neurotoxins: structure, function and therapeutic utility", Trends in Biochemical Sciences, 2002, pp. 552-558, vol. 27, No. 11.
Verheyden, J., et al., "Other Noncosmetic Uses of Botox", Dis Mon, 2002, pp. 357-366; doi:10.1053/mda.2002.25136, vol. 48.
Yamaguchi, H., et al., "Refolding Techniques for Recovering Biologically Active Recombinant Proteins from Inclusion Bodies", biomolecules, 2014, pp. 235-251; doi:10.3390/biom4010235, vol. 4, Publisher: www.mdpi.com/journal/biomolecules/.
Avcil, M., et al., "Efficacy of bioactive peptides loaded on hyaluronic acid microneedle patches: A monocentric clinical study", J Cosmet Dermotol, 2019, DOI:10.1111/jocd.13009, Publisher: Wiley.
Issue of PESR in European Patent Application No. 23154792.8 on Jun. 7, 2023.

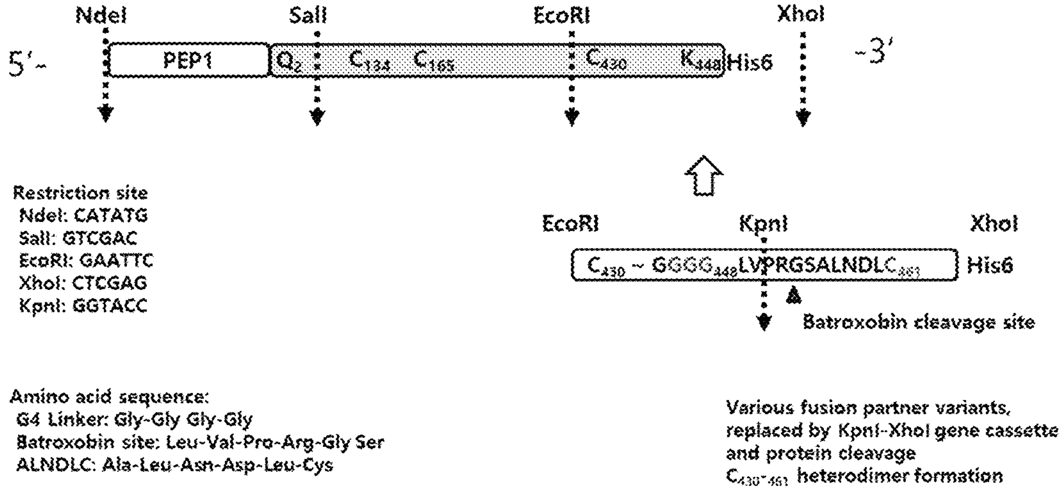

FIG. 5

Restriction site
Ndel: CATATG
Sall: GTCGAC
EcoRI: GAATTC
Xhol: CTCGAG
KpnI: GGTACC Amino acid sequence:
G4 Linker: Gly-Gly Gly-Gly
Batroxobin site: Leu-Val-Pro-Arg-Gly Ser
ALNDLC: Ala-Leu-Asn-Asp-Leu-Cys Various fusion partner variants, replaced by KpnI-XhoI gene cassette and protein cleavage
$C_{430-461}$ heterodimer formation

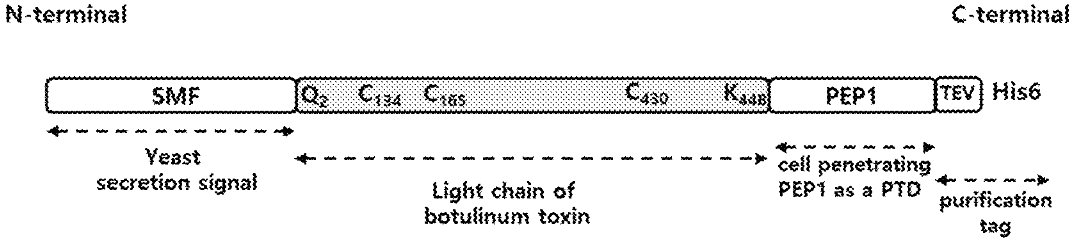

FIG. 6

N-terminal — SMF | $Q_2$ $C_{134}$ $C_{165}$ $C_{430}$ $K_{448}$ | PEP1 | TEV | His6 — C-terminal

- Yeast secretion signal
- Light chain of botulinum toxin
- cell penetrating PEP1 as a PTD
- purification tag 1. pET22b-BTX-LC wild non-expression control
2. pET22b-BTX-LC wild expression
3. pET22b-BTXL-TSI 430G non-expression control
4. pET22b-BTXL-TSI 430G expression
5. pET22b-BTXL-TSI 430A non-expression control
6. pET22b-BTXL-TSI 430A expression
7. pET22b-BTXL-TSI 430S non-expression control
8. pET22b-BTXL-TSI 430S expression S: Standard Marker for Molecular Weight 1. pET22b-BTX LC-his7 total lysate 10ul
2. pET22b-BTX LC-his7 supernatant 10ul
3. pET22b-BTX LC-his7 pellet 10ul 1. pET22b-BTX LC-his7 total lysate
2. pET22b-BTX LC-his7 supernatant
3. pET22b-BTX LC-his7 pellet

FIG. 10

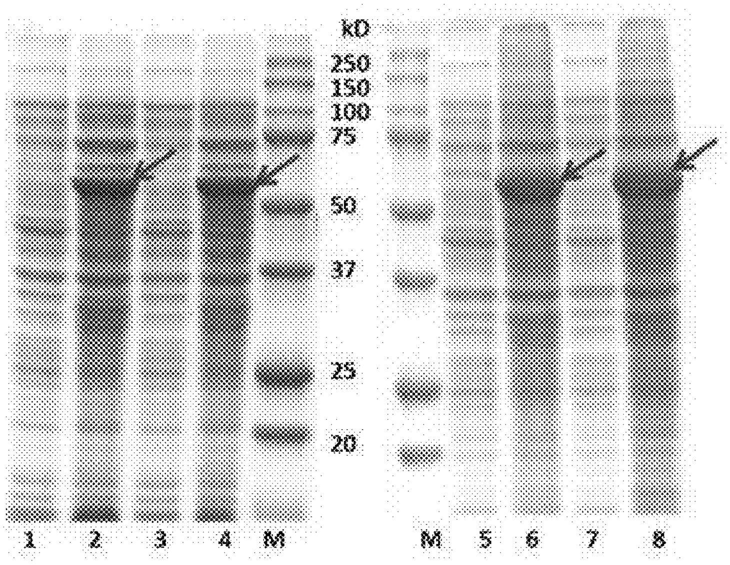

1. pET22b-BTX-LC wild opti-codon non-expression control
2. pET22b-BTX-LC wild opti-codon expression
3. pET22b-BTX-TSI wild opti-codon 430G non-expression control
4. pET22b-BTX-TSI wild opti-codon 430G expression
5. pET22b-BTX-TSI wild opti-codon 430A non-expression control
6. pET22b-BTX-TSI wild opti-codon 430A expression
7. pET22b-BTX-TSI wild opti-codon 430S non-expression control
8. pET22b-BTX-TSI wild opti-codon 430S expression M: Molecular weight standard marker

FIG. 11

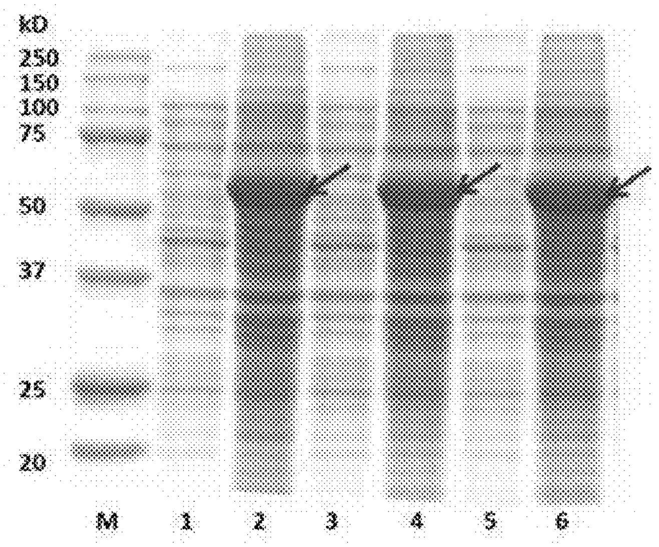

1. pET22b-BTXL-TSI wild opti-codon 430G-BFGFRP non-expression control
2. pET22b-BTXL-TSI wild opti-codon 430G-BFGFRP expression
3. pET22b-BTXL-TSI wild opti-codon 430A-BFGFRP non-expression control
4. pET22b-BTXL-TSI wild opti-codon 430A-BFGFRP expression
5. pET22b-BTXL-TSI wild opti-codon 430S-BFGFRP non-expression control
6. pET22b-BTXL-TSI wild opti-codon 430S-BFGFRP expression M: Molecular weight standard marker

FIG. 14

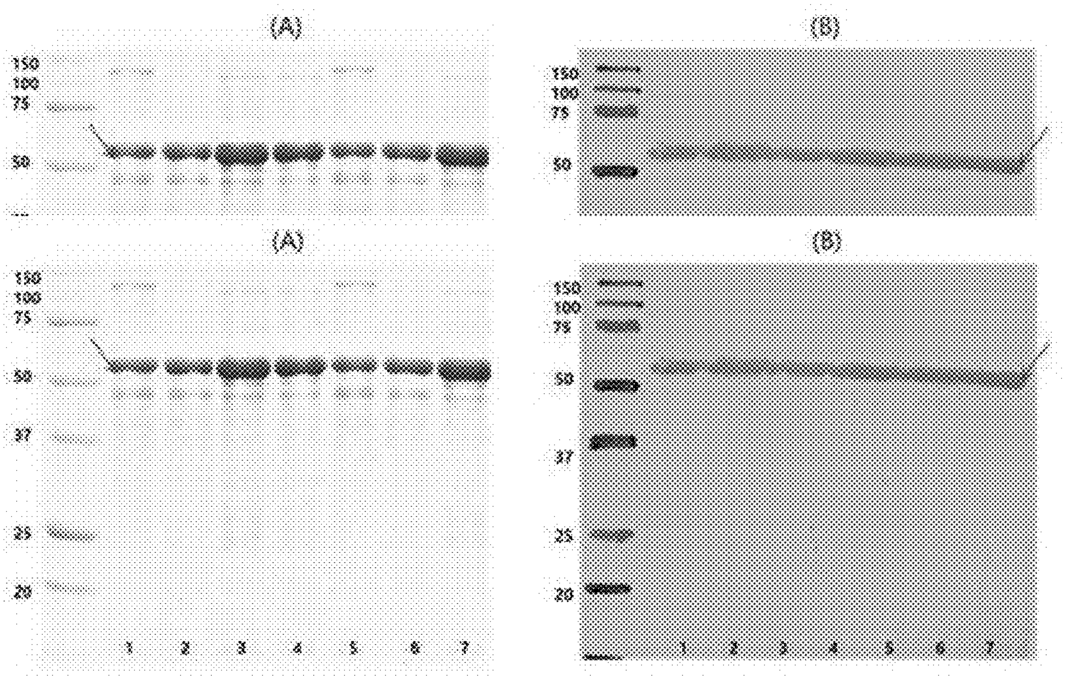

1. Cell-penetrating wild-type BTXL-TSI His-tag purification
2. BTXL-TSI G430A variants His-tag purification
3. BTXL-TSI G430G variants His-tag purification
4. BTXL-TSI G430S variants His-tag purification
5. BTXL-TSI G430A-BEGFRP variants His-tag purification
6. BTXL-TSI G430G-BEGFRP variants His-tag purification
7. BTXL-TSI G430S-BEGFRP variants His-tag purification 1. Cell-penetrating wild-type BTXL-TSI His-tag purification
2. BTXL-TSI G430A variants His-tag purification
3. BTXL-TSI G430G variants His-tag purification
4. BTXL-TSI G430S variants His-tag purification
5. BTXL-TSI G430A-BEGFRP variants His-tag purification
6. BTXL-TSI G430G-BEGFRP variants His-tag purification
7. BTXL-TSI G430S-BEGFRP variants His-tag purification FIG. 16
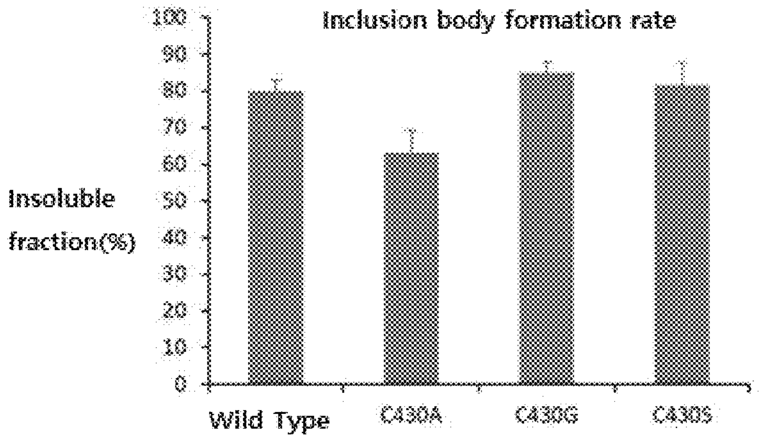
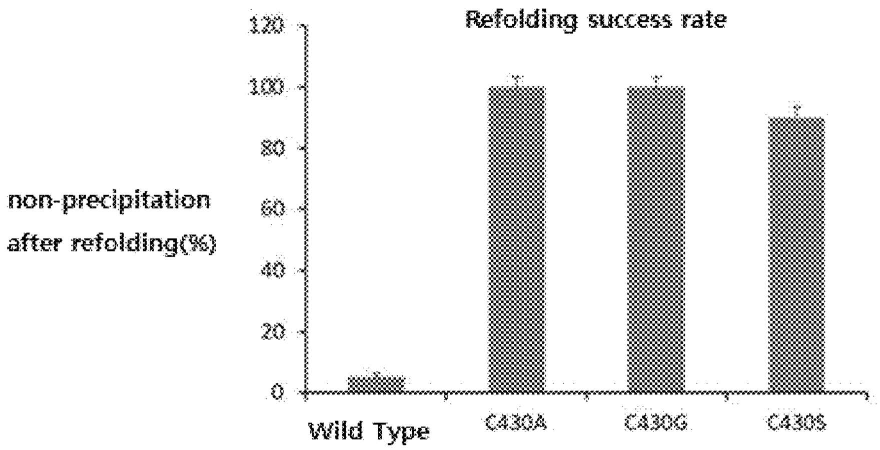

1. pET22b-SNAP25-Annexin V non-expression control
2. pET22b-SNAP25-Annexin V expression
3. purificated SNAP25-Annexin V protein M: Molecular weight standard marker

FIG. 18

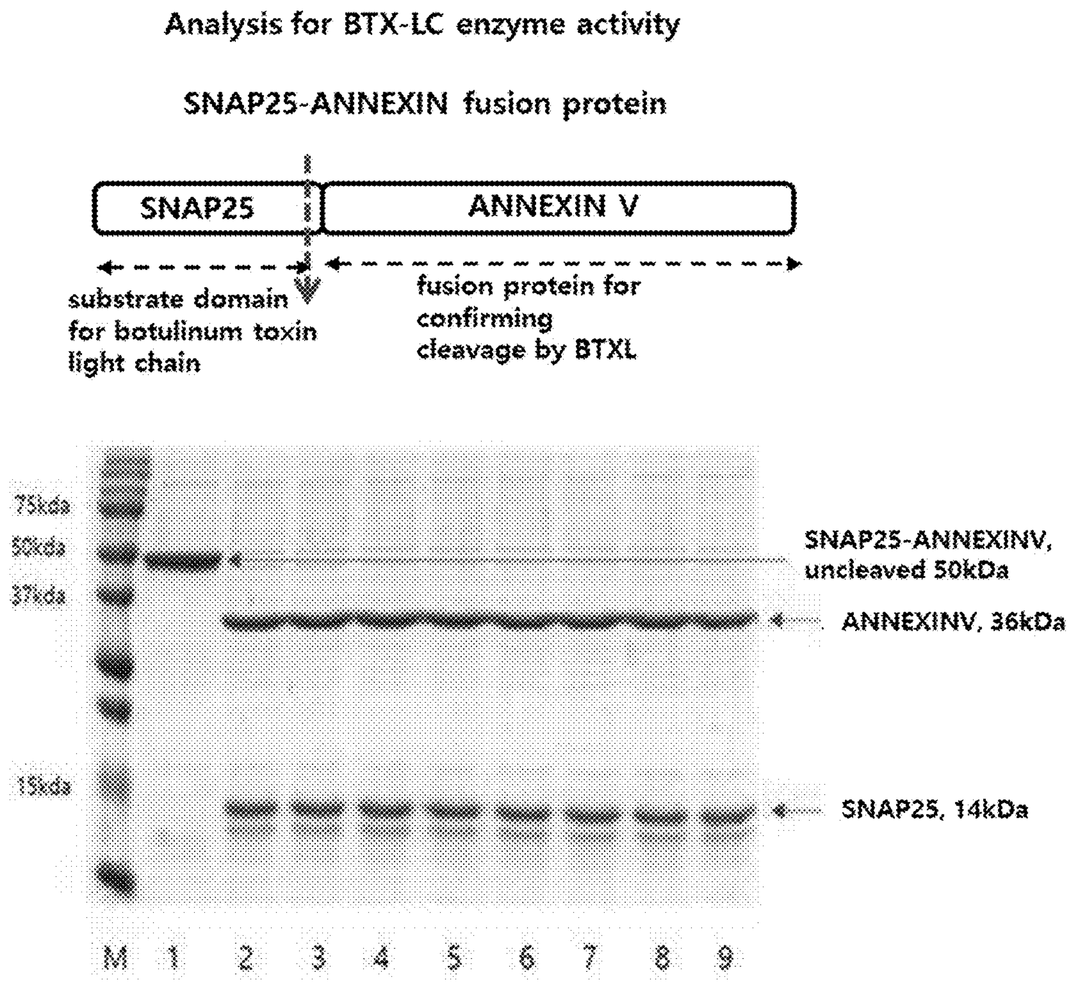

M. Molecular weight standard
1. SNAP25-ANNEXINV uncleaved control
2. SNAP25-ANNEXINV cleaving reaction: BTXL-natural form Light Chain
3. SNAP25-ANNEXINV cleaving reaction: BTXL-C430G variant
4. SNAP25-ANNEXINV cleaving reaction: BTXL-C430A variant
5. SNAP25-ANNEXINV cleaving reaction: BTXL-C430S variant
6. SNAP25-ANNEXINV cleaving reaction: BTXL-Belt variant
7. SNAP25-ANNEXINV cleaving reaction: BTXL-C430G-BFGFRP variant
8. SNAP25-ANNEXINV cleaving reaction: BTXL-C430A-BFGFRP variant
9. SNAP25-ANNEXINV cleaving reaction: BTXL-Belt-BFGFRP variant

FIG. 21

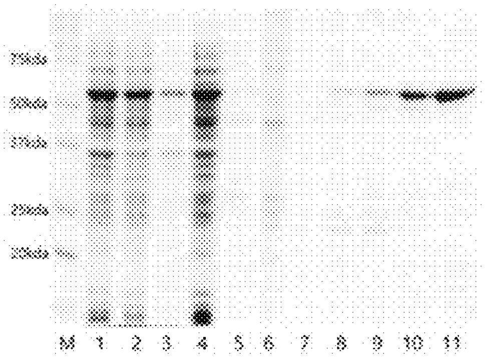

1. Wild type total lysate
2. Wild type soluble fraction
3. Wild type insoluble fraction
4. Wild type Ni-IDA purification flow through fraction
5. Wild type Ni-IDA purification first washed fraction
6. Wild type Ni-IDA purification second washed fraction
7. Wild type Ni-IDA purification elution fraction(100mM imidazole)
8. Wild type Ni-IDA purification elution fraction(200mM imidazole)
9. Wild type Ni-IDA purification elution fraction(300mM imidazole)
10. Wild type Ni-IDA purification elution fraction(500mM imidazole)
11. Wild type Ni-IDA purification elution fraction(700mM imidazole)

FIG. 22

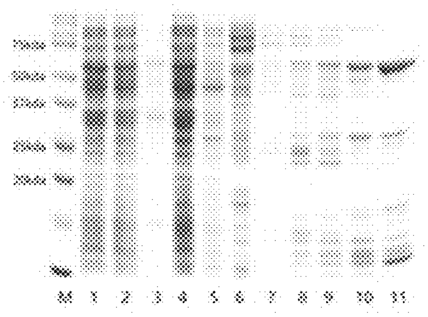

1. C430S total lysate
2. C430S soluble fraction
3. C430S insoluble fraction
4. C430S Ni-IDA purification flow through fraction
5. C430S Ni-IDA purification first washed fraction
6. C430S Ni-IDA purification second washed fraction
7. C430S Ni-IDA purification elurion fraction(100mM imidazole)
8. C430S Ni-IDA purification elurion fraction(200mM imidazole)
9. C430S Ni-IDA purification elurion fraction(300mM imidazole)
10. C430S Ni-IDA purification elurion fraction(500mM imidazole)
11. C430S Ni-IDA purification elurion fraction(700mM imidazole)

FIG. 23

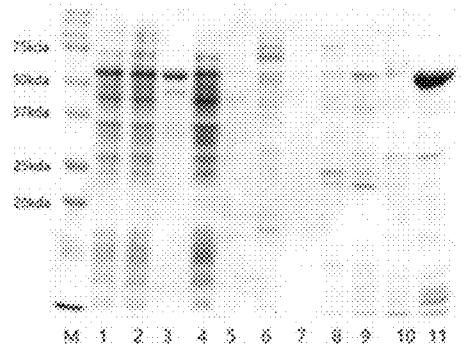

1. C430A total lysate
2. C430A soluble fraction
3. C430A insoluble fraction
4. C430A Ni-IDA purification flow through fraction
5. C430A Ni-IDA purification first washed fraction
6. C430A Ni-IDA purification second washed fraction
7. C430A Ni-IDA purification elurion fraction(100mM imidazole)
8. C430A Ni-IDA purification elurion fraction(200mM imidazole)
9. C430A Ni-IDA purification elurion fraction(300mM imidazole)
10. C430A Ni-IDA purification elurion fraction(500mM imidazole)
11. C430A Ni-IDA purification elurion fraction(700mM imidazole)

FIG. 24

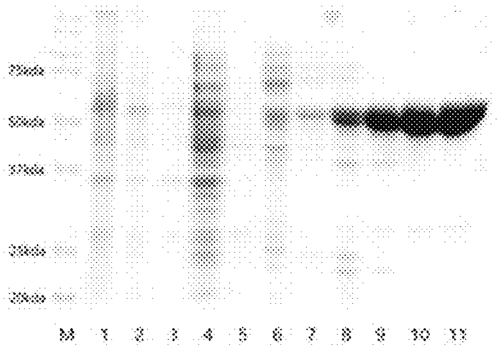

1. C430G total lysate
2. C430G soluble fraction
3. C430G insoluble fraction
4. C430G Ni-IDA purification flow through fraction
5. C430G Ni-IDA purification first washed fraction
6. C430G Ni-IDA purification second washed fraction
7. C430G Ni-IDA purification elurion fraction(100mM imidazole)
8. C430G Ni-IDA purification elurion fraction(200mM imidazole)
9. C430G Ni-IDA purification elurion fraction(300mM imidazole)
10. C430G Ni-IDA purification elurion fraction(500mM imidazole)
11. C430G Ni-IDA purification elurion fraction(700mM imidazole)

FIG. 25

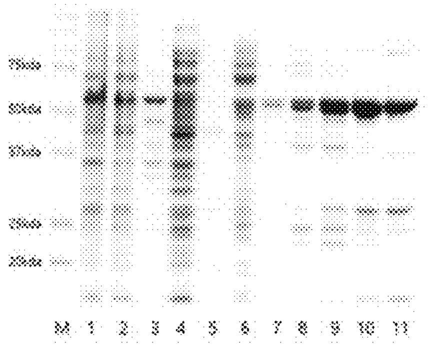

1. C430G-BFGFRP total lysate
2. C430G-BFGFRP soluble fraction
3. C430G-BFGFRP insoluble fraction
4. C430G-BFGFRP Ni-IDA purification flow through fraction
5. C430G-BFGFRP Ni-IDA purification first washed fraction
6. C430G-BFGFRP Ni-IDA purification second washed fraction
7. C430G-BFGFRP Ni-IDA purification elurion fraction(100mM imidazole)
8. C430G-BFGFRP Ni-IDA purification elurion fraction(200mM imidazole)
9. C430G-BFGFRP Ni-IDA purification elurion fraction(300mM imidazole)
10. C430G-BFGFRP Ni-IDA purification elurion fraction(500mM imidazole)
11. C430G-BFGFRP Ni-IDA purification elurion fraction(700mM imidazole)

FIG. 26

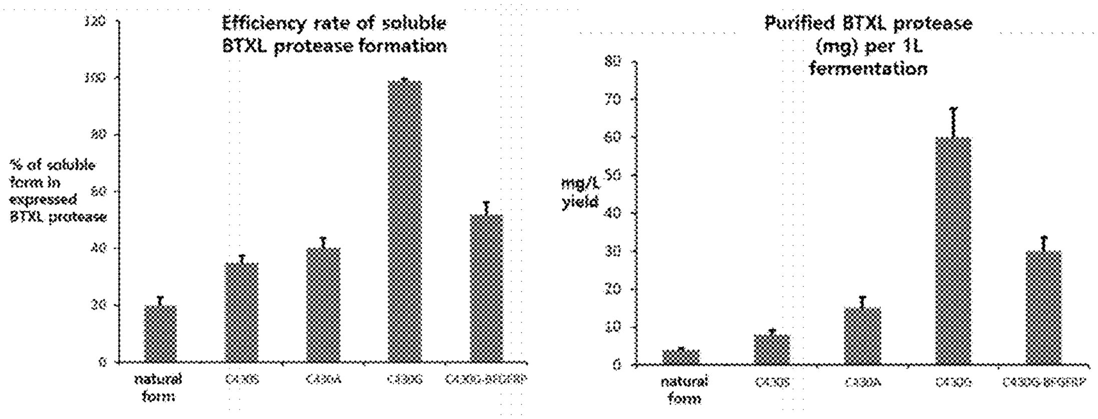

NON-TOXIC PROTEASE HAVING IMPROVED PRODUCTIVITY

CROSS-REFERENCE TO RELATED APPLICATIONS

This application is a United States national phase under 35 USC § 371 of International Patent Application No. PCT/KR2020/005623 filed Apr. 28, 2020, which in turn claims priority under 35 USC § 119 of Korean Patent Application No. 10-2019-0069259 filed Jun. 12, 2019. The disclosures of all such applications are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "607_SeqListing_ST25.txt" created on Dec. 7, 2021 and is 96,478 bytes in size. The sequence listing contained in this .txt file is part of the specification and is hereby incorporated by reference herein in its entirety.

TECHNICAL FIELD

The present invention relates to a non-toxic protease with improved productivity, and more particularly, to a non-toxic protease which is produced with improved productivity as a result of inhibiting irreversible protein aggregation and improving refolding efficiency through introduction of a point mutation.

BACKGROUND ART

Some of the best known examples of substances that act on nerve cells by incapacitating the secretory function of cellular physiological substances in target cells include clostridial neurotoxins (e.g., botulinum neurotoxins commercially available under trade names such as Dysport™, Neurobloc™, and Botox™). The non-toxic protease domains constituting these substances are zinc-endopeptidases which are a well-known group of proteases that act on target cells by incapacitating the secretory function of cellular physiological substances. Interestingly, the non-toxic protease domains alone do not kill the target cells on which they act.

The non-toxic protease domains act by proteolytically cleaving SNARE proteins (e.g., intracellular transport proteins known as SNAP-25, VAMP, or syntaxin) (see Gerald K (2002) "Cell and Molecular Biology" (4th edition) John Wiley & Sons, Inc.). The acronym "SNARE" derives from Soluble NSF Attachment Receptor, where NSF means N-ethylmaleimide—Sensitive Factor. SNARE proteins are integral to intracellular vesicle formation, and thus to secretion of molecules through vesicle transport from a cell. Accordingly, once delivered to a desired target cell, the non-toxic protease is capable of inhibiting cellular secretion from the target cell.

Clostridial neurotoxins represent a major group of non-toxic toxin molecules and comprise two polypeptide chains joined together by a disulfide bond. The two chains are termed the heavy chain (H-chain) having a molecular weight of about 100 kDa and the light chain (L-chain) having a molecular weight of about 50 kDa. It is the L-chain, which possesses a protease function and exhibits a high substrate specificity for vesicle and/or plasma membrane associated (SNARE) proteins involved in the exocytic process (e.g., synaptobrevin, syntaxin or SNAP-25). These substrates are important components of the neurosecretory machinery (Korean Patent Application Publication No. 10-2014-0036239).

Non-toxic proteases can temporarily inhibit muscle contraction in vivo, and thus they are used as bio-drugs for the treatment of some Dystonia or muscle contraction disorders. That is, non-toxic proteases inhibit muscle contraction by temporarily inhibiting the release of acetylcholine. Recently, non-toxic proteases have been successfully used as injectable biological drugs in the treatment of various muscle contraction disorders, such as blepharospasm, migraine headache, reduction of facial wrinkles, etc. (Mauskop A. The use of Botulinum Toxin in the treatment of headaches. Curr Pain Headache Rep 2002; 6:320-3; Mauskop A. Botulinum toxin in headache treatment: The end of the road? Cephalalgia 2007; 27:468; Verheyden J, Blitzer A. Other noncosmetic uses of Botox. Dis Mon 2002; 48:357-66; Dhaked R K, Singh M K, Singh P, Gupta P. Botulinum toxin: Bioweapon & magic drug. Indian J Med Res 2010; 132: 489-503; Turton K, Chaddock J A, Acharya K R. Botulinum and tetanus neurotoxins: structure, function and therapeutic utility. Trends Biochem Sci 2002; 27:552-8; Masuyer G, Chaddock J A, Foster K A, Acharya K R. Engineered botulinum neurotoxins as new therapeutics. Annu Rev Pharmacol Toxicol 2014; 54:27-51).

Non-toxic proteases can be used for various purposes as described above and have high commercial potential, and thus attempts have been made to mass-produce non-toxic proteases using recombinant microorganisms. However, a significant portion of a recombinant non-toxic protease expressed in a recombinant microorganism transformed with a recombinant expression vector tends to aggregate in the form of inclusion bodies in an insoluble fraction depending on the composition and structure of the protein. In this case, the protein is dissolved as much as possible in a solution of urea, guanidium chloride, a surfactant or a reducing agent, and then purified through centrifugation, dialysis, ion exchange, hydrophobic interaction, reverse phase and gel filtration HPLC, various chromatography columns packed with an appropriate type of resin, etc. The solution used in this complex purification process changes the structure of the protein, resulting in loss of the activity of the non-toxic protease, and even when a complex additional process of refolding the purified protein to restore the protease activity is introduced, a problem arises in that a problem that most of the inclusion bodies are not recovered due to low restoration efficiency (Saffarian, BIOENGINEERED 2016, VOL. 7, NO. 6, 478-483). This refolding process is generally performed by diluting or dialyzing the protein in a buffer solution free of a reducing/denaturing agent depending on the size of the protein to induce disulfide bonds between cysteine amino acids inside the protein through oxidation, and then separating soluble and insoluble fractions by filtration or centrifugation, thereby recovering only a protein whose unique three-dimensional structure has been restored. Even when this complicated process is performed, the recovery rate of the refolded non-toxic protease from the insoluble fraction is quite low (Cabrita, 2004, Biotechnology Annual Review, 10:31-50; Clark, Current Opinion in Biotechnology 1998, 9:157-163; Yamaguchi, Biomolecules 2014, 4, 235-251).

Accordingly, the present inventors have made extensive efforts to effectively recover a refolded non-toxic protease even from insoluble fractions in which most of non-toxic proteases are present but which are almost impossible to recover due to their irreversible aggregation into inclusion bodies, in a process of producing a non-toxic protease using a recombinant microorganism. As a result, the present inventors have found that, when a point mutation is induced in some amino acids of a non-toxic protease, it is possible to recover a non-toxic protease that reversibly aggregates into inclusion bodies, is effectively refolded even in insoluble fractions, and has activity, and the production of the non-toxic protease may be maximized, thereby completing the present invention.

SUMMARY OF THE INVENTION

An object of the present invention is to provide a mutated non-toxic protease which is produced in improved yield using a recombinant microorganism, and a method for producing the same.

To achieve the above object, the present invention provides a mutated non-toxic protease in which the amino acid cysteine at position 430 of a non-toxic protease represented by the amino acid sequence of SEQ ID NO: 1 is substituted with an amino acid other than cysteine.

The present invention also provides a fusion non-toxic proteinase in which the mutated non-toxic protease is fused to any one or more peptides selected from the group consisting of:

i) a cell penetrating peptide;
ii) a belt domain fragment peptide; and
iii) a cell targeting peptide.

The present invention also provides a fusion non-toxic proteinase in which the mutated non-toxic protease is fused with any one or more peptides selected from the group consisting of:

i) a yeast secretion signal peptide;
ii) a cell penetrating peptide; and
ii) a cell targeting peptide.

The present invention also provides a mutant gene encoding the mutated non-toxic protease.

The present invention also provides a gene construct comprising: the mutant gene; and any one or more nucleic acids selected from the group consisting of i) a nucleic acid encoding a cell penetrating peptide;
ii) a nucleic acid encoding a belt domain fragment peptide; and
iii) a nucleic acid encoding a cell targeting peptide.

The present invention also provides a gene construct comprising: the mutant gene; and any one or more nucleic acids selected from the group consisting of i) a nucleic acid encoding a yeast secretion signal peptide;
ii) a nucleic acid encoding a cell penetrating peptide; and
iii) a nucleic acid encoding a cell targeting peptide.

The present invention also provides a recombinant vector into which the mutant gene has been introduced.

The present invention also provides a recombinant microorganism into which the recombinant vector has been introduced.

The present invention also provides a method for producing a mutated non-toxic protease or a fusion non-toxic protease, the method comprising steps of:

(a) producing the mutated non-toxic protease or the fusion non-toxic protease by culturing the recombinant microorganism;
(b) disrupting the recombinant microorganism; and
(c) purifying the mutated non-toxic protease or the fusion non-toxic protease from the disrupted recombinant microorganism.

The present invention also provides a pharmaceutical composition for treating Dystonia containing the mutated or fusion non-toxic protease as an active ingredient.

The present invention also provides a hyaluronic acid microneedle patch containing the mutated or fusion non-toxic protease.

The present invention also provides a method for alleviating or treating symptoms of Dystonia, the method comprising a step of administering the mutated or fusion non-toxic protease to a subject in need of alleviation or treatment of symptoms of Dystonia.

The present invention also provides the use of the mutated or fusion non-toxic protease for the manufacture of a medicament for use in the alleviation or treatment of symptoms of Dystonia.

The present invention also provides the above mutated or fusion non-toxic protease for use in a method for alleviating or treating symptoms of Dystonia.

BRIEF DESCRIPTION OF DRAWINGS

FIG. 5 schematically shows the structure of a fusion non-cytotoxic protease into which $(Gly)_4$ capable of imparting structural flexibility to a fusion site between a mutated non-cytotoxic protease and a peptide (fusion partner) has been introduced and a cleavage amino acid sequence (LVPRGS) of the thrombin-like enzyme batroxobin, a protein cleavage enzyme, has been introduced so that it can cleave between the mutated non-toxic protease and the peptide (fusion partner) to form heterodimers linked by a disulfide bond.

FIG. 6 schematically shows the structure of a fusion non-toxic protease for expression in the yeast *Pichia pastoris*.

FIG. 10 shows the results of codon-optimizing the mutated non-toxic proteases according to various embodiments of the present invention so as to be suitable for expression in *E. coli*, and then analyzing the expression patterns thereof in *E. coli* by Coomassie blue staining.

FIG. 11 shows the results of codon-optimizing the fusion non-toxic proteases according to various embodiments of the present invention so as to be suitable for expression in *E. coli*, and then analyzing the expression patterns thereof in *E. coli* by Coomassie blue staining.

FIG. 14 shows the results of purifying the mutated non-toxic protease and fusion non-toxic protease according to various embodiments of the present invention, and then analyzing the non-toxic proteases by Coomassie blue staining and Western blotting.

FIG. 16 shows the results of comparing the amounts of wild-type and mutated non-toxic proteases present in insoluble fractions (A) with the amounts of wild-type and mutant non-toxic proteases recoverable by refolding (B).

FIG. 18 shows the results of analyzing the cleavage activities of the mutated non-toxic protease and fusion non-toxic protease according to the present invention by Coomassie blue staining using the SNAP25-ANNEXIN V fusion protein.

FIG. 21 shows the results of performing SDS-PAGE electrophoresis and Coomassie staining after fermenting and purifying a large amount of a wild-type non-toxic protease.

FIG. 22 shows the results of performing SDS-PAGE electrophoresis and Coomassie staining after fermenting and purifying a large amount of a mutated non-toxic protease (C430S) according to the present invention.

FIG. 23 shows the results of SDS-PAGE electrophoresis and Coomassie staining after fermenting and purifying a large amount of a mutated non-toxic protease (C430A) according to the present invention.

FIG. 24 shows the results of SDS-PAGE electrophoresis and Coomassie staining after fermenting and purifying a large amount of a mutated non-toxic protease (C430G) according to the present invention.

FIG. 25 shows the results of SDS-PAGE electrophoresis and Coomassie staining after fermenting and purifying a large amount of a fusion non-toxic protease (C430G-BFG-FRP) according to the present invention.

FIG. 26 is a graph comparing the water-soluble protease formation rate and purification yield of each of the wild-type non-toxic protease and the mutant non-toxic protease according to the present invention.

DETAILED DESCRIPTION AND PREFERRED EMBODIMENTS OF THE INVENTION

Figure 1:
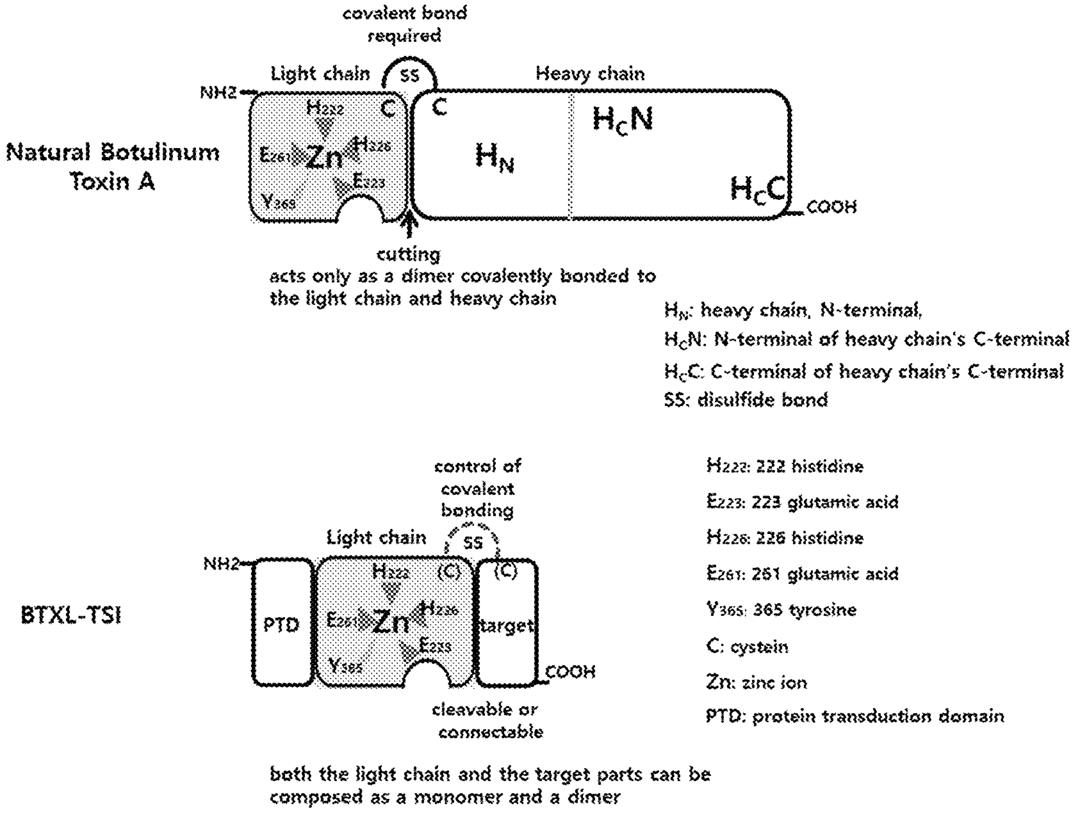
FIG. 1 schematically shows the structural difference between a mutated non-toxic protease according to the present invention and a wild-type non-toxic protease.
Figure 2:
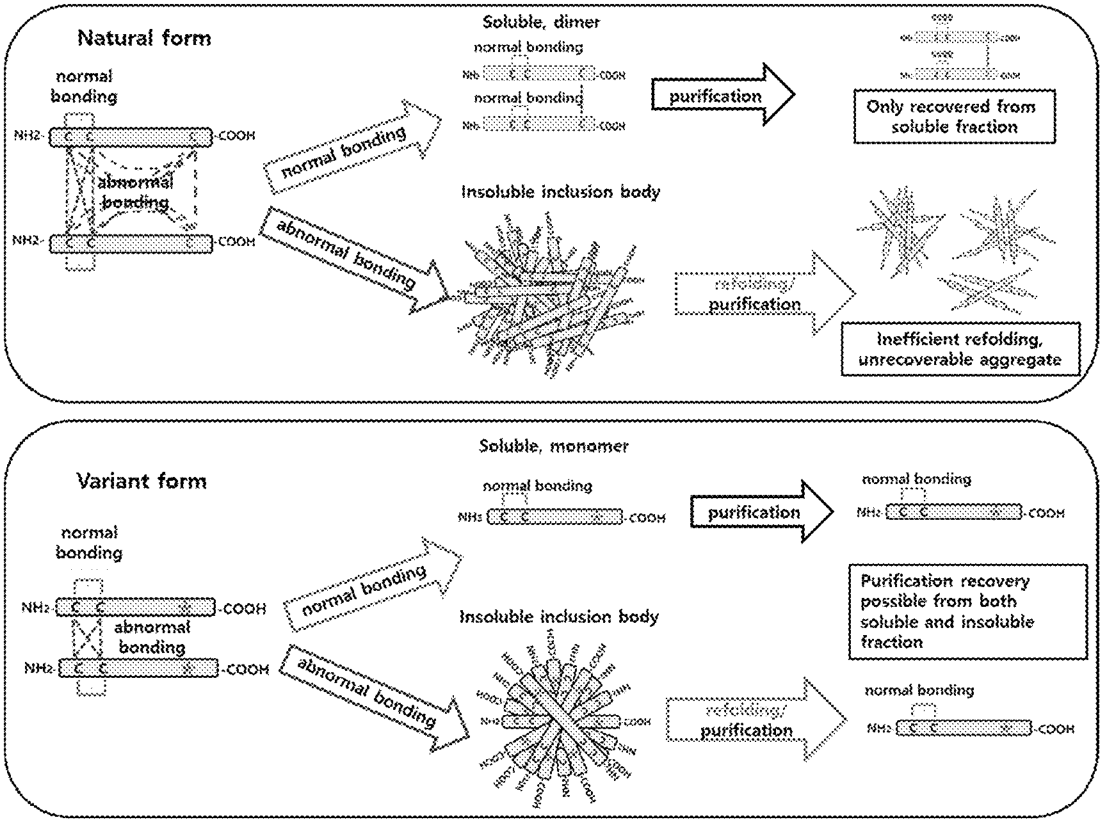
FIG. 2 schematically shows the principle that irreversible insoluble inclusion bodies are formed as a result of expression of the wild-type non-toxic protease and this formation is inhibited in the mutated non-toxic protease according to the present invention.

Unless otherwise defined, all technical and scientific terms used in the present specification have the same meanings as commonly understood by those skilled in the art to which the present disclosure pertains. In general, the nomenclature used in the present specification is well known and commonly used in the art.

In the present invention, it has been found that, when a mutation at the amino acid cysteine at position 430 of a wild-type protease is induced in order to solve the problem associated with the decrease in productivity resulting from protein aggregation which frequently occurs during purification of the wild-type non-toxic protease in a process of producing the non-toxic protease using a recombinant microorganism, protein aggregation resulting from inclusion body formation is inhibited while the protease activity is maintained, and thus the non-toxic protease contained in an insoluble fraction can be recovered even by a simple refolding process alone, and even when various functional peptides are fused to the mutated non-toxic protease, the fusion mutated non-toxic protease can be produced with high productivity.

Therefore, in one aspect, the present invention is directed to a mutated non-toxic protease in which the amino acid cysteine at position 430 of a non-toxic protease represented by the amino acid sequence of SEQ ID NO: 1 is substituted with an amino acid other than cysteine.

In the present invention, the amino acid cysteine at position 430 of the non-toxic protease is substituted with any amino acid other than cysteine so as not to form an inappropriate disulfide bond with another cysteine. The amino acid substituting for the cysteine at position 430 is not limited, but the cysteine (Cys) may preferably be substituted with glycine (Gly), alanine (Ala) or serine (Ser).

In another aspect, the present invention is directed to a fusion non-toxic proteinase in which the mutated non-toxic protease is fused with any one or more peptides selected from the group consisting of:

i) a cell penetrating peptide;
ii) a belt domain fragment peptide; and
iii) a cell targeting peptide.

In the present invention, the cell penetrating peptide may be represented by the amino acid sequence of SEQ ID NO: 3, the belt domain fragment peptide may be represented by the amino acid sequence of SEQ ID NO: 5, and the cell targeting peptide may be represented by the amino acid sequence of SEQ ID NO: 7, but the present invention is not limited thereto. Preferably, the fusion non-toxic protease is for expression in *E. coli.*

In still another aspect, the present invention is directed to a fusion non-toxic proteinase in which the mutated non-toxic protease is fused with any one or more peptides selected from the group consisting of:

i) a yeast secretion signal peptide;
ii) a cell penetrating peptide; and
ii) a cell targeting peptide. Preferably, the fusion non-toxic protease is for expression in yeast.

In the present invention, the yeast secretion signal peptide may be represented by the amino acid sequence of SEQ ID NO: 46, the cell penetrating peptide may be represented by the amino acid sequence of SEQ ID NO: 3, and the cell targeting peptide may be represented by the amino acid sequence of SEQ ID NO: 7, but the present invention is not limited thereto.

In the present invention, when the non-toxic protease constituting the fusion non-toxic protease is fused with another peptide at its N-terminus, the fusion may be performed after removal of the amino acid methionine at position 1.

In the present invention, a tag peptide for purification may further be fused to the mutated non-toxic protease or the fusion non-toxic protease. The tag peptide for purification may be selected from the group consisting of glutathione-S-transferase (GST), C-myc tag, a chitin-binding domain, streptavidin binding protein (SBP), a cellulose-binding domain, a calmodulin-binding peptide, S-tag, Strep-tag II, FLA, protein A, protein G, histidine affinity tag (HAT), poly-His, thioredoxin, pelB leader, and maltose binding protein (MBP), but is not limited thereto. It is possible use any tag peptide for purification that is used in a process of expressing and purifying a protein in a microorganism in the art. It will be apparent to those skilled in the art that the peptide for purification may be cleaved according to a method known in the art after the completion of purification, and a mutated non-toxic protease or fusion non-toxic protease from which the tag peptide for purification has been detached may be used for its original purpose.

In the present invention, any one of the peptides (i.e., a peptide for fusion or purification) may be fused directly or via a linker to the non-toxic protease, and the linker sequence comprises about 3 to 20 amino acids, more preferably about 3 to 10 amino acids. The linker sequence is preferably flexible so that the non-toxic protease is not maintained in an undesirable conformation. The linker sequence may be used, for example, to space the non-toxic protease moiety apart from the fused peptide. Specifically, when the non-toxic protease is fused with two or more peptides selected from the group consisting of a cell penetrating peptide, a belt domain fragment peptide, a cell targeting peptide, a yeast secretion signal peptide, and a tag peptide for purification, the peptide linker sequence may be appropriately placed as needed between the non-toxic protease and the peptide and/or between any two or more selected peptides to provide molecular flexibility. In order to provide flexibility, the linker preferably predominantly comprises amino acids having small side chains, such as glycine, alanine and serine. Preferably, at least about 80 or 90 percent of the linker sequence comprises a glycine, alanine or serine residue, in particular a glycine or serine residue. One suitable linker sequence may be a peptide linker, preferably represented by $(Gly)_N$ (wherein N is an integer ranging from 3 to 10), but is not limited thereto.

The present invention may further comprise a peptide sequence cleavable by a protease for cleavage between the C-terminus of the non-toxic protease and the N-terminus of a peptide selected from the group consisting of a cell penetrating peptide, a belt domain fragment peptide, a cell targeting peptide, a yeast secretion signal peptide, and a tag peptide for purification.

In the present invention, the cleavable peptide sequence may be LVPRGS, which is one of the cleavage sequences of the thrombin-like enzyme batroxobin, but is not limited thereto. In one embodiment, the cleavable peptide sequence is derived from the cleavage sequence of human fibrinogen alpha-chain, which is one of the cleavage sequences of the thrombin-like enzyme batroxobin, which is a protein cleaving enzyme. When the peptide fused with a non-toxic protease is cleaved by the cleavage sequence, the non-toxic protease may be linked to the cleaved peptide by a disulfide bond to form a heterodimer.

However, any proteases that may cleave the peptide fused with the non-toxic protease include, without limitation, trypsin, pepsin, Lys-C endoproteinase, Lys-N endoproteinase, arginyl, endopeptidase, plasmin, omptin and clostridial proteases, as described in EP2524963. In one embodiment, the protease for cleavage is trypsin or Lys-C endoproteinase. In one embodiment, the protease is a protease that cleaves a non-toxic protease non-native (i.e. exogenous) cleavage site. Non-native proteases that may be utilized include, but are not limited to, enterokinase (DDDDK↓) (SEQ ID NO: 50), factor Xa (IEGR↓ (SEQ ID NO: 51)/IDGR↓) (SEQ ID NO: 52), TEV (Tobacco Etch Virus) (ENLYFQ↓G) (SEQ ID NO: 53), thrombin (LVPR↓GS) (SEQ ID NO: 54), and precleavage (LEVLFQ↓GP) (SEQ ID NO: 55), (↓ indicates a cleavage site). In the present invention, the cell penetrating peptide may be selected from the group consisting of Protein-derived Penetration (RQIKIWFQNRRMKWKK) (SEQ ID NO: 56), Tat peptide (GRKKRRQRRRPPQ) (SEQ ID NO: 57), pVEC (LLIILRRRIRKQAHAHSK) (SEQ ID NO: 58), chimeric transportan (GWTLNSAGYLLGKINLKALAALAKKIL) (SEQ ID NO: 59), MPG (GALFLGFLGAAGSTMGAWSQPKKKRKV) (SEQ ID NO: 60), Pep-1 (KETWWETWWTEWSQPKKKRKV) (SEQ ID NO: 61), synthetic Polyarginines ((R)n; 6<n<12), MAP (KLALKLALKALKAALKLA) (SEQ ID NO: 62), and $R_6W_3$ (RRWWRRWRR) (SEQ ID NO: 63), but is not limited thereto (see C. Bechara et al. FEBS Letter 587 (2013) 1693-1702).

In one embodiment of the present invention, the cell targeting peptide may be NH2-Thr-Tyr-Arg-Ser-Arg-Lys-Tyr-(Thror Ser)-Ser-Trp-Tyr-COOH [TYRSRKY(S/T) SWY], which is a peptide derived from the amino acids at positions 105 to 115 of human basic fibroblast growth factor, but is not limited thereto. It will be obvious to those skilled in the art that any peptides used as targeting moieties for conventional non-toxic proteases, such as lectin wheat germ agglutinin, nerve growth factor (NGF), epidermal growth factor, an antibody fragment, or a growth hormone releasing hormone (GHRH) ligand (see Elena Fonfria et al., Toxins (Basel). 2018 July; 10(7): 278.) may be used in fusion with the non-toxic protease.

In still another aspect, the present invention is directed to a mutant gene encoding the mutated non-toxic protease.

In the present invention, the mutant gene may be represented by a nucleotide sequence selected from the group consisting of SEQ ID NOs: 30, 32 and 34.

In yet another aspect, the present invention is directed to a gene construct comprising: the mutant gene; and any one or more nucleic acids selected from the group consisting of i) a nucleic acid encoding a cell penetrating peptide;

ii) a nucleic acid encoding a belt domain fragment peptide; and iii) a nucleic acid encoding a cell targeting peptide.

In the present invention, the nucleic acid encoding the cell penetrating peptide may be represented by the nucleotide sequence of SEQ ID NO: 4, the nucleic acid encoding the belt domain fragment peptide may be represented by the nucleotide sequence of SEQ ID NO: 6, and the nucleic acid encoding the cell targeting peptide may be represented by the nucleotide sequence of SEQ ID NO: 8, but the present invention is not limited thereto.

In another aspect, the present invention is directed to a gene construct comprising: the mutant gene; and any one or more nucleic acids selected from the group consisting of i) a nucleic acid encoding a yeast secretion signal peptide;
ii) a nucleic acid encoding a cell penetrating peptide; and
iii) a nucleic acid encoding a cell targeting peptide.

In the present invention, the nucleic acid encoding the yeast secretion signal peptide may be represented by the nucleotide sequence of SEQ ID NO: 47, the nucleic acid encoding the cell penetrating peptide may be represented by the nucleotide sequence of SEQ ID NO: 4, and the nucleic acid encoding the cell targeting peptide may be represented by the nucleotide sequence of SEQ ID NO: 8, but the present invention is not limited thereto.

In the present invention, the mutant gene or gene construct may further comprise a nucleic acid encoding a tag peptide for purification. The tag peptide for purification may be selected from the group consisting of glutathione-S-transferase (GST), C-myc tag, a chitin-binding domain, streptavidin binding protein (SBP), a cellulose-binding domain, a calmodulin-binding peptide, S-tag, Strep-tag II, FLA, protein A, protein G, histidine affinity tag (HAT), poly-His, thioredoxin, pelB leader, and maltose binding protein (MBP), but is not limited thereto. It is possible to use any tag peptide for purification that is used in a process of expressing and purifying a protein in a microorganism in the art.

In the present invention, the gene construct may further comprise a nucleic acid encoding the linker peptide that connects the peptide to the non-toxic protease, wherein the nucleic acid encoding the linker peptide may be represented by the nucleotide sequence of SEQ ID NO: 26.

The present invention may further comprise a nucleic acid encoding a peptide sequence cleavable by a cleavage protease between the C-terminus of the non-toxic protease and the N-terminus of a peptide selected from the group consisting of a cell penetrating peptide, a belt domain fragment peptide, a cell targeting peptide, a yeast secretion signal peptide, and a tag peptide for purification. The nucleic acid encoding the cleavable peptide sequence may be represented by the nucleotide sequence of SEQ ID NO: 28, but is not limited thereto.

The present invention encompasses fragments and variants of polypeptides (proteins) and genes (nucleic acids) provided as specific sequences as long as they maintain their original structural and/or functional characteristics. That is, these fragments and variants may have a sequence homology of at least 90%, more preferably at least 95%, at least 97% or at least 99% to the sequences provided in the present invention.

In another aspect, the present invention is directed to a recombinant vector having the mutant gene introduced therein.

In the present invention, as the recombinant vector, there may be used without limitation any vector known in the art that may be introduced into bacterial cells, yeast cells, mammalian cells, insect cells, plant cells, or amphibian cells and used for overexpression of recombinant proteins. Preferably, there may be used a recombinant vector that may be introduced into bacterial cells or yeast cells and used for overexpression of recombinant proteins. Preferably, the pET22b(+) (Novagen, Merk Millipore) vector may be used for expression in *E. coli* and the pPIC9 vector may be used for expression in yeast. However, it will be obvious to those skilled in the art that vectors usable in the present invention are not limited to these vectors, and vectors known in the art may be applied for the expression of the mutant non-toxic protease or fusion non-toxic protease of the present invention.

In another aspect, the present invention is directed to a recombinant microorganism having the recombinant vector introduced therein.

In the present invention, the recombinant microorganism may be bacteria or yeast, but is not limited thereto.

In another aspect, the present invention is directed to a method for producing a mutated non-toxic protease or a fusion non-toxic protease, the method comprising steps of:

(a) producing the mutated non-toxic protease or the fusion non-toxic protease by culturing the recombinant microorganism;
(b) disrupting the recombinant microorganism; and
(c) purifying the mutated non-toxic protease or the fusion non-toxic protease from the disrupted recombinant microorganism.

In the present invention, step (a) may be performed in two steps: seed culture followed by main culture (i.e., culture for fermentation).

In the present invention, in step (a), the recombinant microorganism may be cultured at 30 to 38° C., and then when the $OD_{600}$ of the recombinant microorganism reaches 0.2 to 0.4, the culture temperature may be lowered to 16 to 20° C. and the recombinant microorganism may be further cultured. Preferably, in the main culture step in step (a), the recombinant microorganism may be cultured at 36 to 38° C., more preferably 36.5 to 37.5° C., and then when the $OD_{600}$ of the recombinant microorganism reaches 0.25 to 0.35, the culture temperature may be 17 to 19° C. and the recombinant microorganism may be further cultured. In this case, protein expression may be induced by adding 0.4 to 0.6 mM IPTG to the culture medium when the $OD_{600}$ reaches 0.5 to 0.7. Through this process, recovery of the mutated non-toxic protease or the fusion non-toxic protease according to the present invention from a soluble fraction is significantly increased. That is, in the initial stage, culture is performed at a high temperature in order to rapidly increase the amount of the recombinant microorganism, and then when the recombinant microorganism reaches a certain amount, the culture temperature of the recombinant microorganism is lowered to slow the metabolism of the recombinant microorganism. In addition, expression of a non-toxic protease is gradually induced by adding a small amount of IPTG, so that the refolding efficiency of the non-toxic protease is increased, and thus most of the non-toxic protease may be included in the soluble fraction. This is demonstrated by the results obtained in the present invention.

The effect of increasing the expression level of the protease in the soluble fraction is particularly pronounced in the case of the mutated protease C430G derived in the present invention. This is believed to be because, in the case of a wild-type mutant protease, a disulfide bond between cysteines is induced, and in the case of C430S and C430A, which are other mutated proteases, some non-specific disulfide bonds are induced.

In the present invention, step (c) may comprise separating the disrupted recombinant microorganism into a soluble fraction and an insoluble fraction by centrifugation, and independently purifying the mutated non-toxic protease or the fusion non-toxic protease from each fraction.

In the present invention, step (c) may comprise separating the disrupted recombinant microorganism into a soluble fraction and an insoluble fraction by centrifugation, and purifying the mutated non-toxic protease or the fusion non-toxic protease from the soluble fraction.

In the present invention, suitable medium and culture conditions that are used to culture the recombinant microorganism may be those known in the art. For example, the recombinant microorganism may be inoculated and cultured in a suitable medium for transformed *E. coli* or yeast, and then expression of the protein may be induced under suitable conditions. For example, expression of the protein in *E. coli* may be induced by supplying isopropyl-β-D-thiogalactoside, and expression of the protein in isopropyl-β or methanol-assimilating yeast may be induced by supplying methyl alcohol. After completion of the step of inducing protein expression by culture, the culture or culture medium may be recovered, and "pure recombinant protein" may be recovered therefrom. As used herein, the term "pure recombinant protein" means that the recombinant protein does not contain 5% or more, preferably 1% or more of any other proteins derived from the host cell, other than the recombinant protein of the present invention and a protein derived from the DNA sequence encoding the same.

Purification of the recombinant protein expressed in the transformed microorganism may be performed by various methods known in the art. Usually, the cell lysate or culture may be centrifuged to remove cell debris, culture impurities, etc., and then subjected to precipitation, for example, salting out (ammonium sulfate precipitation and sodium phosphate precipitation), solvent precipitation (protein fraction precipitation using acetone, ethanol, isopropyl alcohol, etc.) and the like, and subjected to dialysis, electrophoresis, and various types of column chromatography. As the types of chromatography, techniques such as ion exchange chromatography, gel-filtration chromatography, HPLC, reverse phase HPLC, adsorption chromatography, affinity column chromatography and ultrafiltration may be used alone or in combination.

In the present invention, the term "non-toxic protease" is meant to include a peptide that has significantly reduced toxicity due to removal of the heavy chain domain from the natural botulinum toxin type A and has the natural botulinum toxin type A light-chain domain having protease activity, as well as a variant of the peptide.

In another aspect, the present invention is directed to a pharmaceutical composition for treating Dystonia containing the mutated or fusion non-toxic protease as an active ingredient.

In the present invention, the pharmaceutical composition may be for transdermal administration, but is not limited thereto.

In another aspect, the present invention is directed to a method for alleviating or treating symptoms of Dystonia, the method comprising a step of administering the mutated or fusion non-toxic protease to a subject in need of alleviation or treatment of symptoms of Dystonia.

In another aspect, the present invention is directed to the use of the mutated or fusion non-toxic protease for the manufacture of a medicament for use in the alleviation or treatment of symptoms of Dystonia.

In another aspect, the present invention is directed to the use of the above-described mutated or fusion non-toxic protease for use in a method for alleviating or treating symptoms of Dystonia.

In the present invention, the muscular dystonia may be selected from the group consisting of facial spasm, eyelid spasm, torticollis, blepharospasm, spasmodic torticollis, cervical dystonia, oromandibular dystonia, spasmodic dysphonia, migraine, anal pruritus, and hyperhidrosis, but is not limited thereto.

In another aspect, the present invention is directed to a hyaluronic acid microneedle patch containing the mutated or fusion non-toxic protease.

In the present invention, the hyaluronic acid microneedle patch may be used for the treatment or alleviation of a symptom selected from the group consisting of facial spasm, eyelid spasm, torticollis, blepharospasm, spasmodic torticollis, cervical dystonia, oromandibular dystonia, spasmodic dysphonia, migraine, anal pruritus, and hyperhidrosis, but is not limited thereto.

As used herein, the term "treating" means reversing, alleviating, inhibiting the progression of, or preventing a disorder or disease to which the term applies, or one or more symptoms of the disorder or disease, unless otherwise stated. As used herein, the term "treatment" refers to the act of treating when 'treating' is defined as above. As used herein, the term "treatment" refers to the act of treating when the term "treating" is defined as above. Accordingly, treatment or therapy of the disease in a mammal may include one or more of the following:

(1) inhibiting the development of the disease;
(2) preventing the spread of the disease;
(3) relieving the disease;
(4) preventing the recurrence of the disease; and
(5) palliating symptoms of the disease.

As used herein, the term "effective amount" means an amount that is high enough to deliver the desired benefit, but low enough to avoid serious side effects within the scope of medical judgment. The amount of the non-toxic protease that is administered into the body by the composition of the present invention may be appropriately adjusted in consideration of the route of administration and the for administration.

The composition of the present invention may be administered to the subject once daily, once every several days, once every several months, or once or more every several years. Unit dosage means physically discrete units suitable for unit administration to human subjects and other mammals, each unit comprising a suitable pharmaceutical carrier and a predetermined amount of the protease of the present invention that exhibits a therapeutic effect. However, the dosage may vary depending on the severity of the patient's disease and the active ingredient and auxiliary active ingredient used. In addition, the total daily dosage may be divided into several times and continuously administered as needed. Accordingly, the above dosage range is not intended to limit the scope of the present invention in any way.

As used herein, the term "pharmaceutically acceptable" refers to a composition which is physiologically acceptable and, when administered to humans, does not cause allergic reactions such as gastrointestinal disorders and dizziness, or similar reactions.

The pharmaceutical composition of the present invention may be formulated using a method known in the art so as to provide quick, sustained or delayed release of the active ingredient after administration to mammals. The dosage forms may be powders, granules, tablets, emulsions, syrups, aerosols, soft or hard gelatin capsules, sterile injection solutions, sterile powders, or patches. In addition, the composition for preventing or treating a disease according to the present invention may be administered through several routes, including oral, transdermal, subcutaneous, intravenous and intramuscular routes. The dosage of the active ingredient may be suitably selected depending on various factors such as the route of administration, and patient's age, sex, weight and severity, and the active ingredient may be administered in combination with a known compound having the effect of preventing, alleviating or treating the symptoms of the disease.

Hereinafter, the present invention will be described in more detail with reference to examples. It will be obvious to those skilled in the art that these examples serve only to illustrate the present invention, and the scope of the present invention is not limited by these examples.

Figure 3:
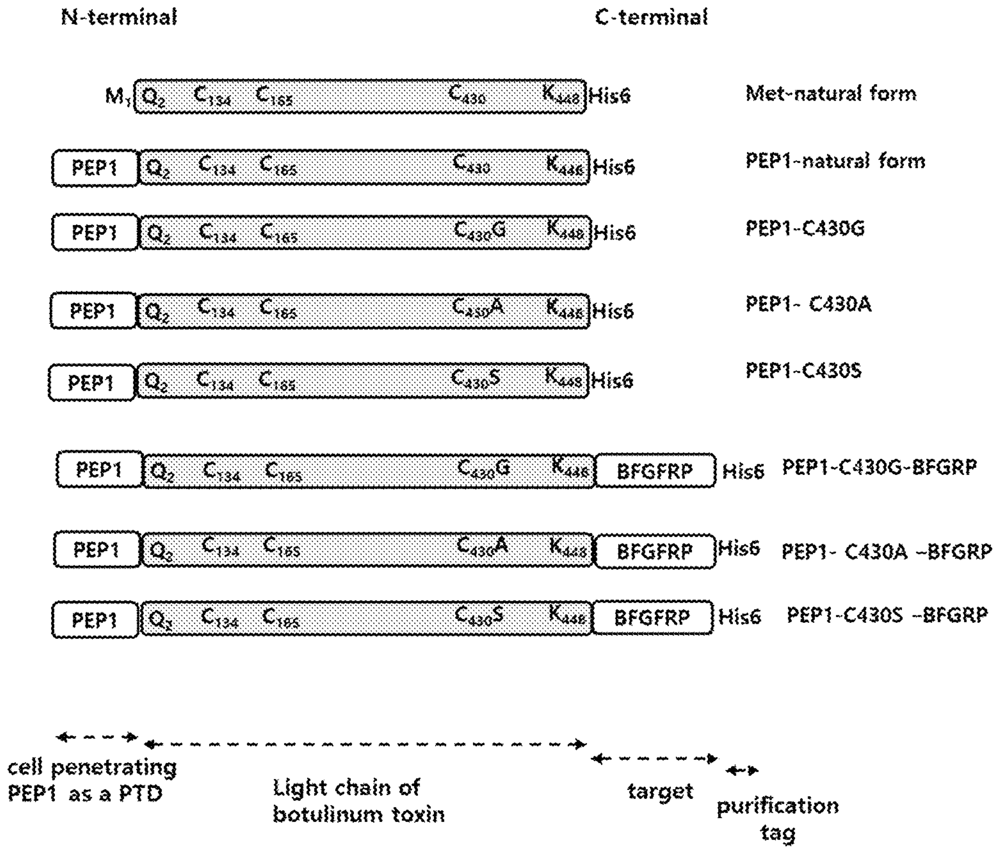
FIG. 3 schematically shows the structures of a mutated non-toxic protease and a fusion non-toxic protease according to various embodiments of the present invention.
Figure 4:
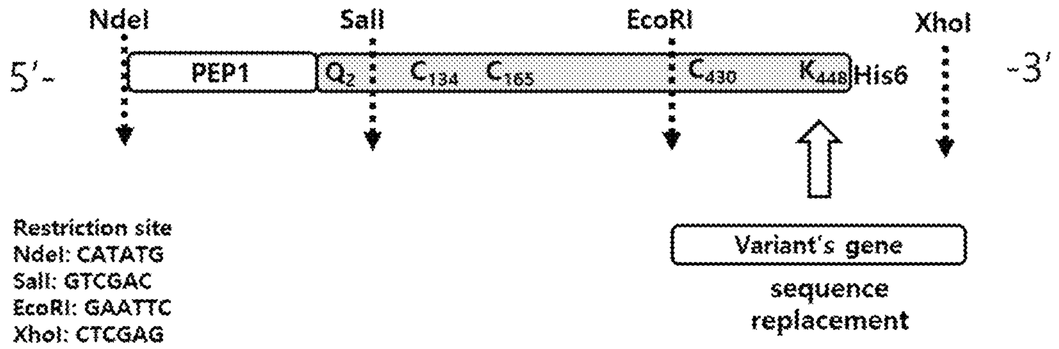
FIG. 4 schematically shows the restriction enzyme positions used in recombinant vector cloning to produce various mutated non-toxic proteases and fusion mutated non-toxic proteases according to the present invention.

Example 1. Construction of Vectors for Expression of Mutated Non-Toxic Proteases and Fusion Non-Toxic Proteases As shown in FIG. 3, expression vectors for producing a mutated non-toxic protease and a fusion non-toxic protease were constructed. To this end, the following nucleotide sequences were synthesized: a nucleotide sequence (SEQ ID NO: 2) encoding a wild-type non-toxic protease (BTX-LC) represented by the amino acid sequence of SEQ ID NO: 1; a nucleotide sequence (SEQ ID NO: 4) encoding a cell penetrating peptide (PEP1); a nucleotide sequence (SEQ ID NO: 6) encoding a belt domain peptide fragment (belt'); and a nucleotide sequence (SEQ ID NO: 8) encoding a targeting peptide.

Based on the synthesized nucleotide sequences, BTX-LC and PEP1-(ΔM)BTX-L-His were cloned by restriction enzymes (Ndel and XhoI) into the multiple cloning site (MCS) downstream of the T7 promoter-lac operator of the expression vector pET22b for *E. coli*. Thereafter, using the restriction enzymes EcoRI and XhoI, recombinant vectors capable of expressing various non-toxic proteases shown in Table 1 below, including the following non-toxic proteases, were constructed: PEP1-(Δ)BTX-L-His (*E. coli* codon optimization; theoretical pI/Mw: 8.66/55003.59 Da) capable of improving expression efficiency in *E. coli*; a mutated non-toxic protease in which the amino acid cysteine (Cys) at position 430 of the wind-type non-toxic protease is substituted with each of glycine (Gly), alanine (Ala) and serine (Ser); and a PEP1-(ΔM)BTX-L-BFGFRP-His (theoretical pI/Mw: 8.95/56436.13) fusion non-toxic protease. Table 2 below shows the sequences (gene cassettes for cloning of mutated non-toxic proteases) used in cloning for a point mutation at the amino acid at position 430 of the wild-type protease.

TABLE 1

| | Amino acid sequence | Nucleotide sequence |
|---|---|---|
| BTX-LC | MQFVNKQFNYKDPVNGVDIAYIKIPNVG<br>QMQPVKAFKIHNKIWVIPERDTFTNPEEG<br>DLNPPPEAKQVPVSYYDSTYLSTDNEKDN<br>YLKGVTKLFERIYSTDLGRMLLTSIVRGIP<br>FWGGSTIDTELKVIDTNCINVIQPDGSYRS<br>EELNLVIIGPSADIIQFECKSFGHEVLNLTR<br>NGYGSTQYIRFSPDFTFGFEESLEVDTNPL<br>LGAGKFATDPAVTLAHELIHAGHRLYGIA<br>INPNRVFKVNTNAYYEMSGLEVSFEELRT<br>FGGHDAKFIDSLQENEFRLYYYNKFKDIA<br>STLNKAKSIVGTTASLQYMKNVFKEKYLL<br>SEDTSGKFSVDKLKFDKLYKMLTEIYTED<br>NFVKFFKVLNRKTYLNFDKAVFKINIVPK<br>VNYTIYDGFNLRNTNLAANFNGQNTEINN<br>MNFTKLKNFTGLFEFYKLLCVRGIITSKTK<br>SLDKGYNK (SEQ ID NO: 1) | 5'-<br>atgcaatttgttaataaacaatttaattataaagatcctgtaaatggtgttgatat<br>tgcttatataaaaattccaaatgtaggacaaatgcaaccagtaaaagctttta<br>aaattcataataaaatatgggttattccagaaagagatacatttacaaatcct<br>gaagaaggagatttaaatccaccaccagaagcaaaacaagttccagtttca<br>tattatgattcaacatatttaagtacagataatgaaaaagataattatttaaagg<br>gagttacaaaattatttgagagaatttattcaactgatcttggaagaatgttgtt<br>aacatcaatagtaaggggaataccattttggggtggaagtacaatagatac<br>agaattaaaagttattgatactaattgtattaatgtgatacaaccagatggtag<br>ttatagatcagaagaacttaatctagtaataataggaccctcagctgatattat<br>acagtttgaatgtaaaagctttggacatgaagttttgaatcttacgcgaaatg<br>gttatggctctactcaatacattagatttagcccagattttacatttggttttgag<br>gagtcacttgaagttgatacaaatcctcttttaggtgcaggcaaatttgctac<br>agatccagcagtaacattagcacatgaacttatacatgctggacatagattat<br>atggaatagcaattaatccaaatagggtttttaaagtaaatactaatgcctatt<br>atgaaatgagtgggttagaagtaagctttgaggaacttagaacatttgggg<br>gacatgatgcaaagtttatagatagtttacaggaaaacgaatttcgtctatatt<br>attataataagtttaaagatatagcaagtacacttaataaagctaaatcaatag<br>taggtactactgcttcattacagtatatgaaaaatgtttttaaagagaaatatct<br>cctatctgaagatacatctggaaaattttcggtagataaattaaaatttgataa<br>gttatacaaaatgttaacagagatttacacagaggataattttgttaagtttttt<br>aaagtacttaacagaaaaacatatttgaattttgataaagccgtatttaagata<br>aatatagtacctaaggtaaattacacaatatatgatggatttaatttaagaaat<br>acaaatttagcagcaaactttaatggtcaaaatacagaaattaataatatgaa<br>ttttactaaactaaaaaatttactggattgtttgaattttataagttgctatgtgt<br>aagagggataataacttctaaaactaaatcattagataaaggatacaataag-<br>3' (SEQ ID NO: 2) |
| PEP1 | MKETWWETWWTEWSQPKKKRKV (SEQ<br>ID NO: 3) | 5'-<br>atgaaggaaacttggtgggaaacttggtggactgaatggtctcaaccaaag<br>aagaagagaaaggtt-3' (SEQ ID NO: 4) |
| Belt | ALNDLC (SEQ ID NO: 5) | Gcgctgaacgatctgtgc (SEQ ID NO: 6) |
| BFGFRP | TYRSRKYXSWY (SEQ ID NO: 7)<br>(X stands for S or T.) | 5'-ACCTATCGCAGCCGCAAATATASC<br>AGCTGGTAT-3' (SEQ ID NO: 8)<br>(ASC stands for AGC or ACC.) |
| PEP1-<br>(ΔM)<br>BTX-L-His | MKETWWETWWTEWSQPKKKRKVQFVN<br>KQFNYKDPVNGVDIAYIKIPNVGQMQPV<br>KAFKIHNKIWVIPERDTFTNPEEGDLNPPP<br>EAKQVPVSYYDSTYLSTDNEKDNYLKGV<br>TKLFERIYSTDLGRMLLTSIVRGIPFWGGS<br>TIDTELKVIDTNCINVIQPDGSYRSEELNL<br>VIIGPSADIIQFECKSFGHEVLNLTRNGYGS<br>TQYIRFSPDFTFGFEESLEVDTNPLLGAGK<br>FATDPAVTLAHELIHAGHRLYGIAINPNR<br>VFKVNTNAYYEMSGLEVSFEELRTFGGH<br>DAKFIDSLQENEFRLYYYNKFKDIASTLN | 5'-<br>atgaaggaaacttggtgggaaacttggtggactgaatggtctcaaccaaag<br>aagaagagaaaggttcaatttgttaataaacaatttaattataaagatcctgta<br>aatggtgttgatattgcttatataaaaattccaaatgtaggacaaatgcaacc<br>agtaaaagcttttaaaattcataataaaatatgggttattccagaaagagata<br>catttacaaatcctgaagaaggagatttaaatccaccaccagaagcaaaac<br>aagttccagtttcatattatgattcaacatatttaagtacagataatgaaaaag<br>ataattatttaaagggagttacaaaattatttgagagaatttattcaactgatctt<br>ggaagaatgttgttaacatcaatagtaaggggaataccattttggggtggaa<br>gtacaatagatacagaattaaaagttattgatactaattgtattaatgtgatac<br>aaccagatggtagttatagatcagaagaacttaatctagtaataataggacc |

TABLE 1-continued

| | Amino acid sequence | Nucleotide sequence |
|---|---|---|
| | KAKSIVGTTASLQYMKNVFKEKYLLSEDT<br>SGKESVDKLKEDKLYKMLTEIYTEDNEVK<br>FEKVLNRKTYLNEDKAVFKINIVPKVNYTI<br>YDGENLRNTNLAANENGQNTEINNMNFT<br>KLKNFTGLFEFYKLLCVRGIITSKTKSLDK<br>GYNKHHHHHH (SEQ ID NO: 9) | ctcagctgatattatacagtttgaatgtaaaagctttggacatgaagttttgaa<br>tcttacgcgaaatggttatggctctactcaatacattagatttagcccagatttt<br>acatttggttttgaggagtcacttgaagttgatacaaatcctcttttaggtgca<br>ggcaaatttgctacagatccagcagtaacattagcacatgaacttatacatg<br>ctggacatagattatatggaatagcaattaatccaaatagggtttttaaagta<br>aatactaatgcctattatgaaatgagtgggttagaagtaagctttgaggaact<br>tagaacatttggggacatgatgcaaagtttatagatagtttacaggaaaac<br>gaatttcgtctatattattataataagtttaaagatatagcaagtacacttaata<br>aagctaaatcaatagtaggtactactgcttcattacagtatatgaaaaatgttt<br>ttaaagagaaatatctcctatctgaagatacatctggaaaattttcggtagata<br>aattaaaatttgataagttatacaaaatgttaacagagatttacacagaggat<br>aattttgttaagtttttaaagtacttaacagaaaaacatatttgaattttgataaa<br>gccgtatttaagataaatatagtacctaaggtaaattacacaatatatgatgg<br>atttaatttaagaaatacaaatttagcagcaaactttaatggtcaaaatacaga<br>aattaataatatgaattttactaaactaaaaaattttactggattgtttgaatttta<br>taagttgctatgtgtaagagggataataacttctaaaactaaatcattagataa<br>aggatacaataagcatcaccatcaccatcactaa-3'<br>(SEQ ID NO: 10) |
| PEP1-<br>(ΔM)<br>BTX-L-<br>His<br>(*E. coli*<br>codon<br>opti-<br>mization) | MKETWWETWWTEWSQPKKKRKVQFVN<br>KQFNYKDPVNGVDIAYIKIPNVGQMQPV<br>KAFKIHNKIWVIPERDTFTNPEEGDLNPPP<br>EAKQVPVSYYDSTYLSTDNEKDNYLKGV<br>TKLFERIYSTDLGRMLLTSIVRGIPFWGGS<br>TIDTELKVIDTNCINVIQPDGSYRSEELNL<br>VIIGPSADIIQFECKSFGHEVLNLTRNGYGS<br>TQYIRFSPDFTFGFEESLEVDTNPLLGAGK<br>FATDPAVTLAHELIHAGHRLYGIAINPNR<br>VFKVNTNAYYEMSGLEVSFEELRTFGGH<br>DAKFIDSLQENEFRLYYYNKFKDIASTLN<br>KAKSIVGTTASLQYMKNVFKEKYLLSEDT<br>SGKFSVDKLKFDKLYKMLTEIYTEDNFVK<br>FFKVLNRKTYLNFDKAVFKINIVPKVNYTI<br>YDGFNLRNTNLAANFNGQNTEINNMNFT<br>KLKNFTGLFEFYKLLCVRGHTSKTKSLDK<br>GYNKHHHHHH<br>(SEQ ID NO: 11) | 5'-<br>catatgaaggaaacttggtgggaaacttggtggaccgaatggtctcaacca<br>aagaagaagcgcaaggttcaatttgttaataaacaatttaattataaagatcc<br>agtaaatggtgtcgacattgcttatatcaaaattccaaatgtaggccaaatgc<br>aaccagtaaaagcttttaaaattcataataaaatctgggttattccagaacgc<br>gatacctttaccaatccggaagaaggtgatctgaatccaccaccagaagca<br>aaacaagttccagttagctattatgatagcacctatctgagcaccgataatga<br>aaaagataattatctgaagggcgttaccaaactgtttgagcgcatttatagca<br>ctgatctgggtcgcatgctgctgaccagcatcgtacgcggtatcccatttg<br>gggtggtagcaccatcgataccgaactgaaagttattgatactaattgtatta<br>atgtgatccaaccagatggtagctatcgcagcgaagaactgaatctggtaa<br>tcatcggtccgagcgctgatattatccagtttgaatgtaaaagctttggtcat<br>gaagttctgaatctgacccgtaatggttatggcagcacccaatacattcgctt<br>tagcccagattttacctttggttagaggagagcctggaagttgataccaatc<br>cgctgctgggtgcaggcaaatttgctaccgatccagcagtaaccctggca<br>catgaactgatacatgctggccatcgcctgtatggtatcgcaattaatccaa<br>atcgcgtttttaaagtaaataccaatgcctattatgaaatgagcggtctggaa<br>gtaagctttgaggaactgcgcacctttggtggtcatgatgcaaagtttatcga<br>tagcctgcaggaaaacgaatttcgtctgtattattataataagtttaaagatat<br>cgcaagcaccctgaataaagctaaaagcatcgtaggtaccaccgctagcc<br>tgcagtatatgaaaaatgtttttaaagagaaatatctgctgtctgaagatacct<br>ctggcaaatttagcgtagataaactgaaatttgataagctgtacaaaatgctg<br>accgagatttacaccgaggataattttgttaagtttttaaagtactgaaccgc<br>aaaacctatctgaattttgataaagccgtatttaagatcaatatcgtaccgaa<br>ggtaaattacaccatctatgatggttttaatctgcgcaataccaatctggcag<br>caaactttaatggtcaaaataccgaaattaataatatgaattttaccaaactga<br>aaaattttaccggtctgtttgaattctataagctgctgTGTgtacgcggtat<br>catcaccagcaaaaccaaaagcctggataaaggctacaataagcatcacc<br>atcaccatcactaataactcgag-3'<br>(SEQ ID NO: 12) |
| PEP1-<br>(ΔM)<br>BTX-L<br>(C430G)-<br>His | MKETWWETWWTEWSQPKKKRKVQFVN<br>KQFNYKDPVNGVDIAYIKIPNVGQMQPV<br>KAFKIHNKIWVIPERDTFTNPEEGDLNPPP<br>EAKQVPVSYYDSTYLSTDNEKDNYLKGV<br>TKLFERIYSTDLGRMLLTSIVRGIPFWGGS<br>TIDTELKVIDTNCINVIQPDGSYRSEELNL<br>VIIGPSADIIQFECKSFGHEVLNLTRNGYGS<br>TQYIRFSPDFTFGFEESLEVDTNPLLGAGK<br>FATDPAVTLAHELIHAGHRLYGIAINPNR<br>VFKVNTNAYYEMSGLEVSFEELRTFGGH<br>DAKFIDSLQENEFRLYYYNKFKDIASTLN<br>KAKSIVGTTASLQYMKNVFKEKYLLSEDT<br>SGKFSVDKLKFDKLYKMLTEIYTEDNFVK<br>FFKVLNRKTYLNFDKAVFKINIVPKVNYTI<br>YDGFNLRNTNLAANFNGQNTEINNMNFT<br>KLKNFTGLFEFYKLLGVRGIITSKTKSLDK<br>GYNKHHHHHH (SEQ ID NO: 13) | 5'-<br>catatgaaggaaacttggtgggaaacttggtggaccgaatggtctcaacca<br>aagaagaagcgcaaggttcaatttgttaataaacaatttaattataaagatcc<br>agtaaatggtgtcgacattgcttatatcaaaattccaaatgtaggccaaatgc<br>aaccagtaaaagcttttaaaattcataataaaatctgggttattccagaacgc<br>gatacctttaccaatccggaagaaggtgatctgaatccaccaccagaagca<br>aaacaagttccagttagctattatgatagcacctatctgagcaccgataatga<br>aaaagataattatctgaagggcgttaccaaactgtttgagcgcatttatagca<br>ctgatctgggtcgcatgctgctgaccagcatcgtacgcggtatcccatttg<br>gggtggtagcaccatcgataccgaactgaaagttattgatactaattgtatta<br>atgtgatccaaccagatggtagctatcgcagcgaagaactgaatctggtaa<br>tcatcggtccgagcgctgatattatccagtagaatgtaaaagctttggtcat<br>gaagttctgaatctgacccgtaatggttatggcagcacccaatacattcgctt<br>tagcccagatatacctaggattgaggagagcctggaagttgataccaatc<br>cgctgctgggtgcaggcaaatttgctaccgatccagcagtaaccctggca<br>catgaactgatacatgctggccatcgcctgtatggtatcgcaattaatccaa<br>atcgcgtttttaaagtaaataccaatgcctattatgaaatgagcggtctggaa<br>gtaagctttgaggaactgcgcacctttggtggtcatgatgcaaagtttatcga<br>tagcctgcaggaaaacgaatttcgtctgtattattataataagtttaaagatat<br>cgcaagcaccctgaataaagctaaaagcatcgtaggtaccaccgctagcc<br>tgcagtatatgaaaaatgtttttaaagagaaatatctgctgtctgaagatacct<br>ctggcaaatttagcgtagataaactgaaatttgataagctgtacaaaatgctg<br>accgagatttacaccgaggataattttgttaagtttttaaagtactgaaccgc<br>aaaacctatctgaattttgataaagccgtatttaagatcaatatcgtaccgaa |

TABLE 1-continued

| | Amino acid sequence | Nucleotide sequence |
|---|---|---|
| | | ggtaaattacaccatctatgatggttttaatctgcgcaataccaatctggcag<br>caaactttaatggtcaaaataccgaaattaataatatgaattttaccaaactga<br>aaaattttaccggtctgtttgaattctataagctgctg**GGC**gtacgcggtat<br>catcaccagcaaaaccaaaagcctggataaaggctacaataagcatcacc<br>atcaccatcactaataactcgag-3' (SEQ ID NO: 14) |
| PEP1-<br>(ΔM)<br>BTX-L<br>(C430A)-<br>His | MKETWWETWWTEWSQPKKKRKVQFVN<br>KQFNYKDPVNGVDIAYIKIPNVGQMQPV<br>KAFKIHNKIWVIPERDTFTNPEEGDLNPPP<br>EAKQVPVSYYDSTYLSTDNEKDNYLKGV<br>TKLFERIYSTDLGRMLLTSIVRGIPFWGGS<br>TIDTELKVIDTNCINVIQPDGSYRSEELNL<br>VIIGPSADIIQFECKSFGHEVLNLTRNGYGS<br>TQYIRFSPDFTEGFEESLEVDTNPLLGAGK<br>FATDPAVTLAHELIHAGHRLYGIAINPNR<br>VFKVNTNAYYEMSGLEVSFEELRTFGGH<br>DAKFIDSLQENEFRLYYYNKFKDIASTLN<br>KAKSIVGTTASLQYMKNVFKEKYLLSEDT<br>SGKESVDKLKEDKLYKMLTEIYTEDNEVK<br>FEKVLNRKTYLNEDKAVFKINIVPKVNYTI<br>YDGENLRNTNLAANENGQNTEINNMNFT<br>KLKNFTGLFEFYKLL**A**VRGHTSKTKSLDK<br>GYNKHHHHHH (SEQ ID NO: 15) | 5'-<br>catatgaaggaaacttggtgggaaacttggtggaccgaatggtctcaacca<br>aagaagaagcgcaaggttcaatttgttaataaacaatttaattataaagatcc<br>agtaaatggtgtcgacattgcttatatcaaaattccaaatgtaggccaaatgc<br>aaccagtaaaagcttttaaaattcataataaaatctgggttattccagaacgc<br>gatacctttaccaatccggaagaaggtgatctgaatccaccaccagaagca<br>aaacaagttccagttagctattatgatagcacctatctgagcaccgataatga<br>aaaagataattatctgaagggcgttaccaaactgtttgagcgcatttatagca<br>ctgatctgggtcgcatgctgctgaccagcatcgtacgcggtatcccattttg<br>gggtggtagcaccatcgataccgaactgaaagttattgatactaattgtatta<br>atgtgatccaaccagatggtagctatcgcagcgaagaactgaatctggtaa<br>tcatcggtccgagcgctgatattatccagtagaatgtaaaagctttggtcat<br>gaagttctgaatctgacccgtaatggttatggcagcacccaatacattcgctt<br>tagcccagatatacctaggattgaggagagcctggaagttgataccaatc<br>cgctgctgggtgcaggcaaatttgctaccgatccagcagtaaccctggca<br>catgaactgatacatgctggccatcgcctgtatggtatcgcaattaatccaa<br>atcgcgtttttaaagtaaataccaatgcctattatgaaatgagcggtctggaa<br>gtaagctttgaggaactgcgcacctttggtggtcatgatgcaaagtttatcga<br>tagcctgcaggaaaacgaatttcgtctgtattattataataagtttaaagatat<br>cgcaagcaccctgaataaagctaaaagcatcgtaggtaccaccgctagcc<br>tgcagtatatgaaaaatgtttttaaagagaaatatctgctgtctgaagatacct<br>ctggcaaatttagcgtagataaactgaaatttgataagctgtacaaaatgctg<br>accgagatttacaccgaggataattttgttaagtttttttaaagtactgaaccgc<br>aaaacctatctgaattttgataaagccgtatttaagatcaatatcgtaccgaa<br>ggtaaattacaccatctatgatggttttaatctgcgcaataccaatctggcag<br>caaactttaatggtcaaaataccgaaattaataatatgaattttaccaaactga<br>aaaattttaccggtctgtttgaattctataagctgctg**GCG**gtacgcggtat<br>catcaccagcaaaaccaaaagcctggataaaggctacaataagcatcacc<br>atcaccatcactaataactcgag-3'<br>(SEQ ID NO: 16) |
| PEP1-<br>(ΔM)<br>BTX-L<br>(C430S)-<br>His | MKETWWETWWTEWSQPKKKRKVQFVN<br>KQFNYKDPVNGVDIAYIKIPNVGQMQPV<br>KAFKIHNKIWVIPERDTFTNPEEGDLNPPP<br>EAKQVPVSYYDSTYLSTDNEKDNYLKGV<br>TKLFERIYSTDLGRMLLTSIVRGIPFWGGS<br>TIDTELKVIDTNCINVIQPDGSYRSEELNL<br>VIIGPSADIIQFECKSFGHEVLNLTRNGYGS<br>TQYIRFSPDFTEGFEESLEVDTNPLLGAGK<br>FATDPAVTLAHELIHAGHRLYGIAINPNR<br>VFKVNTNAYYEMSGLEVSFEELRTFGGH<br>DAKFIDSLQENEFRLYYYNKFKDIASTLN<br>KAKSIVGTTASLQYMKNVFKEKYLLSEDT<br>SGKESVDKLKEDKLYKMLTEIYTEDNEVK<br>FEKVLNRKTYLNEDKAVFKINIVPKVNYTI<br>YDGENLRNTNLAANENGQNTEINNMNFT<br>KLKNFTGLFEFYKLL**S**VRGIITSKTKSLDK<br>GYNKHHHHHH (SEQ ID NO: 17) | 5'-<br>catatgaaggaaacttggtgggaaacttggtggaccgaatggtctcaacca<br>aagaagaagcgcaaggttcaatttgttaataaacaatttaattataaagatcc<br>agtaaatggtgtcgacattgcttatatcaaaattccaaatgtaggccaaatgc<br>aaccagtaaaagcttttaaaattcataataaaatctgggttattccagaacgc<br>gatacctttaccaatccggaagaaggtgatctgaatccaccaccagaagca<br>aaacaagttccagttagctattatgatagcacctatctgagcaccgataatga<br>aaaagataattatctgaagggcgttaccaaactgtttgagcgcatttatagca<br>ctgatctgggtcgcatgctgctgaccagcatcgtacgcggtatcccattttg<br>gggtggtagcaccatcgataccgaactgaaagttattgatactaattgtatta<br>atgtgatccaaccagatggtagctatcgcagcgaagaactgaatctggtaa<br>tcatcggtccgagcgctgatattatccagtagaatgtaaaagctttggtcat<br>gaagttctgaatctgacccgtaatggttatggcagcacccaatacattcgctt<br>tagcccagattttacctaggattgaggagagcctggaagttgataccaatc<br>cgctgctgggtgcaggcaaatttgctaccgatccagcagtaaccctggca<br>catgaactgatacatgctggccatcgcctgtatggtatcgcaattaatccaa<br>atcgcgtttttaaagtaaataccaatgcctattatgaaatgagcggtctggaa<br>gtaagctttgaggaactgcgcacctttggtggtcatgatgcaaagtttatcga<br>tagcctgcaggaaaacgaatttcgtctgtattattataataagtttaaagatat<br>cgcaagcaccctgaataaagctaaaagcatcgtaggtaccaccgctagcc<br>tgcagtatatgaaaaatgtttttaaagagaaatatctgctgtctgaagatacct<br>ctggcaaatttagcgtagataaactgaaatttgataagctgtacaaaatgctg<br>accgagatttacaccgaggataattttgttaagtttttttaaagtactgaaccgc<br>aaaacctatctgaattttgataaagccgtatttaagatcaatatcgtaccgaa<br>ggtaaattacaccatctatgatggttttaatctgcgcaataccaatctggcag<br>caaactttaatggtcaaaataccgaaattaataatatgaattttaccaaactga<br>aaaattttaccggtctgtttgaattctataagctgctg**AGC**gtacgcggtat<br>catcaccagcaaaaccaaaagcctggataaaggctacaataagcatcacc<br>atcaccatcactaataactcgag-3'<br>(SEQ ID NO: 18) |
| PEP1-<br>(ΔM)<br>BTX-L<br>(C430G)-<br>BFGFRP-<br>His | MKETWWETWWTEWSQPKKKRKVQFVN<br>KQFNYKDPVNGVDIAYIKIPNVGQMQPV<br>KAFKIHNKIWVIPERDTFTNPEEGDLNPPP<br>EAKQVPVSYYDSTYLSTDNEKDNYLKGV<br>TKLFERIYSTDLGRMLLTSIVRGIPFWGGS<br>TIDTELKVIDTNCINVIQPDGSYRSEELNL<br>VIIGPSADIIQFECKSFGHEVLNLTRNGYGS<br>TQYIRFSPDFTEGFEESLEVDTNPLLGAGK<br>FATDPAVTLAHELIHAGHRLYGIAINPNR<br>VFKVNTNAYYEMSGLEVSFEELRTFGGH | 5'-<br>catatgaaggaaacttggtgggaaacttggtggaccgaatggtctcaacca<br>aagaagaagcgcaaggttcaatttgttaataaacaatttaattataaagatcc<br>agtaaatggtgtcgacattgcttatatcaaaattccaaatgtaggccaaatgc<br>aaccagtaaaagcttttaaaattcataataaaatctgggttattccagaacgc<br>gatacctttaccaatccggaagaaggtgatctgaatccaccaccagaagca<br>aaacaagttccagttagctattatgatagcacctatctgagcaccgataatga<br>aaaagataattatctgaagggcgttaccaaactgtttgagcgcatttatagca<br>ctgatctgggtcgcatgctgctgaccagcatcgtacgcggtatcccattttg<br>gggtggtagcaccatcgataccgaactgaaagttattgatactaattgtatta |

TABLE 1-continued

| | Amino acid sequence | Nucleotide sequence |
|---|---|---|
| | DAKFIDSLQENEFRLYYYNKFKDIASTLN<br>KAKSIVGTTASLQYMKNVFKEKYLLSEDT<br>SGKFSVDKLKFDKLYKMLTEIYTEDNFVK<br>FFKVLNRKTYLNFDKAVFKINIVPKVNYTI<br>YDGFNLRNTNLAANFNGQNTEINNMNFT<br>KLKNFTGLFEFYKLL**G**VRGIITSKTKSLDK<br>GYNKTYRSRKYXSWYHHHHHH (SEQ ID NO: 19)<br>(X stands for S or T.) | atgtgatccaaccagatggtagctatcgcagcgaagaactgaatctggtaa<br>tcatcggtccgagcgctgatattatccagtttgaatgtaaaagattggtcat<br>gaagttctgaatctgacccgtaatggttatggcagcacccaatacattcgctt<br>tagcccagattttacctttggattgaggagagcctggaagttgataccaatc<br>cgctgctgggtgcaggcaaatttgctaccgatccagcagtaaccctggca<br>catgaactgatacatgctggccatcgcctgtatggtatcgcaattaatccaa<br>atcgcgtttttaaagtaaataccaatgcctattatgaaatgagcggtctggaa<br>gtaagctttgaggaactgcgcacctttggtggtcatgatgcaaagtttatcga<br>tagcctgcaggaaaacgaatttcgtctgtattattataataagtttaaagatat<br>cgcaagcaccctgaataaagctaaaagcatcgtaggtaccaccgctagcc<br>tgcagtatatgaaaaatgtttttaaagagaaatatctgctgtctgaagatacct<br>ctggcaaatttagcgtagataaactgaaatttgataagctgtacaaaatgctg<br>accgagatttacaccgaggataattttgttaagtttttaaagtactgaaccgc<br>aaaacctatctgaattttgataaagccgtatttaagatcaatatcgtaccgaa<br>ggtaaattacaccatctatgatggttttaatctgcgcaataccaatctggcag<br>caaactttaatggtcaaaataccgaaattaataatatgaattttaccaaactga<br>aaaattttaccggtctgtttgaattctataagctgctg**GGCg**TACGCG<br>GTATCATCACCAGCAAAACCAAAAGCCTGGA<br>TAAAGGCTACAATAAGACCTATCGCAGCCGC<br>AAATAT**ASC**AGCTGGTATCATCACCATCACCA<br>TCACTAATAACTCGAG-3' (SEQ ID NO: 20)<br>(ASC stands for AGC or ACC.) |
| PEP1-<br>(ΔM)<br>BTX-L<br>(C430A)-<br>BFGFRP-<br>His | MKETWWETWWTEWSQPKKKRKVQFVN<br>KQFNYKDPVNGVDIAYIKIPNVGQMQPV<br>KAFKIHNKIWVIPERDTFTNPEEGDLNPPP<br>EAKQVPVSYYDSTYLSTDNEKDNYLKGV<br>TKLFERIYSTDLGRMLLTSIVRGIPFWGGS<br>TIDTELKVIDTNCINVIQPDGSYRSEELNL<br>VIIGPSADIIQFECKSFGHEVLNLTRNGYGS<br>TQYIRFSPDFTFGFEESLEVDTNPLLGAGK<br>FATDPAVTLAHELIHAGHRLYGIAINPNR<br>VFKVNTNAYYEMSGLEVSFEELRTFGGH<br>DAKFIDSLQENEFRLYYYNKFKDIASTLN<br>KAKSIVGTTASLQYMKNVFKEKYLLSEDT<br>SGKFSVDKLKFDKLYKMLTEIYTEDNFVK<br>FFKVLNRKTYLNFDKAVFKINIVPKVNYTI<br>YDGFNLRNTNLAANFNGQNTEINNMNFT<br>KLKNFTGLFEFYKLL**A**VRGIITSKTKSLDK<br>GYNKTYRSRKYXSWYHHHHHH (SEQ ID NO: 21)<br>(X stands for S or T.) | 5'-<br>catatgaaggaaacttggtgggaaacttggtggaccgaatggtctcaacca<br>aagaagaagcgcaaggttcaatttgttaataaacaatttaattataaagatcc<br>agtaaatggtgtcgacattgcttatatcaaaattccaaatgtaggccaaatgc<br>aaccagtaaaagcttttaaaattcataataaaatctgggttattccagaacgc<br>gatacctttaccaatccggaagaaggtgatctgaatccaccaccagaagca<br>aaacaagttccagttagctattatgatagcacctatctgagcaccgataatga<br>aaaagataattatctgaagggcgttaccaaactgtttgagcgcatttatagca<br>ctgatctgggtcgcatgctgctgaccagcatcgtacgcggtatcccattttg<br>gggtggtagcaccatcgataccgaactgaaagttattgatactaattgtatta<br>atgtgatccaaccagatggtagctatcgcagcgaagaactgaatctggtaa<br>tcatcggtccgagcgctgatattatccagtttgaatgtaaaagattggtcat<br>gaagttctgaatctgacccgtaatggttatggcagcacccaatacattcgctt<br>tagcccagattttacctttggattgaggagagcctggaagttgataccaatc<br>cgctgctgggtgcaggcaaatttgctaccgatccagcagtaaccctggca<br>catgaactgatacatgctggccatcgcctgtatggtatcgcaattaatccaa<br>atcgcgtttttaaagtaaataccaatgcctattatgaaatgagcggtctggaa<br>gtaagctttgaggaactgcgcacctttggtggtcatgatgcaaagtttatcga<br>tagcctgcaggaaaacgaatttcgtctgtattattataataagtttaaagatat<br>cgcaagcaccctgaataaagctaaaagcatcgtaggtaccaccgctagcc<br>tgcagtatatgaaaaatgtttttaaagagaaatatctgctgtctgaagatacct<br>ctggcaaatttagcgtagataaactgaaatttgataagctgtacaaaatgctg<br>accgagatttacaccgaggataattttgttaagtttttaaagtactgaaccgc<br>aaaacctatctgaattttgataaagccgtatttaagatcaatatcgtaccgaa<br>ggtaaattacaccatctatgatggttttaatctgcgcaataccaatctggcag<br>caaactttaatggtcaaaataccgaaattaataatatgaattttaccaaactga<br>aaaattttaccggtctgtttgaattctataagctgctg**GCG**gTACGCG<br>GTATCATCACCAGCAAAACCAAAAGCCTGGA<br>TAAAGGCTACAATAAGACCTATCGCAGCCGC<br>AAATAT**ASC**AGCTGGTATCATCACCATCACCA<br>TCACTAATAACTCGAG-3' (SEQ ID NO: 22)<br>(ASC stands for AGC or ACC.) |
| PEP1-<br>(AM)<br>BTX-L<br>(C430S)-<br>BFGFRP-<br>His | MKETWWETWWTEWSQPKKKRKVQFVN<br>KQFNYKDPVNGVDIAYIKIPNVGQMQPV<br>KAFKIHNKIWVIPERDTFTNPEEGDLNPPP<br>EAKQVPVSYYDSTYLSTDNEKDNYLKGV<br>TKLFERIYSTDLGRMLLTSIVRGIPFWGGS<br>TIDTELKVIDTNCINVIQPDGSYRSEELNL<br>VIIGPSADIIQFECKSFGHEVLNLTRNGYGS<br>TQYIRFSPDFTFGFEESLEVDTNPLLGAGK<br>FATDPAVTLAHELIHAGHRLYGIAINPNR<br>VFKVNTNAYYEMSGLEVSFEELRTFGGH<br>DAKFIDSLQENEFRLYYYNKFKDIASTLN<br>KAKSIVGTTASLQYMKNVFKEKYLLSEDT<br>SGKFSVDKLKFDKLYKMLTEIYTEDNFVK<br>FFKVLNRKTYLNFDKAVFKINIVPKVNYTI<br>YDGFNLRNTNLAANFNGQNTEINNMNFT<br>KLKNFTGLFEFYKLL**S**VRGIITSKTKSLDK<br>GYNKTYRSRKYXSWYHHHHHH (SEQ ID NO: 23)<br>(X stands for S or T.) | 5'-<br>catatgaaggaaacttggtgggaaacttggtggaccgaatggtctcaacca<br>aagaagaagcgcaaggttcaatttgttaataaacaatttaattataaagatcc<br>agtaaatggtgtcgacattgcttatatcaaaattccaaatgtaggccaaatgc<br>aaccagtaaaagcttttaaaattcataataaaatctgggttattccagaacgc<br>gatacctttaccaatccggaagaaggtgatctgaatccaccaccagaagca<br>aaacaagttccagttagctattatgatagcacctatctgagcaccgataatga<br>aaaagataattatctgaagggcgttaccaaactgtttgagcgcatttatagca<br>ctgatctgggtcgcatgctgctgaccagcatcgtacgcggtatcccattttg<br>gggtggtagcaccatcgataccgaactgaaagttattgatactaattgtatta<br>atgtgatccaaccagatggtagctatcgcagcgaagaactgaatctggtaa<br>tcatcggtccgagcgctgatattatccagtttgaatgtaaaagattggtcat<br>gaagttctgaatctgacccgtaatggttatggcagcacccaatacattcgctt<br>tagcccagattttacctttggattgaggagagcctggaagttgataccaatc<br>cgctgctgggtgcaggcaaatttgctaccgatccagcagtaaccctggca<br>catgaactgatacatgctggccatcgcctgtatggtatcgcaattaatccaa<br>atcgcgtttttaaagtaaataccaatgcctattatgaaatgagcggtctggaa<br>gtaagctttgaggaactgcgcacctttggtggtcatgatgcaaagtttatcga<br>tagcctgcaggaaaacgaatttcgtctgtattattataataagtttaaagatat<br>cgcaagcaccctgaataaagctaaaagcatcgtaggtaccaccgctagcc<br>tgcagtatatgaaaaatgtttttaaagagaaatatctgctgtctgaagatacct<br>ctggcaaatttagcgtagataaactgaaatttgataagctgtacaaaatgctg |

TABLE 1-continued

| | Amino acid sequence | Nucleotide sequence |
|---|---|---|
| | | accgagatttacaccgaggataattttgttaagtttttaaagtactgaaccgc<br>aaaacctatctgaattttgataaagccgtatttaagatcaatatcgtaccgaa<br>ggtaaattacaccatctatgatggttttaatctgcgcaataccaatctggcag<br>caaactttaatggtcaaaataccgaaattaataatatgaattttaccaaactga<br>aaaattttaccggtctgtttgaattctataagctgctg**AGCg**TACGCG<br>GTATCATCACCAGCAAAACCAAAAGCCTGGA<br>TAAAGGCTACAATAAGACCTATCGCAGCCGC<br>AAATAT**ASC**AGCTGGTATCATCACCATCACCA<br>TCACTAATAACTCGAG-3' (SEQ ID NO: 24)<br>(ASC stands for AGC or ACC.) |
| Linker | GGGG (SEQ ID NO: 25) | GGTGGTGGTGGT (SEQ ID NO: 26) |
| Cleavage Peptide | LVPRGS (SEQ ID NO: 27) | CTGGTACCACGCGGTAGC (SEQ ID NO: 28) |
| BTX-L (C430G) | MQFVNKQFNYKDPVNGVDIAYIKIPNVG<br>QMQPVKAFKIHNKIWVIPERDTFTNPEEG<br>DLNPPPEAKQVPVSYYDSTYLSTDNEKDN<br>YLKGVTKLFERIYSTDLGRMLLTSIVRGIP<br>FWGGSTIDTELKVIDTNCINVIQPDGSYRS<br>EELNLVIIGPSADIIQFECKSFGHEVLNLTR<br>NGYGSTQYIRFSPDFTEGFEESLEVDTNPL<br>LGAGKFATDPAVTLAHELIHAGHRLYGIA<br>INPNRVFKVNTNAYYEMSGLEVSFEELRT<br>FGGHDAKFIDSLQENEFRLYYYNKFKDIA<br>STLNKAKSIVGTTASLQYMKNVFKEKYLL<br>SEDTSGKESVDKLKEDKLYKMLTEIYTED<br>NFVKFFKVLNRKTYLNFDKAVFKINIVPK<br>VNYTIYDGFNLRNTNLAANFNGQNTEINN<br>MNFTKLKNFTGLFEFYKLL**G**VRGIITSKT<br>KSLDKGYNK<br>(SEQ ID NO: 29) | 5'-<br>atgcaatttgttaataaacaatttaattataaagatccagtaaatggtgtcgac<br>attgcttatatcaaaattccaaatgtaggccaaatgcaaccagtaaaagcttt<br>taaaattcataataaaatctgggttattccagaacgcgatacctttaccaatcc<br>ggaagaaggtgatctgaatccaccaccagaagcaaaacaagttccagtta<br>gctattatgatagcacctatctgagcaccgataatgaaaaagataattatctg<br>aagggcgttaccaaactgtttgagcgcatttatagcactgatctgggtcgca<br>tgctgctgaccagcatcgtacgcggtatcccattttggggtggtagcaccat<br>cgataccgaactgaaagttattgatactaattgtattaatgtgatccaaccag<br>atggtagctatcgcagcgaagaactgaatctggtaatcatcggtccgagcg<br>ctgatattatccagtttgaatgtaaaagctttggtcatgaagttctgaatctga<br>cccgtaatggttatggcagcacccaatacattcgctttagcccagattttacc<br>tttggttttgaggagagcctggaagttgataccaatccgctgctgggtgcag<br>gcaaatttgctaccgatccagcagtaaccctggcacatgaactgatacatg<br>ctggccatcgcctgtatggtatcgcaattaatccaaatcgcgtttttaaagta<br>aataccaatgcctattatgaaatgagcggtctggaagtaagctttgaggaac<br>tgcgcacctttggtggtcatgatgcaaagtttatcgatagcctgcaggaaaa<br>cgaatttcgtctgtattattataataagtttaaagatatcgcaagcaccctgaa<br>taaagctaaaagcatcgtaggtaccaccgctagcctgcagtatatgaaaaa<br>tgtttttaaagagaaatatctgctgtctgaagatacctctggcaaatttagcgt<br>agataaactgaaatttgataagctgtacaaaatgctgaccgagatttacacc<br>gaggataattttgttaagtttttaaagtactgaaccgcaaaacctatctgaatt<br>ttgataaagccgtatttaagatcaatatcgtaccgaaggtaaattacaccatc<br>tatgatggattaatctgcgcaataccaatctggcagcaaactttaatggtca<br>aaataccgaaattaataatatgaattttaccaaactgaaaaattttaccggtct<br>gtttgaattctataagctgctg**GGC**gtacgcggtatcatcaccagcaaaa<br>ccaaaagcctggataaaggctacaataag-3' (SEQ ID NO: 30) |
| BTX-L (C430A) | MQFVNKQFNYKDPVNGVDIAYIKIPNVG<br>QMQPVKAFKIHNKIWVIPERDTFTNPEEG<br>DLNPPPEAKQVPVSYYDSTYLSTDNEKDN<br>YLKGVTKLFERIYSTDLGRMLLTSIVRGIP<br>FWGGSTIDTELKVIDTNCINVIQPDGSYRS<br>EELNLVIIGPSADIIQFECKSFGHEVLNLTR<br>NGYGSTQYIRFSPDFTFGFEESLEVDTNPL<br>LGAGKFATDPAVTLAHELIHAGHRLYGIA<br>INPNRVFKVNTNAYYEMSGLEVSFEELRT<br>FGGHDAKFIDSLQENEFRLYYYNKFKDIA<br>STLNKAKSIVGTTASLQYMKNVFKEKYLL<br>SEDTSGKFSVDKLKFDKLYKMLTEIYTED<br>NFVKFFKVLNRKTYLNFDKAVFKINIVPK<br>VNYTIYDGFNLRNTNLAANFNGQNTEINN<br>MNFTKLKNFTGLFEFYKLL**A**VRGIITSKTK<br>SLDKGYNK<br>(SEQ ID NO: 31) | 5'-<br>atgcaatttgttaataaacaatttaattataaagatccagtaaatggtgtcgac<br>attgcttatatcaaaattccaaatgtaggccaaatgcaaccagtaaaagcttt<br>taaaattcataataaaatctgggttattccagaacgcgataccataccaatcc<br>ggaagaaggtgatctgaatccaccaccagaagcaaaacaagttccagtta<br>gctattatgatagcacctatctgagcaccgataatgaaaaagataattatctg<br>aagggcgttaccaaactgtttgagcgcatttatagcactgatctgggtcgca<br>tgctgctgaccagcatcgtacgcggtatcccattttggggtggtagcaccat<br>cgataccgaactgaaagttattgatactaattgtattaatgtgatccaaccag<br>atggtagctatcgcagcgaagaactgaatctggtaatcatcggtccgagcg<br>ctgatattatccagtttgaatgtaaaagctttggtcatgaagttctgaatctga<br>cccgtaatggttatggcagcacccaatacattcgctttagcccagattttacc<br>tttggttttgaggagagcctggaagttgataccaatccgctgctgggtgcag<br>gcaaatttgctaccgatccagcagtaaccctggcacatgaactgatacatg<br>ctggccatcgcctgtatggtatcgcaattaatccaaatcgcgtttttaaagta<br>aataccaatgcctattatgaaatgagcggtctggaagtaagctttgaggaac<br>tgcgcacctttggtggtcatgatgcaaagtttatcgatagcctgcaggaaaa<br>cgaatttcgtctgtattattataataagtttaaagatatcgcaagcaccctgaa<br>taaagctaaaagcatcgtaggtaccaccgctagcctgcagtatatgaaaaa<br>tgtttttaaagagaaatatctgctgtctgaagatacctctggcaaatttagcgt<br>agataaactgaaatttgataagctgtacaaaatgctgaccgagatttacacc<br>gaggataattttgttaagtttttaaagtactgaaccgcaaaacctatctgaatt<br>ttgataaagccgtatttaagatcaatatcgtaccgaaggtaaattacaccatc<br>tatgatggattaatctgcgcaataccaatctggcagcaaactttaatggtca<br>aaataccgaaattaataatatgaattttaccaaactgaaaaattttaccggtct<br>gtttgaattctataagctgctg**GCG**gtacgcggtatcatcaccagcaaaa<br>ccaaaagcctggataaaggctacaataag-3'<br>(SEQ ID NO: 32) |
| BTX-L (C430S) | MQFVNKQFNYKDPVNGVDIAYIKIPNVG<br>QMQPVKAFKIHNKIWVIPERDTFTNPEEG<br>DLNPPPEAKQVPVSYYDSTYLSTDNEKDN<br>YLKGVTKLFERIYSTDLGRMLLTSIVRGIP<br>FWGGSTIDTELKVIDTNCINVIQPDGSYRS | 5'-<br>atgcaatttgttaataaacaatttaattataaagatccagtaaatggtgtcgac<br>attgcttatatcaaaattccaaatgtaggccaaatgcaaccagtaaaagcttt<br>taaaattcataataaaatctgggttattccagaacgcgataccataccaatcc<br>ggaagaaggtgatctgaatccaccaccagaagcaaaacaagttccagtta |

TABLE 1-continued

| Amino acid sequence | Nucleotide sequence |
|---|---|
| EELNLVIIGPSADIIQFECKSFGHEVLNLTR<br>NGYGSTQYIRFSPDFTFGFEESLEVDTNPL<br>LGAGKFATDPAVTLAHELIHAGHRLYGIA<br>INPNRVFKVNTNAYYEMSGLEVSFEELRT<br>FGGHDAKFIDSLQENEFRLYYYNKFKDIA<br>STLNKAKSIVGTTASLQYMKNVFKEKYLL<br>SEDTSGKFSVDKLKFDKLYKMLTEIYTED<br>NFVKFFKVLNRKTYLNFDKAVFKINIVPK<br>VNYTIYDGFNLRNTNLAANFNGQNTEINN<br>MNFTKLKNFTGLFEFYKLL**S**VRGIITSKTK<br>SLDKGYNK<br>(SEQ ID NO: 33) | gctattatgatagcacctatctgagcaccgataatgaaaaagataattatctg<br>aagggcgttaccaaactgtttgagcgcatttatagcactgatctgggtcgca<br>tgctgctgaccagcatcgtacgcggtatcccattttggggtggtagcaccat<br>cgataccgaactgaaagttattgatactaattgtattaatgtgatccaaccag<br>atggtagctatcgcagcgaagaactgaatctggtaatcatcggtccgagcg<br>ctgatattatccagtttgaatgtaaaagctttggtcatgaagttctgaatctga<br>cccgtaatggttatggcagcacccaatacattcgctttagcccagattttacc<br>tttggttttgaggagagcctggaagttgataccaatccgctgctgggtgcag<br>gcaaatttgctaccgatccagcagtaaccctggcacatgaactgatacatg<br>ctggccatcgcctgtatggtatcgcaattaatccaaatcgcgtttttaaagta<br>aataccaatgcctattatgaaatgagcggtctggaagtaagctttgaggaac<br>tgcgcacctttggtggtcatgatgcaaagtttatcgatagcctgcaggaaaa<br>cgaatttcgtctgtattattataataagtttaaagatatcgcaagcaccctgaa<br>taaagctaaaagcatcgtaggtaccaccgctagcctgcagtatatgaaaaa<br>tgtttttaaagagaaatatctgctgtctgaagatacctctggcaaatttagcgt<br>agataaactgaaatttgataagctgtacaaaatgctgaccgagatttacacc<br>gaggataattttgttaagtttttaaagtactgaaccgcaaaacctatctgaatt<br>ttgataaagccgtatttaagatcaatatcgtaccgaaggtaaattacaccatc<br>tatgatggattaatctgcgcaataccaatctggcagcaaactttaatggtca<br>aaataccgaaattaataatatgaattttaccaaactgaaaaattttaccggtct<br>gtttgaattctataagctgctg**AGC**gtacgcggtatcatcaccagcaaaa<br>ccaaaagcctggataaaggctacaataag-3'<br>(SEQ ID NO: 34) |

TABLE 2

| Mutation | Sequence |
|---|---|
| C430G | GAATTCTATAAGCTGCTGGGCGTACGCGGTATCATCACCAGCAAAACCAAAAG<br>CCTGGATAAAGGCTACAATAAGCATCACCATCACCATCACTAATAACTCGAG<br>(SEQ ID NO: 35) |
| C430A | GAATTCTATAAGCTGCTGGCGGTACGCCGGTATCATCACCAGCAAAACCAAAAG<br>CCTGGATAAAGGCTACAATAAGCATCACCATCACCATCACTAATAACTCGAG<br>(SEQ ID NO: 36) |
| C430S | GAATTCTATAAGCTGCTGAGCGTACGCGGTATCATCACCAGCAAAACCAAAAG<br>CCTGGATAAAGGCTACAATAAGCATCACCATCACCATCACTAATAACTCGAG<br>(SEQ ID NO: 37) |
| C430G-BFGRP | GAATTCTATAAGCTGCTGGGCGTACGCGGTATCATCACCAGCAAAACCAAAAG<br>CCTGGATAAAGGCTACAATAAGACCTATCGCAGCCGCAAATATASCAGCTGGT<br>ATCATCACCATCACCATCACTAATAACTCGAG-3' (SEQ ID NO: 38)<br>(ASC stands for AGC or ACC.) |
| C430A-BFGRP | GAATTCTATAAGCTGCTGGCGGTACGCGGTATCATCACCAGCAAAACCAAAAG<br>CCTGGATAAAGGCTACAATAAGACCTATCGCAGCCGCAAATATASCAGCTGGT<br>ATCATCACCATCACCATCACTAATAACTCGAG-3' (SEQ ID NO: 39)<br>(ASC stands for AGC or ACC.) |
| C430S-BFGRP | GAATTCTATAAGCTGCTGAGCGTACGCGGTATCATCACCAGCAAAACCAAAAG<br>CCTGGATAAAGGCTACAATAAGACCTATCGCAGCCGCAAATATASCAGCTGGT<br>ATCATCACCATCACCATCACTAATAACTCGAG-3' (SEQ ID NO: 40)<br>(ASC stands for AGC or ACC.) |
| Belt | GAATTCTATAAGCTGCTGTGTGTACGCGGTATCATCACCAGCAAAACCAAAAGCCT<br>GGATAAAGGCTACAATAAGGCGCTGAACGATCTGTGCCATCACCATCACCATCAC<br>TAATAACTCGAG (SEQ ID NO: 41) |

Example 2. Expression of Non-Toxic Protease in *E. coli*

Each of the expression vectors for *E. coli* constructed in Example 1 was transformed into an *E. coli* BL21 (DE3) strain as a host for gene expression to construct recombinant *E. coli* strains. LB culture medium was inoculated with the ampicillin-resistant colonies and culturing was performed with shaking at 37° C. When the absorbance at 600 nm reached 0.6 to 0.7, 0.5 mM IPTG was added to the culture medium, and then expression of the non-toxic protease was induced at 18 to 25° C. depending on the conditions. Next, the cells were cultured for 6 to 12 hours, and recombinant *E. coli* cells were harvested by centrifugation (at 3,000 rpm for 20 minutes).

The harvested *E. coli* cells were suspended in a 25% sucrose solution (containing 50 mM Tris HCl, pH 7.8, 0.1 mM EDTA), and 0.2 mg/ml of lysozyme was added thereto, followed by incubation at 4° C. for 1.5 hours. Next, a 1.5-fold volume of lysis buffer (20 mM Tris HCl, pH7.8, 0.2 M NaCl, 1% DCA, 1.6% NP-40 (or 1% SDS), 2 mM EDTA, 0.5 mM DTT) was added to the suspension, and then the cells were lysed using ultrasound at 4° C. The protein was quantified and loaded on SDS-PAGE gel, followed by Coomassie blue staining.

Figure 7:
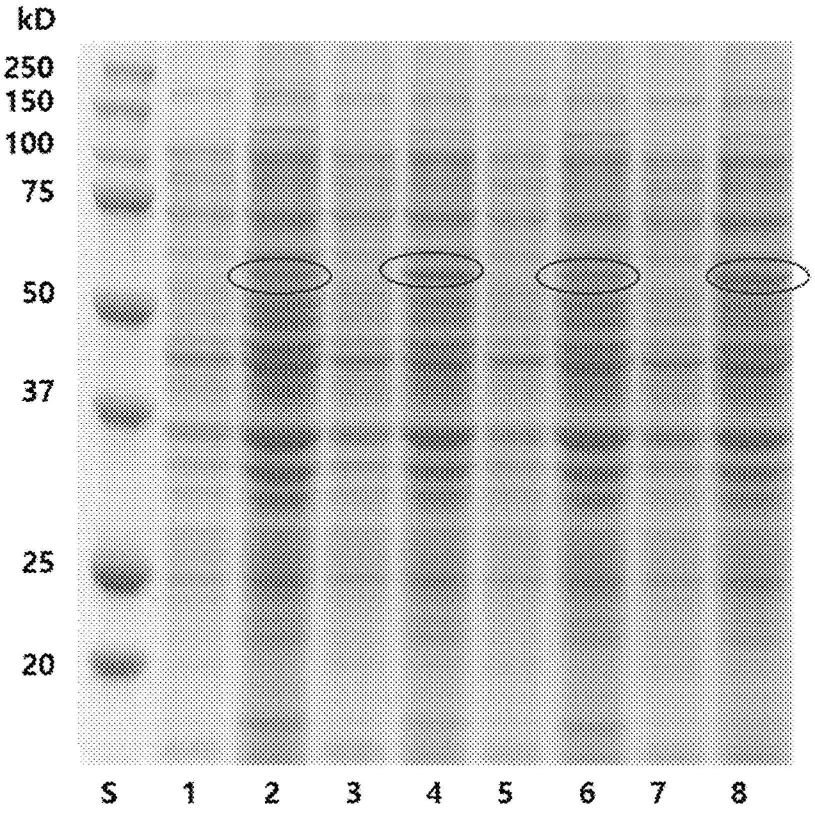
FIG. 7 shows the results of analyzing the expression patterns of mutated non-toxic proteases according to various embodiments of the present invention in *E. coli* by Coomassie blue staining.
Figure 8:
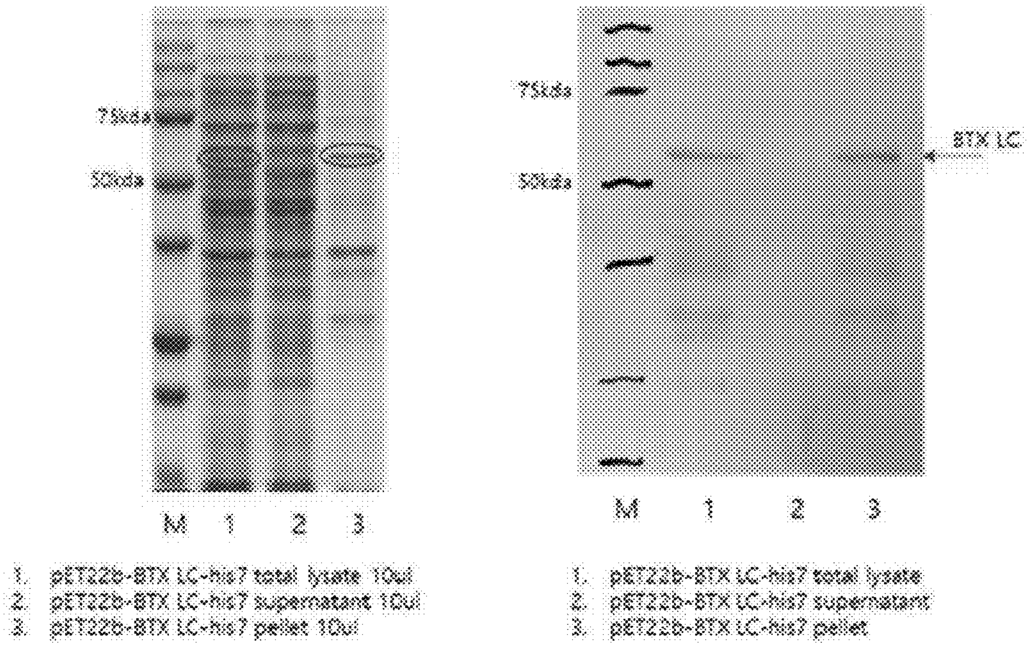
FIG. 8 shows the results of expressing a wild-type non-toxic protease in *E. coli* and analyzing the expression patterns thereof in the supernatant and precipitate by Coomassie blue staining and Western blotting.
Figure 9:
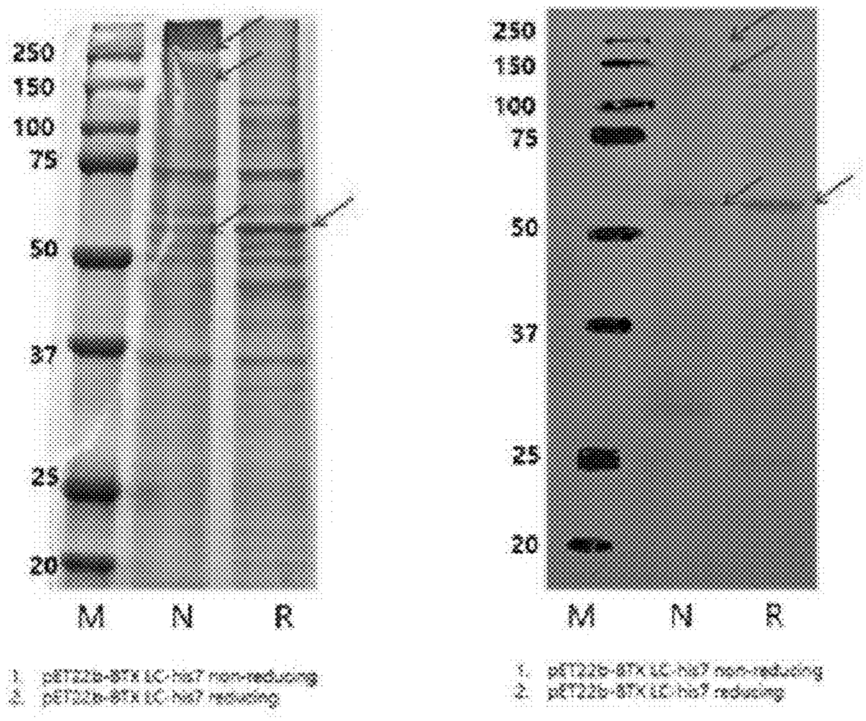
FIG. 9 shows the results of expressing a wild-type non-toxic protease in *E. coli* and analyzing the aggregation patterns of the wild-type non-toxic protease under non-reducing and reducing conditions by Coomassie blue staining and Western blotting.
Figure 12:
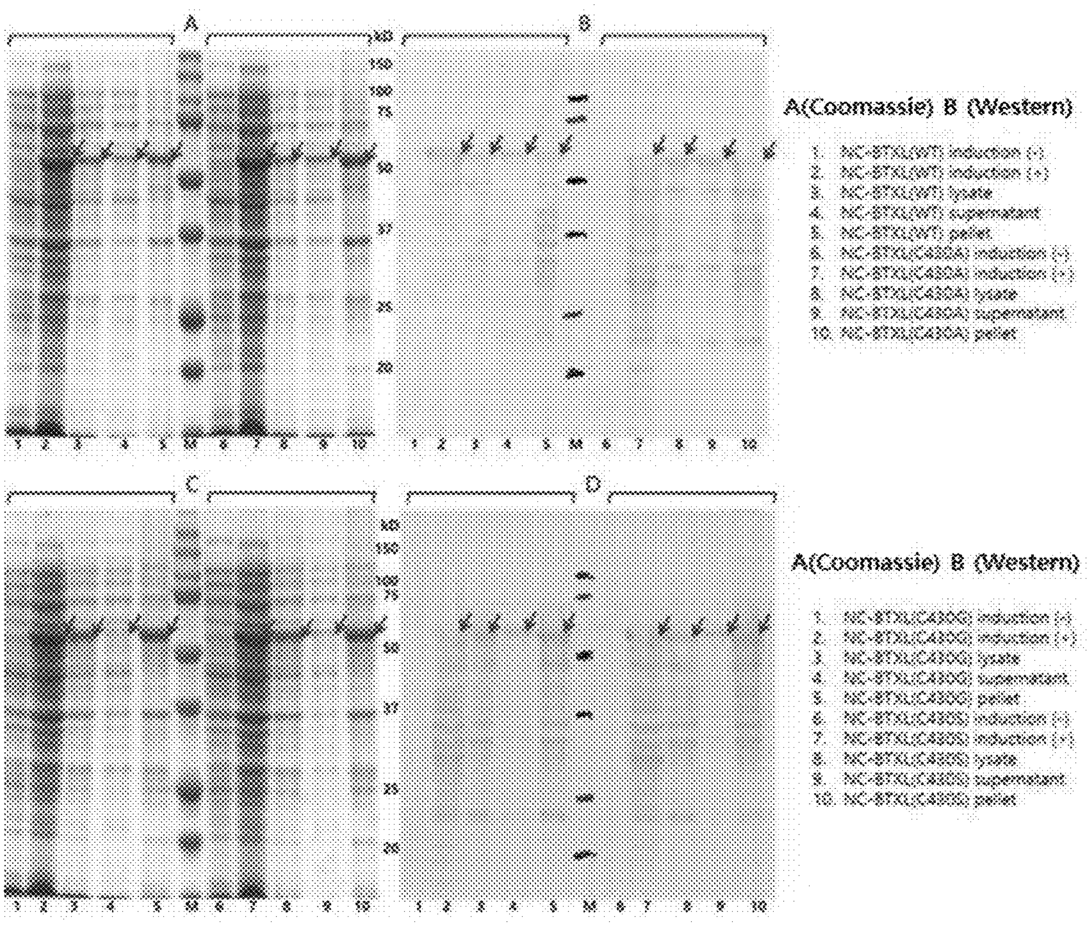
FIG. 12 shows the results of lysing *E. coli* cells expressing the mutated non-toxic proteases according to various embodiments of the present invention, separating the cell lysate into a soluble fraction and an insoluble fraction, and then analyzing the amount of a non-toxic protease in each fraction by Coomassie blue staining and Western blotting.
Figure 13:
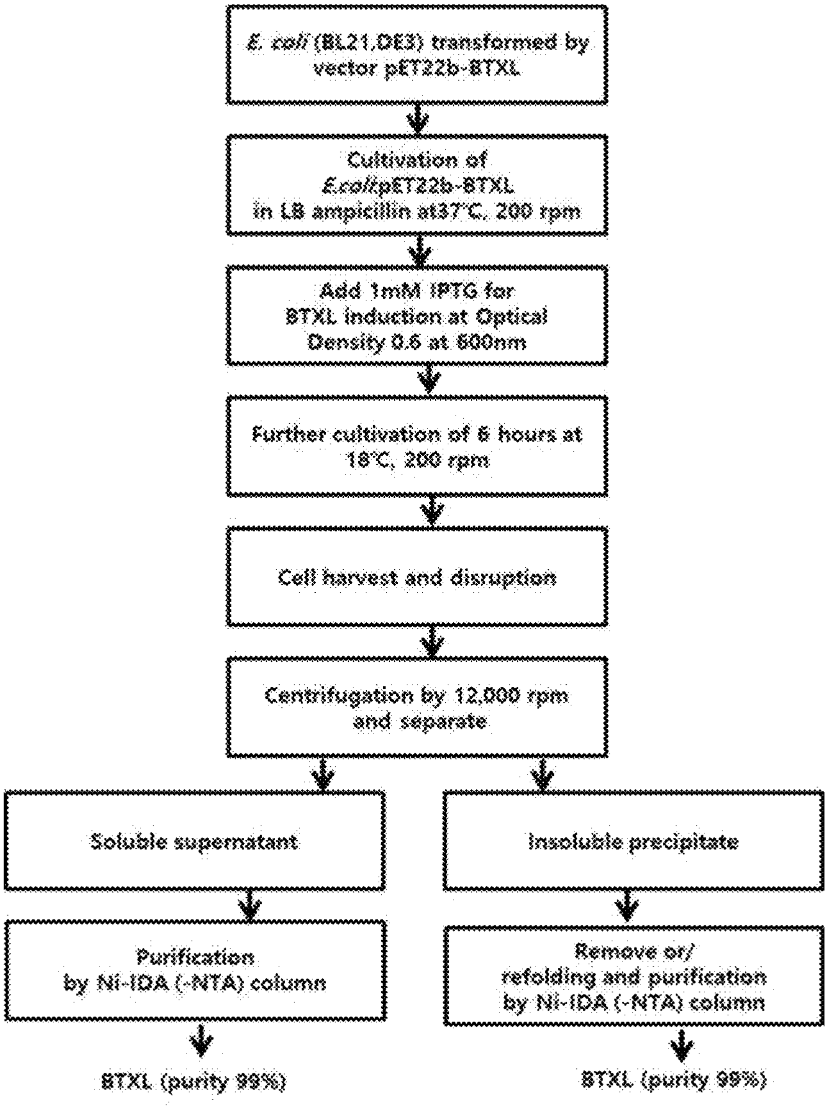
FIG. 13 is a schematic diagram showing a production process according to the present invention.

As a result, as shown in FIG. 7, it could be confirmed that the wild-type and mutated non-toxic proteases were effectively expressed by induction with IPTG. As shown in FIG. 8, it was confirmed that the non-toxic protease appeared only in the total cell lysate and the pellet, suggesting that it was mostly present in an insoluble form. In addition, as a result of subjecting the wild-type non-toxic protease to SDS-PAGE under non-reducing conditions and reducing conditions, it could be confirmed that the wild-type non-toxic protease existed in the form of high-molecular-weight protease under the non-reducing conditions, suggesting that disulfide bonds affect the formation of aggregates of the wild-type non-toxic protease (FIG. 9). Meanwhile, when the wild-type and mutated non-toxic proteases were codon-optimized to be suitable for expression in *E. coli*, the expression levels thereof could be significantly increased (FIGS. 10 and 11).

Example 3. Purification of Non-Toxic Protease

To purify the non-toxic proteases, each of the recombinant *E. coli* strains was cultured according to the method of Example 2, and then the *E. coli* cells were harvested by centrifugation (at 3,000 rpm for 20 minutes). 1 g of the harvested cells were suspended in a cell suspending solution (50 mM Tris HCl, pH 7.8, 0.1 mM EDTA, 25% sucrose), and 0.2 mg/ml of lysozyme was added thereto, followed by incubation at 4° C. for 1.5 hours. Then, a 1.5-fold volume (3 ml) of lysis buffer (20 mM Tris HCl, pH 7.8, 0.2 M NaCl, 1% DCA, 1.6% NP-40 (or 1% SDS), 2 mM EDTA, 0.5 mM DTT) was added to the suspension, and the cells were disrupted using an ultrasonic disruptor until the viscosity of the cell lysate disappeared when viewed with the naked eye. The cell lysate was separated into a soluble fraction and an insoluble fraction by centrifugation at 12,000 rpm and 4° C. for 15 minutes.

As a result of observing the fractions by Coomassie blue staining or Western blotting after SDS-PAGE, it was confirmed that a significant portion of each of the wild-type and mutated non-toxic proteases was present in the insoluble fractions.

The non-toxic protease present in the soluble fraction was loaded onto a $Ni^{2+}$-IDA affinity column (iminodiacetic acid). The column was washed with a 10-fold volume of binding buffer (50 mM potassium phosphate buffer (pH 8.0)+300 mM NaCl+1 mM PMSF+1 mM β-mercaptoethanol) and a 6-fold volume of washing buffer (50 mM potassium phosphate buffer (pH 8.0)+300 mM NaCl+1 mM PMSF+1 mM β-mercaptoethanol+10 mM imidazole), and then eluted stepwise with elution buffers (50 mM potassium phosphate buffer (pH 8.0)+300 mM NaCl+1 mM PMSF+1 mM β-mercaptoethanol) containing 200, 300 or 500 mM imidazole.

Meanwhile, after the soluble fraction was isolated, the non-toxic protease precipitate of the insoluble fraction was washed three times with 5 ml of the same volume as the supernatant (washing buffer, 2 to 4 M urea, 0.5% Triton X100, mM EDTA, 1 mM DTT) and the supernatant was removed. Meanwhile, after the soluble fraction was isolated, the non-toxic protease precipitate of the insoluble fraction was washed three times with 5 ml (the same volume as that of the supernatant) of washing buffer (2 to 4 M urea, 0.5% Triton X100, 1 mM EDTA, 1 mM DTT), and then the supernatant was removed. The recovered precipitate was denatured with 1 ml of urea solution (8 M urea, 20 mM Tris HCl, pH 7.8, 20 μM DTT), and then transferred to a dialysis membrane (molecular weight cutoff: 12,000, Sigma, cat no: D-0530, USA) and subjected to refolding by dialysis three times with a volume 100 times the volume of the urea solution of dialysis buffer (0.08 mM NaCl, 20 mM Tris HCl, pH 7.8, 0.03% tween 20), and 10 to 20 μM $ZnCl_2$ was added thereto as needed. The resulting material was loaded onto a $Ni^{2+}$-IDA affinity column (iminodiacetic acid), and the column was washed stepwise with a 10-fold volume of binding buffer (50 mM potassium phosphate buffer (pH 8.0)+300 mM NaCl+1 mM PMSF+1 mM β-mercaptoethanol) and a 6-fold volume of washing buffer (50 mM potassium phosphate buffer (pH 8.0)+300 mM NaCl+1 mM PMSF+1 mM β-mercaptoethanol+10 mM imidazole), and then eluted stepwise with elution buffers (50 mM potassium phosphate buffer (pH 8.0)+300 mM NaCl+1 mM PMSF+1 mM β-mercaptoethanol) containing each of 200, 300 and 500 mM imidazole. The fractions were combined and desalted with a PD-10 column (GE Healthcare, USA). Protein concentration was measured by BCA protein assay using bovine serum albumin as a standard.

As a result, as shown in FIG. 14, it could be confirmed that the wild-type and mutated non-toxic proteases and fusion non-toxic proteases were effectively purified.

Example 4. Analysis of Folding/Refolding Efficiencies of Non-Toxic Proteases

Figure 15:
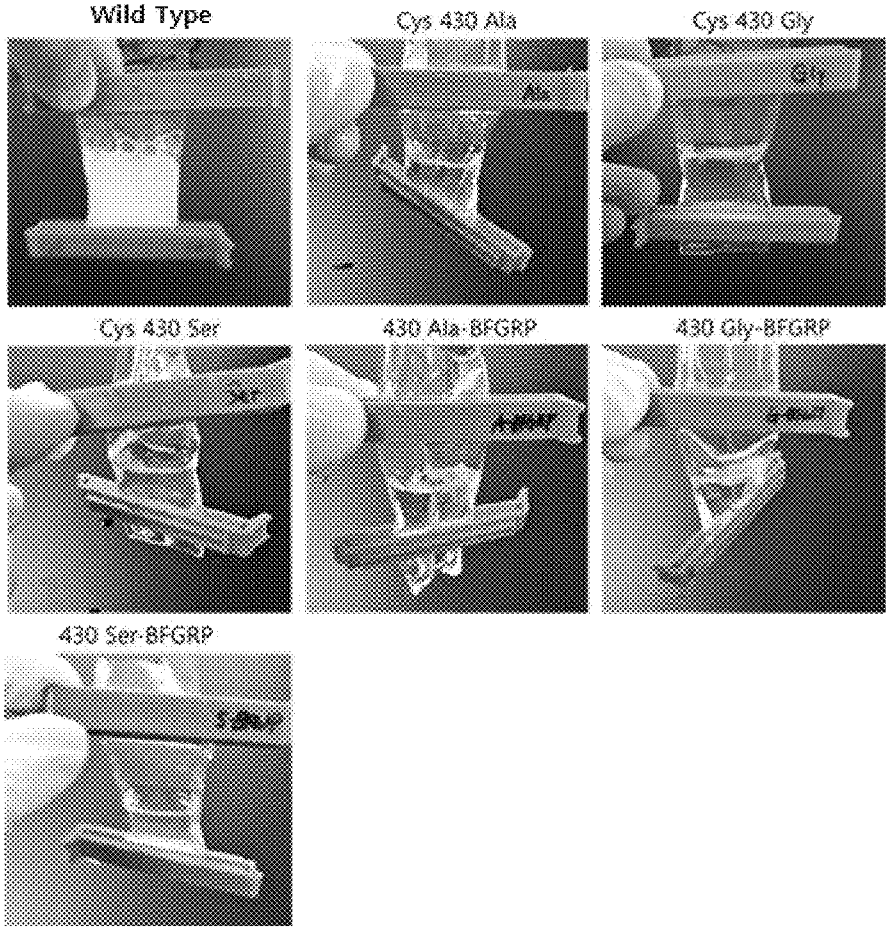
FIG. 15 shows the results of confirming the excellent refolding effects of the mutated non-toxic proteases and fusion non-toxic proteases according to various embodiments of the present invention.

As a result of performing the purification and refolding process on the insoluble fraction in Example 3, as shown in FIG. 15, it was confirmed that, in the case of the wild-type protease, aggregation still appeared after the refolding performed by dialysis, but in the case of the mutated non-toxic protease or the mutated fusion non-toxic protease, aggregation hardly appeared after refolding.

Meanwhile, after centrifugation at 12,000 rpm for 15 minutes, the content (%) of the non-toxic protease in each of the soluble fraction and the insoluble fraction (pellet fraction, aggregation) was analyzed by Coomassie blue staining after SDS-PAGE. As a result, as shown in FIG. 16, it was confirmed that about 60 to 90% of each of the wild-type and mutated non-toxic proteases was present in the insoluble fraction, suggesting that each of the non-toxic proteases was mostly present in the insoluble fraction rather than the soluble fraction. However, the tendency of the non-toxic-protease to be recovered through the refolding process was completely different between the wild-type non-toxic protease and the mutated non-toxic protease. That is, the wild-type non-toxic-protease was mostly present in a precipitated inclusion body state even after the refolding process, and thus was impossible to recover, whereas almost all of the mutated non-toxic-protease could be refolded and recovered.

Example 5. Analysis of Enzymatic Activity of Non-Toxic Protease

Figure 17:
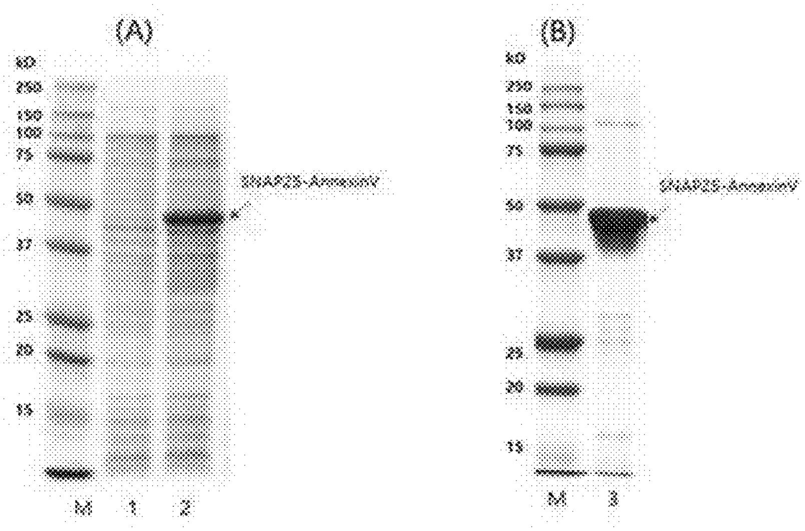
FIG. 17 shows the results of fusing an enzyme active substrate of a non-toxic protease with ANNEXIN V, expressing and purifying the fusion non-toxic protease in *E. coli*, and performing Coomassie blue staining, in order to analyze the cleavage activities of the mutated non-toxic protease and fusion non-toxic protease according to the present invention.

In order to analyze the enzymatic activities of the non-toxic proteases and variants thereof according to the present invention, a substrate for analyzing the cleavage by the non-toxic protease was synthesized. As the substrate, the ANNEXIN V protein fused to the C-terminus of SNAP25 was used for expression (Table 3), and a nucleotide sequence encoding the SNAP25-ANNEXIN V fusion protein was cloned into a pET22b (+) expression vector which was then transformed into an *E. coli* BL21 (DE3) strain. The transformed *E. coli* strain was cultured with shaking in LB medium at 37° C., and when it reached an $O.D_{600}$ of 0.6 to 0.7, 0.5 to 1 mM IPTG was added thereto, and the strain was cultured for 6 hours to induce protein expression. After the cells were disrupted with an ultrasonic disruptor, only the soluble fraction (supernatant) was recovered and purification was performed using his-6 tag contained in SNAP25-ANNEXIN V in a manner similar to the method of Example 3. As a result, as shown in FIG. 17, it was confirmed that SNAP25-ANNEXIN V was effectively expressed and purified.

In order to confirm whether all of the non-toxic proteases purified according to the present invention retain the same enzymatic activity as the wild-type non-toxic protease, cleavage of the purified non-toxic proteases was tested using the purified SANP25-ANNEXIN V as a substrate. To this end, the prepared SNAP25-ANNEXiN V and the non-toxic protease were mixed together at a ratio of 20:1 (w/w) (substrate (SNAP25-ANNEXINV): enzyme (protease)) in an enzymatic reaction solution (100 mM HEPES pH 7.4, 1 mM NaCl, 20 μM $ZnCl_2$, mM DTT 2) and subjected to enzymatic reaction at 37° C. for 5 hours. As a result of analyzing the samples after completion of the reaction, it was confirmed that all of the non-toxic proteases according to the present invention cleaved 50-kDa SNAP25-ANNEXiN V to form 36-kDa and 14-kDa protein bands. This demonstrated that the mutated non-toxic proteases with improved productivity maintained their enzyme activity without changes.

TABLE 3

| | Amino acid sequence | Nucleotide sequence |
|---|---|---|
| His-SNAP25-ANNEXIN V | MGGSHHHHHHENLYFQGSGGNKLKSSD AYKKAWGNNQDGVVASQPARVVDERE QMAISGGFIRRVTNDARENEMDENLEQV SGIIGNLRHMALDMGNEIDTQNRQIDRIM EKADSNKTRIDEANQRATKMLGSGAQV LRGTVTDFPGFDERADAETLRKAMKGL GTDEESILTLLTSRSNAQRQEISAAFKTLF GRDLLDDLKSELTGKFEKLIVALMKPSR LYDAYELKHALKGAGTNEKVLTEIIASR TPEELRAIKQVYEEEYGSSLEDDVVGDTS GYYQRMLVVLLQANRDPDAGIDEAQVE QDAQALFQAGELKWGTDEEKFITIFGTRS VSHLRKVEDKYMTISGFQIEETIDRETSG NLEQLLLAVVKSIRSIPAYLAETLYYAMK GAGTDDHTLIRVMVSRSEIDLENIRKEFR KNFATSLYSMIKGDTSGDYKKALLLLCG EDD (SEQ ID NO: 42) | 5'-catATGGGCGGCAGCCATCATCATCATCA TCATGAAAACCTGTATTTTCAGGGCTCT GGCGGCAACAAGCTGAAATCTAGCGAT GCTTACAAAAAAGCCTGGGGCAATAATC AGGACGGCGTGGTGGCCAGCCAGCCTGC TCGTGTAGTGGACGAACGTGAGCAGATG GCCATCAGCGGCGGCTTCATCCGTCGTG TAACCAATGATGCCCGTGAAAATGAAAT GGATGAAAACCTGGAGCAGGTGAGCGG CATCATCGGCAACCTGCGTCACATGGCC CTGGATATGGGCAATGAGATCGATACCC AGAATCGTCAGATCGACCGTATCATGGA GAAGGCTGATTCCAACAAAACCCGTATC GATGAGGCCAACCAACGTGCAACCAAG ATGCTGGGCAGCGGCGCACAGGTTCTGC GTGGCACTGTGACCGACTTCCCTGGCTT TGATGAGCGTGCTGATGCAGAAACCCTG CGTAAGGCTATGAAAGGCCTGGGCACCG ATGAGGAGAGCATCCTGACCCTGCTGAC CTCCCGTAGCAATGCTCAGCGTCAGGAA ATCTCTGCAGCTTTTAAGACCCTGTTTGG CCGTGATCTGCTGGATGACCTGAAATCC GAACTGACCGGCAAATTTGAAAAACTGA TCGTGGCTCTGATGAAACCTTCTCGTCTG TATGATGCTTATGAACTGAAACATGCCC TGAAGGGCGCTGGCACCAATGAAAAAG TACTGACCGAAATCATTGCTTCTCGTAC CCCTGAAGAACTGCGTGCCATCAAACAA GTTTATGAAGAAGAATATGGCTCTAGCC TGGAAGATGACGTGGTGGGCGACACTTC TGGCTACTACCAGCGTATGCTGGTGGTT CTGCTGCAGGCTAACCGTGACCCTGATG CTGGCATCGATGAAGCTCAAGTTGAACA AGATGCTCAGGCTCTGTTTCAGGCTGGC GAACTGAAATGGGGCACCGATGAAGAA AAGTTTATCACCATCTTTGGCACCCGTA GCGTGTCTCATCTGAGAAAGGTGTTTGA CAAGTACATGACCATCTCTGGCTTTCAA ATCGAGGAAACCATCGACCGTGAGACTT CTGGCAATCTGGAGCAACTGCTGCTGGC TGTTGTGAAATCTATCCGTAGCATCCCT GCCTACCTGGCAGAGACCCTGTATTATG CTATGAAGGGCGCTGGCACCGATGATCA TACCCTGATCCGTGTCATGGTTTCCCGTA GCGAGATCGATCTGTTTAACATCCGTAA GGAGTTTCGTAAGAATTTTGCCACCTCT CTGTATTCCATGATCAAGGGCGATACCT CTGGCGACTATAAGAAAGCTCTGCTGCT GCTGTGTGGCGAAGATGACTAActcgag-3' (SEQ ID NO: 43) |

Example 6. EXPRESSION OF NON-TOXIC PROTEASE IN YEAST

In another embodiment, to express a non-toxic protease in yeast, the sequence shown in Table 4 below was subcloned by restriction enzymes (BamHI and NotI) downstream of the AOX1 promoter of pPIC9. Meanwhile, his 6-tag was introduced for purification of the non-toxic protease, and a TEV cleavage enzyme peptide sequence was added in order to remove his 6-tag after purification, thereby constructing a vector for expression in *Pichia pastoris*.

A *Pichia pastoris* strain was transformed with the vector and cultured in histidine-deficient medium. Then, the formed colonies were cultured in the methanol-assimilating yeast medium BM (buffered minimal medium: 100 mM potassium phosphate, pH 6.0 1.34% yeast nitrogen base, $4\times10^{-5}$% biotin) by supplying glycerol (1%) as a carbon source, and then the carbon source was replaced with methanol (0.5%), thus inducing expression of the non-toxic protease. The culture medium was recovered, and the expressed non-toxic protease was purified therefrom using His-Tag and subjected to Western blotting with a botulinum light-chain antibody (cat no. PA5-48053 (ThermoFisher Scientific, USA). Meanwhile, since a non-toxic protease with an increased molecular weight due to glycosylation is expressed in yeast, the non-target protease was aglycosylated by reaction with the enzyme PNGaseF (cat no. P0704S, New England Bio Lab USA), which cuts sugar chains from the protein, according to the manufacturer's instructions. Then, the non-target protease was subjected to SDS-PAGE and then to Western blotting with a botulinum light-chain antibody.

Figure 19:
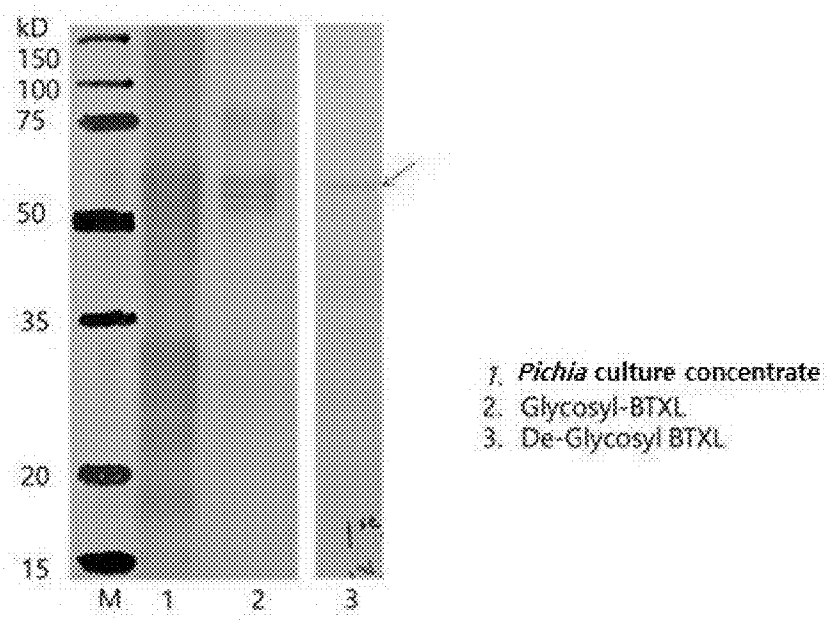
FIG. 19 shows the results of expressing and purifying the fusion non-toxic protease in the recombinant yeast *Pichia pastoris* transformed with the fusion non-toxic protease according to the present invention, and analyzing the fusion non-toxic protease by Western blotting.

As a result, as shown in FIG. 19, it was confirmed that the non-toxic protease was effectively expressed in and purified from the yeast, and a multi-band, non-toxic protease with increased molecular weight due to glycosylation was identified in the yeast, and a single band of the non-toxic protease was observed after aglycosylation.

TABLE 4

| | Amino acid sequence | Nucleotide sequence |
|---|---|---|
| SMF-(ΔM)BTX-L-PEP1-TEV-His | MRFPSIFTAVLFAASSALAAPVNTTTED<br>ETAQIPAEAVIGYSDLEGDFDVAVLPFS<br>NSTNNGLLFINTTIASIAAKEEGVSLEK<br>RQFVNKQFNYKDPVNGVDIAYIKIPNV<br>GQMQPVKAFKIHNKIWVIPERDTFTNP<br>EEGDLNPPPEAKQVPVSYYDSTYLSTD<br>NEKDNYLKGVTKLFERIYSTDLGRMLL<br>TSIVRGIPFWGGSTIDTELKVIDTNCINV<br>IQPDGSYRSEELNLVIIGPSADIIQFECKS<br>FGHEVLNLTRNGYGSTQYIRFSPDFTEG<br>FEESLEVDTNPLLGAGKFATDPAVTLA<br>HELIHAGHRLYGIAINPNRVFKVNTNA<br>YYEMSGLEVSFEELRTFGGHDAKFIDS<br>LQENEFRLYYYNKFKDIASTLNKAKSI<br>VGTTASLQYMKNVFKEKYLLSEDTSG<br>KFSVDKLKFDKLYKMLTEIYTEDNFVK<br>FFKVLNRKTYLNFDKAVFKINIVPKVN<br>YTIYDGFNLRNTNLAANFNGQNTEINN<br>MNFTKLKNFTGLFEFYKLLCVRGIITSK<br>TKSLDKGYNKKETWWETWWTEW<br>SQPKKKRKVENLYFQSNHHHHHH<br>(SEQ ID NO: 44) | 5-<br>atgagatttccatctatttttactgcagttttgtttgcagcatcttctgca<br>ttggcagcaccagttaacactactactgaagatgaaactgcacaaattcc<br>agcagaagcagttattggttactctgatttggaaggtgattttgatgttg<br>ctgttttgccattttctaactctactaataacggtttgttgtttattaata<br>ctactattgcatctattgcagcaaaggaagaaggtgtttctttggaaaaaa<br>gacagtttgttaacaagcaattcaattacaaagatccagttaatggtgttg<br>acattgcttatattaaaattccaaacgttggtcagatgcagccagttaaa<br>gctttcaagatccataacaaaatttgggttatcccagagagagacactt<br>tcactaatccagaggaaggtgatttgaacccaccaccagaagcaaaa<br>caggttccagttagttattatgacagtacttatctttccactgataacgag<br>aaagataactatttgaaaggtgttactaagctgtttgaaagaatttacag<br>tactgacttgggaagaatgttgctgacttcaattgttagaggaattccat<br>tttggggtggatctactattgacactgaattgaaagttatcgatactaatt<br>gtattaacgttatccaaccagacggttcctacagatctgaggagcttaa<br>cttggttattattggtccatccgctgacattattcaatttgagtgtaagtc<br>attcggacatgaggttttgaacctgactcgtaatggttatggttccactca<br>atatattagatttccccagatttacttttggtttcgaggaaagtttg<br>gaggttgatactaacccattgctgggtgcaggtaagtttgctactgatcca<br>gcagttactcttgctcatgagctgatccatgcaggtcatagattgtatggt<br>attgcaattaatccaaaccgtgttttaaagttaatactaatgcttattat<br>gaaatgtcaggtttggaagtttctttcgaagagttgagaactttcggagg<br>acatgatgctaagttcattgactctttgcaggaaaacgagttccgtctgt<br>actactataacaagttcaaggacatcgcatctactttgaacaaggcaa<br>agtcaattgttggtactactgcttcactgcaatatatgaagaacgttttca<br>aggagaagtacttgttgtccgaggatactagtggtaaattctctgttga<br>caaattgaagttcgacaaattgtacaaaatgctgactgagatctatact<br>gaagacaacttcgttaagtttttaaagttctgaacagaaagacttatttg<br>aactttgataaggctgtttttaagattaacattgttccaaaggttaactat<br>actatttatgacggtttcaatctgagaaacactaatcttgcagctaatttc<br>aatggtcagaatactgagattaataatatgaacttcactaagttgaaaaat<br>tttactggtttgtttgaattttacaagttgttgtgtgttcgtggaattatt<br>acttccaagactaaatctttggataagggttacaacaaaaaggaaacttgg<br>tgggaaacttggtggactgaatggtctcaaccaaagaagaagagaa<br>aggttgagaacctg tacttccaatccaatcatcaccatcaccatcacta<br>a-3' (SEQ ID NO: 45) |
| SMF | MRFPSIFTAVLFAASSALAAPVNTTTED<br>ETAQIPAEAVIGYSDLEGDFDVAVLPFS<br>NSTNNGLLFINTTIASIAAKEEGVSLEK<br>R (SEQ ID NO: 46) | 5'-<br>atgagatttccatctatttttactgcagttttgtttgcagcatcttctgca<br>ttggcagcaccagttaacactactactgaagatgaaactgcacaaattcc<br>agcagaagcagttattggttactctgatttggaaggtgattttgatgttg<br>ctgttttgccattttctaactctactaataacggtttgttgtttattaata<br>ctactattgcatctattgcagcaaaggaagaaggtgttTctttggaaaaaa<br>ga-3' (SEQ ID NO: 47) |
| TEV | ENLYFQSN (SEQ ID NO: 48) | 5'-gagaacctgtacttccaatccaat-3' (SEQ ID NO: 49) |

Example 7. Massive Fermentation and Purification of Non-Toxic Protease

It was attempted to ferment and purify large amounts of the recombinant *E. coli* strains constructed in Example 2. To this end, the stock solution of each recombinant strain was inoculated into LB medium supplemented with ampicillin and was cultured with shaking overnight at 37° C. and 200 rpm (seed culture). 3 to 4 L of LB medium supplemented with 50 μg/ml of ampicillin was placed in a 7-L jar fermenter, and 50 ppm of an Antifoam B emulsion was added thereto. Then, 30 mL of the strain cultured overnight was inoculated into the medium and fermented at 37° C. at an impeller speed of 250 rpm under an air pressure corresponding to 2 L/min of filtered air. When the strain reached an $OD_{600}$ of 0.3, the internal temperature of the fermenter was lowered with a cooler of the fermenter and the strain was cultured. When the strain reached an $OD_{600}$ of 0.6 to 0.7, 0.5 mM IPTG was added and the strain was cultured overnight (16 to 18 hours) at 18° C.

200 ml of lysis buffer (50 mM Tris-HCl (pH 8.0), 150 mM NaCl, 10% glycerol) was added to the cell pellet (about 5 g by wet weight) of 1L of the fermentation culture medium, and the cells were completely suspended. A buffer for cell disruption (1 mM PMSF, 1 mM β-ME (beta-mercaptoethanol), 0.1% Triton-X 100) was added to the cell suspension, and the cells were sonicated five times using a Sonics Vibra-cell sonicator for 4 min at pulse on/off of 4 sec/8 sec and at power of 65%. The cell lysate was divided into a supernatant and a cell lysate precipitate by centrifugation at 4° C. at 12,000 rpm for 30 minutes.

Figure 20:
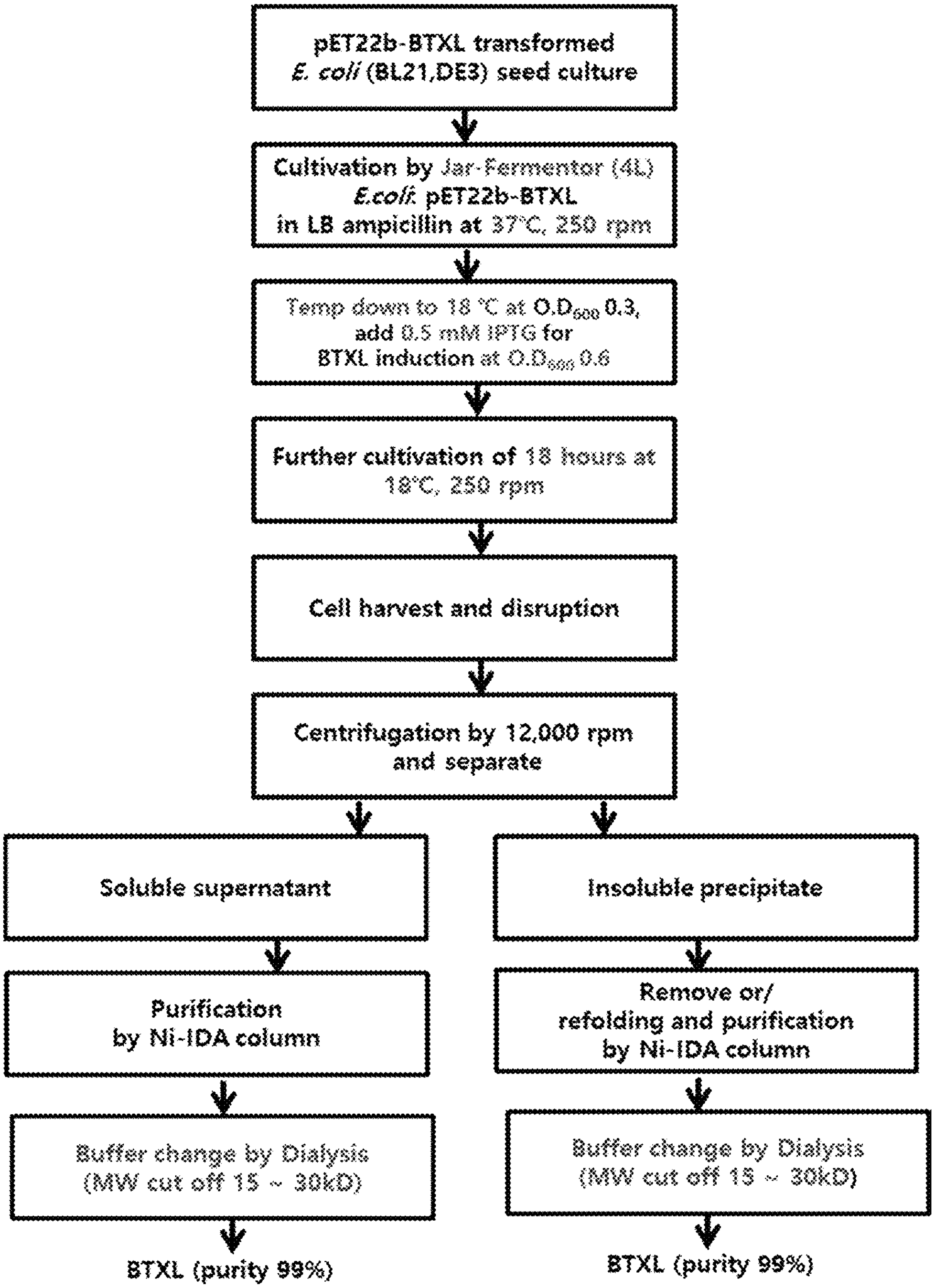
FIG. 20 is a schematic diagram showing a process for fermenting and purifying a large amount of a non-toxic protease according to the present invention.

Meanwhile, a Ni-IDA column (Workbeads™ 40 Ni-IDA, 40-650-001, Bio-Works, Sweden) was packed and the column was equilibrated with a 10-fold volume of equilibration buffer (50 mM Tris-HCl (pH 8.0), 150 mM NaCl, 10% glycerol, 0.1% TritonX-100, 1 mM PMSF, 1 mM β-ME). Ni-IDA resin was added to the centrifuged supernatant containing the soluble protein to induce a binding reaction with his-tag of the non-toxic protease at 4° C. for 2 hours, and was loaded into the column. The column was washed with a 20-fold volume of washing buffer A (50 mM Tris-HCl (pH 8.0), 150 mM NaCl, 10% glycerol, 1 mM β-ME), and then washed with a 20-fold volume of washing buffer (50 mM Tris-HCl (pH 8.0), 150 mM NaCl, 50 mM imidazole, 10% glycerol, 1 mM β-ME). The column was eluted stepwise with 1.5-fold volumes of elution buffers (100/200/300/500/700 mM imidazole, 50 mM Tris-HCl (pH 8.0), 150 mM NaCl, 10% glycerol, 1 mM β-ME). EDTA was added to each eluted fraction to a final concentration of 1 mM. The purity of each eluted fraction was analyzed by SDS-PAGE, and the high-purity eluted fractions obtained using the elution buffers containing 500 to 700 mM imidazole were combined, transferred to a dialysis membrane (molecular weight cut-off: 10-30 kDa), and dialyzed using PBS buffer to remove other chemical components, and the purified non-toxic protease was recovered. For cryopreservation, the non-toxic protease was dialyzed with PBS buffer containing 10% glycerol (FIG. 20).

As a result, as shown in FIGS. 21 to 26, it was confirmed that the wild-type non-toxic protease was recovered from the soluble fraction at a concentration of 3 to 6 mg/L, the non-toxic protease obtained by substituting the amino acid cysteine at position 430 of the wild-type non-toxic protease with serine was recovered from the soluble fraction at a concentration of 8 to 12 mg/L, and the non-toxic protease obtained by substituting the amino acid cysteine at position 430 of the wild-type non-toxic protease with alanine was recovered from the soluble fraction at a concentration of 15 to 20 mg/L, whereas the non-toxic protease obtained by substituting the amino acid cysteine at position 430 of the wild-type non-toxic protease with glycine was recovered from the soluble fraction at a concentration of 40 to 60 mg/L, suggesting that cysteine-to-glycine substitution at position 430 significantly increased the recovery of the non-toxic protease from the soluble fraction. It was believed that the reason why the recovery of the non-toxic protease from the soluble fraction can be enhanced as described is because cysteine-to-glycine substitution at position 430 of the non-toxic protease inhibited the formation of a bisulfide bond, the amount of the *E. coli* strain was increased through culturing at 37° C., the metabolism of the *E. coli* strain was slowed by lowering the culture temperature to 18° C. when an appropriate O.D. was reached, and expression of the protein was induced relatively slowly by adding IPTG at a decreased concentration of 0.5 mM, whereby the refolding efficiency of the non-toxic protease was increased. Meanwhile, in the case in which cysteine at position 430 was substituted with alanine or serine, a non-specific disulfide bond could be induced, and thus the efficiency of production of the non-toxic proteases from the soluble fraction was lower than that in the case in which cysteine at position 430 was substituted with glycine.

This effect of increasing the efficiency of expression purification of the mutated non-toxic protease in and from the soluble protein was higher than that for the wild-type non-toxic protease, even when the BFGFRP domain of the fibroblastic growth factor was fused to the mutated non-toxic protease. Thus, it could be seen that, even when another peptide is fused to the non-toxic peptide to the mutated non-toxic protease, the efficiency of expression and efficiency of purification of the mutated non-toxic protease is maintained. Specifically, the fusion non-toxic protease obtained by substituting cysteine at position of the non-toxic protease with glycine and fusing BFGFRP to the non-toxic protease was recovered at a concentration of 15 to 80 mg/L.

Example 8. Examination of Single Dose Toxicity of Non-Toxic Proteases

In order to confirm whether the toxicity of the non-toxic protease to be used in the present invention is reduced, the single dose toxicity thereof was evaluated in mice. An experiment was conducted using the wild-type non-toxic protease represented by SEQ ID NO: 1 of the present invention, and a “test for single dose administration of intraperitoneal administration of test substance in mice” was performed by the animal testing institution KPC (212-9, Opo-ro, Opo-eup, Gwangju-si, Gyeonggi-do, Korea).

As experimental animals, ICR mice were purchased from ORIENTBIO Inc. (Korea). The experiment was carried out using 35 6-week-old male mice, and animals that were not abnormal in appearance were brought into the breeding area and acclimatized in the animal room where the test was conducted, for 7 days. After 7 days of quarantine and acclimatization, healthy animals were selected by checking their health and suitability for testing. For drinking water, tap water was sterilized with a filter water sterilizer, irradiated with UV light, and freely fed using a drinking water bottle (250 mL) made of polycarbonate. The animals were allowed to freely access the rodent feed for laboratory animals provided by Cargill Agri Purina, Inc.

TABLE 5

| Test group | Drug | Dose (mg/kg) | Volume | Number of animals | Administration route and frequency | Observation period |
|---|---|---|---|---|---|---|
| G1 | Vehicle | n/a | 0.25 mL | | | |
| G2 | Test substance | 1 μg/mouse | 0.25 Ml | Five mice per group | Intraperitoneal injection, single | 4 days after administration |
| G4 | Test substance | 10 μg/mouse | 0.25 mL | | | |
| G4 | Test substance | 40 μg/mouse | 0.25 mL | | | |
| G5 | Test substance | 100 μg/mouse | 0.25 mL | | | |
| G6 | Test substance | 110 μg/mouse | 0.25 mL | | | |
| G7 | Test substance | 120 μg/mouse | 0.25 mL | | | |

As shown in Table 5 above, as the test substance, the wild-type non-toxic protease from which the heavy chain has been removed was purified according to the present invention and intraperitoneally injected into ICR mice (average body weight 34 g, n=5 for each concentration) at a dose of 1 to 120 μg/mouse. As a result, as shown in Table 6, it was confirmed that all the mice survived. Here, the dose (120 μg/mouse) for test group G7 corresponds to about 3.6 mg/kg mouse body weight. It is known that the median lethal dose (LD50) of natural botulinum toxin type A is about 0.3 ng/kg in rodent mice, and about 1 ng/kg in humans, which corresponds to a lethal dose of 1 μg for a 70-kg adult (Annu. Rev. Microbiol. 1999. 53:551-75, Eric A. Johnson, CLOSTRIDIAL TOXINS AS THERAPEUTIC AGENTS: Benefits of Nature's Most Toxic Proteins). Therefore, it was confirmed that the toxicity of the wild-type non-toxic protease used in the present invention decreased by $1.2\times10^7$ times compared to the reported median lethal dose (LD50) (0.3 ng/kg) of the natural botulinum toxin type A in mice, and that the mutated non-toxic protease of the present invention also had a significantly reduced median lethal dose (LD50) in mice, which is similar to that of the wild-type non-toxic protease.

TABLE 6

Summary: Incidence of mortality and daily observations

| Group | Sex | N | Mortality | Clinical observation | Days 1 | 2 | 3 | 4 | 5 |
|---|---|---|---|---|---|---|---|---|---|
| G1 (Vehicle) | Male | 5 | 0% | No clinical sign | 5 | 5 | 5 | 5 | 5 |
| G2 (1 μg/mouse) | Male | 5 | 0% | No clinical sign | 5 | 5 | 5 | 5 | 5 |
| G3 (10 μg/mouse) | Male | 5 | 0% | No clinical sign | 5 | 5 | 5 | 5 | 5 |

TABLE 6-continued

Summary: Incidence of mortality and daily observations

| Group | Sex | N | Mortality | Clinical observation | Days 1 | 2 | 3 | 4 | 5 |
|---|---|---|---|---|---|---|---|---|---|
| G4 (50 μg/mouse) | Male | 5 | 0% | No clinical sign | 5 | 5 | 5 | 5 | 5 |
| G5 (100 μg/mouse) | Male | 5 | 0% | No clinical sign | 5 | 5 | 5 | 5 | 5 |
| G6 (110 μg/mouse) | Male | 5 | 0% | No clinical sign | 5 | 5 | 5 | 5 | 5 |
| G7 (120 μg/mouse) | Male | 5 | 0% | No clinical sign | 5 | 5 | 5 | 5 | 5 |

Although the present invention has been described above with reference to the embodiments, it is to be understood that the present invention is not necessarily limited to the embodiments, and various modifications are possible without departing from the scope and spirit of the present invention. Accordingly, the scope of the present invention should be construed to include all embodiments falling within the scope of the claims appended hereto.

INDUSTRIAL APPLICABILITY

The present invention has advantages in that it is possible to inhibit aggregation into inclusion bodies, which generally occurs in the process of producing wild-type non-toxic protease using a recombinant microorganism, and thus it is possible to obtain active mutated non-toxic proteases from both a soluble fraction and an insoluble fraction, which are formed by disrupting the recombinant microorganism, even by a simple dialysis/refolding process alone, and accordingly, it is possible to produce non-toxic proteases in high yield.

SEQUENCE LIST FREE TEXT

An electronic file is attached.

The invention claimed is:

1. A mutated non-toxic protease in which an amino acid cysteine (Cys) at position 430 of a non-toxic protease represented by the amino acid sequence of SEQ ID NO: 1 is substituted with an amino acid glycine (Gly).

2. A fusion non-toxic protease in which the mutated non-toxic protease of claim 1 is fused with any one or more peptides selected from the group consisting of:

i) a cell penetrating peptide;

ii) a belt domain fragment peptide; and iii) a cell targeting peptide.

3. The fusion non-toxic proteinase of claim 2, wherein the cell penetrating peptide is represented by the amino acid sequence of SEQ ID NO: 3, the belt domain fragment peptide is represented by the amino acid sequence of SEQ ID NO: 5, and the cell targeting peptide is represented by the amino acid sequence of SEQ ID NO: 7.

4. The fusion non-toxic proteinase of claim 2, wherein the any one peptide is fused directly or via a linker to the non-toxic protease.

5. The fusion non-toxic proteinase of claim 4, wherein the linker is a peptide linker represented by (Gly) N wherein N is an integer ranging from 3 to 10.

6. The fusion non-toxic proteinase of claim 2, further comprising a cleavable peptide sequence by a protease for cleavage between a C-terminus of the non-toxic protease and an N-terminus of the peptide fused with the non-toxic protease.

7. The fusion non-toxic proteinase of claim 6, wherein the cleavable peptide sequence is represented by the amino acid sequence of SEQ ID NO: 27.

8. A mutant gene encoding the mutated non-toxic protease of claim 1.

9. The mutant gene of claim 8, which is represented by a nucleotide sequence of SEQ ID NO: 30.

10. A gene construct comprising:

the mutant gene of claim 9; and any one or more nucleic acids selected from the group consisting of i) a nucleic acid encoding a cell penetrating peptide;

ii) a nucleic acid encoding a belt domain fragment peptide; and iii) a nucleic acid encoding a cell targeting peptide.

11. The gene construct of claim 10, wherein the nucleic acid encoding the cell penetrating peptide is represented by the nucleotide sequence of SEQ ID NO: 4, the nucleic acid encoding the belt domain fragment peptide is represented by the nucleotide sequence of SEQ ID NO: 6, and the nucleic acid encoding the cell targeting peptide is represented by the nucleotide sequence of SEQ ID NO: 8.

12. The gene construct of claim 10, further comprising a nucleic acid encoding a linker peptide between the mutant gene encoding the mutated non-toxic protease and the any one or more nucleic acids.

13. The gene construct of claim 12, wherein the nucleic acid encoding the linker peptide is represented by the nucleotide sequence of SEQ ID NO: 26.

14. The gene construct of claim 10, further comprising a nucleic acid encoding a peptide sequence cleavable by a cleavage protease between the mutant gene encoding the mutated non-toxic protease and the one or more nucleic acids.

15. A pharmaceutical composition for treating Dystonia containing the non-toxic protease of claim 1 as an active ingredient.

16. The pharmaceutical composition of claim 15, wherein the Dystonia is selected from the group consisting of facial spasm, eyelid spasm, torticollis, blepharospasm, spasmodic torticollis, cervical dystonia, oromandibular dystonia, spasmodic dysphonia, migraine, anal pruritus, and hyperhidrosis.

17. The pharmaceutical composition of claim 16, which is for transdermal administration.

18. A hyaluronic acid microneedle patch containing the non-toxic protease of claim 1.

19. The hyaluronic acid microneedle patch of claim 18, which is for treatment or alleviation of a symptom selected from the group consisting of facial spasm, eyelid spasm, torticollis, blepharospasm, spasmodic torticollis, cervical dystonia, oromandibular dystonia, spasmodic dysphonia, migraine, anal pruritus, and hyperhidrosis.

* * * * *

SEQUENCE LISTING

```
<160> NUMBER OF SEQ ID NOS: 63

<210> SEQ ID NO 1
<211> LENGTH: 448
<212> TYPE: PRT
<213> ORGANISM: Artificial Sequence
<220> FEATURE:
```

-continued

<223> OTHER INFORMATION: Synthetic Botulinum toxin Light Chain

<400> SEQUENCE: 1

```
Met Gln Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400
```

-continued

```
Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445


<210> SEQ ID NO 2
<211> LENGTH: 1344
<212> TYPE: DNA
<213> ORGANISM: Artificial Sequence
<220> FEATURE:
<223> OTHER INFORMATION: Synthetic Botulinum toxin Light Chain

<400> SEQUENCE: 2

atgcaatttg ttaataaaca atttaattat aaagatcctg taaatggtgt tgatattgct     60

tatataaaaa ttccaaatgt aggacaaatg caaccagtaa aagcttttaa aattcataat    120

aaaatatggg ttattccaga aagagataca tttacaaatc ctgaagaagg agatttaaat    180

ccaccaccag aagcaaaaca agttccagtt tcatattatg attcaacata tttaagtaca    240

gataatgaaa aagataatta tttaaaggga gttacaaaat tatttgagag aatttattca    300

actgatcttg gaagaatgtt gttaacatca atagtaaggg gaataccatt ttggggtgga    360

agtacaatag atacagaatt aaaagttatt gatactaatt gtattaatgt gatacaacca    420

gatggtagtt atagatcaga agaacttaat ctagtaataa taggaccctc agctgatatt    480

atacagtttg aatgtaaaag ctttggacat gaagttttga atcttacgcg aaatggttat    540

ggctctactc aatacattag atttagccca gattttacat ttggttttga ggagtcactt    600

gaagttgata caaatcctct tttaggtgca ggcaaatttg ctacagatcc agcagtaaca    660

ttagcacatg aacttataca tgctggacat agattatatg gaatagcaat taatccaaat    720

agggttttta aagtaaatac taatgcctat tatgaaatga gtgggttaga agtaagcttt    780

gaggaactta gaacatttgg gggacatgat gcaaagttta tagatagttt acaggaaaac    840

gaatttcgtc tatattatta taataagttt aaagatatag caagtacact taataaagct    900

aaatcaatag taggtactac tgcttcatta cagtatatga aaaatgtttt taaagagaaa    960

tatctcctat ctgaagatac atctggaaaa ttttcggtag ataaattaaa atttgataag   1020

ttatacaaaa tgttaacaga gatttacaca gaggataatt ttgttaagtt ttttaaagta   1080

cttaacagaa aaacatattt gaattttgat aaagccgtat ttaagataaa tatagtacct   1140

aaggtaaatt acacaatata tgatggattt aatttaagaa atacaaattt agcagcaaac   1200

tttaatggtc aaaatacaga aattaataat atgaatttta ctaaactaaa aaattttact   1260

ggattgtttg aattttataa gttgctatgt gtaagaggga taataacttc taaaactaaa   1320

tcattagata aaggatacaa taag                                          1344


<210> SEQ ID NO 3
<211> LENGTH: 22
<212> TYPE: PRT
<213> ORGANISM: Artificial Sequence
<220> FEATURE:
<223> OTHER INFORMATION: PEP1

<400> SEQUENCE: 3

Met Lys Glu Thr Trp Trp Glu Thr Trp Trp Thr Glu Trp Ser Gln Pro
1               5                   10                  15

Lys Lys Lys Arg Lys Val
```

-continued

20

<210> SEQ ID NO 4
<211> LENGTH: 66
<212> TYPE: DNA
<213> ORGANISM: Artificial Sequence
<220> FEATURE:
<223> OTHER INFORMATION: PEP1

<400> SEQUENCE: 4
atgaaggaaa cttggtggga aacttggtgg actgaatggt ctcaaccaaa gaagaagaga 60
aaggtt 66

<210> SEQ ID NO 5
<211> LENGTH: 6
<212> TYPE: PRT
<213> ORGANISM: Artificial Sequence
<220> FEATURE:
<223> OTHER INFORMATION: Belt'

<400> SEQUENCE: 5

Ala Leu Asn Asp Leu Cys
1 5

<210> SEQ ID NO 6
<211> LENGTH: 18
<212> TYPE: DNA
<213> ORGANISM: Artificial Sequence
<220> FEATURE:
<223> OTHER INFORMATION: Belt'

<400> SEQUENCE: 6
gcgctgaacg atctgtgc 18

<210> SEQ ID NO 7
<211> LENGTH: 11
<212> TYPE: PRT
<213> ORGANISM: Artificial Sequence
<220> FEATURE:
<223> OTHER INFORMATION: BFGFRP
<220> FEATURE:
<221> NAME/KEY: MISC_FEATURE
<222> LOCATION: (8)..(8)
<223> OTHER INFORMATION: X is S or T

<400> SEQUENCE: 7

Thr Tyr Arg Ser Arg Lys Tyr Xaa Ser Trp Tyr
1 5 10

<210> SEQ ID NO 8
<211> LENGTH: 33
<212> TYPE: DNA
<213> ORGANISM: Artificial Sequence
<220> FEATURE:
<223> OTHER INFORMATION: BFGFRP

<400> SEQUENCE: 8
acctatcgca gccgcaaata tascagctgg tat 33

<210> SEQ ID NO 9
<211> LENGTH: 475
<212> TYPE: PRT
<213> ORGANISM: Artificial Sequence
<220> FEATURE:
<223> OTHER INFORMATION: PEP1-(-M)BTX-L-His

<400> SEQUENCE: 9

```
Met Lys Glu Thr Trp Trp Glu Thr Trp Trp Thr Glu Trp Ser Gln Pro
1               5                   10                  15

Lys Lys Lys Arg Lys Val Gln Phe Val Asn Lys Gln Phe Asn Tyr Lys
            20                  25                  30

Asp Pro Val Asn Gly Val Asp Ile Ala Tyr Ile Lys Ile Pro Asn Val
        35                  40                  45

Gly Gln Met Gln Pro Val Lys Ala Phe Lys Ile His Asn Lys Ile Trp
    50                  55                  60

Val Ile Pro Glu Arg Asp Thr Phe Thr Asn Pro Glu Glu Gly Asp Leu
65                  70                  75                  80

Asn Pro Pro Pro Glu Ala Lys Gln Val Pro Val Ser Tyr Tyr Asp Ser
                85                  90                  95

Thr Tyr Leu Ser Thr Asp Asn Glu Lys Asp Asn Tyr Leu Lys Gly Val
            100                 105                 110

Thr Lys Leu Phe Glu Arg Ile Tyr Ser Thr Asp Leu Gly Arg Met Leu
        115                 120                 125

Leu Thr Ser Ile Val Arg Gly Ile Pro Phe Trp Gly Gly Ser Thr Ile
    130                 135                 140

Asp Thr Glu Leu Lys Val Ile Asp Thr Asn Cys Ile Asn Val Ile Gln
145                 150                 155                 160

Pro Asp Gly Ser Tyr Arg Ser Glu Glu Leu Asn Leu Val Ile Ile Gly
                165                 170                 175

Pro Ser Ala Asp Ile Ile Gln Phe Glu Cys Lys Ser Phe Gly His Glu
            180                 185                 190

Val Leu Asn Leu Thr Arg Asn Gly Tyr Gly Ser Thr Gln Tyr Ile Arg
        195                 200                 205

Phe Ser Pro Asp Phe Thr Phe Gly Phe Glu Glu Ser Leu Glu Val Asp
    210                 215                 220

Thr Asn Pro Leu Leu Gly Ala Gly Lys Phe Ala Thr Asp Pro Ala Val
225                 230                 235                 240

Thr Leu Ala His Glu Leu Ile His Ala Gly His Arg Leu Tyr Gly Ile
                245                 250                 255

Ala Ile Asn Pro Asn Arg Val Phe Lys Val Asn Thr Asn Ala Tyr Tyr
            260                 265                 270

Glu Met Ser Gly Leu Glu Val Ser Phe Glu Glu Leu Arg Thr Phe Gly
        275                 280                 285

Gly His Asp Ala Lys Phe Ile Asp Ser Leu Gln Glu Asn Glu Phe Arg
    290                 295                 300

Leu Tyr Tyr Tyr Asn Lys Phe Lys Asp Ile Ala Ser Thr Leu Asn Lys
305                 310                 315                 320

Ala Lys Ser Ile Val Gly Thr Thr Ala Ser Leu Gln Tyr Met Lys Asn
                325                 330                 335

Val Phe Lys Glu Lys Tyr Leu Leu Ser Glu Asp Thr Ser Gly Lys Phe
            340                 345                 350

Ser Val Asp Lys Leu Lys Phe Asp Lys Leu Tyr Lys Met Leu Thr Glu
        355                 360                 365

Ile Tyr Thr Glu Asp Asn Phe Val Lys Phe Phe Lys Val Leu Asn Arg
    370                 375                 380

Lys Thr Tyr Leu Asn Phe Asp Lys Ala Val Phe Lys Ile Asn Ile Val
385                 390                 395                 400

Pro Lys Val Asn Tyr Thr Ile Tyr Asp Gly Phe Asn Leu Arg Asn Thr
                405                 410                 415
```

-continued

```
Asn Leu Ala Ala Asn Phe Asn Gly Gln Asn Thr Glu Ile Asn Asn Met
            420                 425                 430

Asn Phe Thr Lys Leu Lys Asn Phe Thr Gly Leu Phe Glu Phe Tyr Lys
        435                 440                 445

Leu Leu Cys Val Arg Gly Ile Ile Thr Ser Lys Thr Lys Ser Leu Asp
    450                 455                 460

Lys Gly Tyr Asn Lys His His His His His His
465                 470                 475
```

<210> SEQ ID NO 10
<211> LENGTH: 1428
<212> TYPE: DNA
<213> ORGANISM: Artificial Sequence
<220> FEATURE:
<223> OTHER INFORMATION: PEP1-(-M)BTX-L-His

<400> SEQUENCE: 10

```
atgaaggaaa cttggtggga aacttggtgg actgaatggt ctcaaccaaa gaagaagaga     60

aaggttcaat ttgttaataa acaatttaat tataaagatc ctgtaaatgg tgttgatatt    120

gcttatataa aaattccaaa tgtaggacaa atgcaaccag taaaagcttt taaaattcat    180

aataaaatat gggttattcc agaaagagat acatttacaa atcctgaaga aggagattta    240

aatccaccac cagaagcaaa acaagttcca gtttcatatt atgattcaac atatttaagt    300

acagataatg aaaaagataa ttatttaaag ggagttacaa aattatttga gagaatttat    360

tcaactgatc ttggaagaat gttgttaaca tcaatagtaa ggggaatacc attttggggt    420

ggaagtacaa tagatacaga attaaaagtt attgatacta attgtattaa tgtgatacaa    480

ccagatggta gttatagatc agaagaactt aatctagtaa taataggacc ctcagctgat    540

attatacagt ttgaatgtaa aagctttgga catgaagttt tgaatcttac gcgaaatggt    600

tatggctcta ctcaatacat tagatttagc ccagatttta catttggttt tgaggagtca    660

cttgaagttg atacaaatcc tcttttaggt gcaggcaaat ttgctacaga tccagcagta    720

acattagcac atgaacttat acatgctgga catagattat atggaatagc aattaatcca    780

aatagggttt ttaaagtaaa tactaatgcc tattatgaaa tgagtgggtt agaagtaagc    840

tttgaggaac ttagaacatt tggggggacat gatgcaaagt ttatagatag tttacaggaa    900

aacgaatttc gtctatatta ttataataag tttaaagata tagcaagtac acttaataaa    960

gctaaatcaa tagtaggtac tactgcttca ttacagtata tgaaaaatgt ttttaaagag   1020

aaatatctcc tatctgaaga tacatctgga aaattttcgg tagataaatt aaaatttgat   1080

aagttataca aaatgttaac agagatttac acagaggata attttgttaa gtttttttaaa   1140

gtacttaaca gaaaaacata tttgaatttt gataaagccg tatttaagat aaatatagta   1200

cctaaggtaa attacacaat atatgatgga tttaatttaa gaaatacaaa tttagcagca   1260

aactttaatg gtcaaaatac agaaattaat aatatgaatt ttactaaact aaaaaatttt   1320

actggattgt ttgaatttta taagttgcta tgtgtaagag ggataataac ttctaaaact   1380

aaatcattag ataaaggata caataagcat caccatcacc atcactaa                1428
```

<210> SEQ ID NO 11
<211> LENGTH: 475
<212> TYPE: PRT
<213> ORGANISM: Artificial Sequence
<220> FEATURE:
<223> OTHER INFORMATION: PEP1-(-M)BTX-L-His (E.coli codon optimization)

<400> SEQUENCE: 11

-continued

```
Met Lys Glu Thr Trp Trp Glu Thr Trp Trp Thr Glu Trp Ser Gln Pro
1               5                   10                  15

Lys Lys Lys Arg Lys Val Gln Phe Val Asn Lys Gln Phe Asn Tyr Lys
            20                  25                  30

Asp Pro Val Asn Gly Val Asp Ile Ala Tyr Ile Lys Ile Pro Asn Val
        35                  40                  45

Gly Gln Met Gln Pro Val Lys Ala Phe Lys Ile His Asn Lys Ile Trp
    50                  55                  60

Val Ile Pro Glu Arg Asp Thr Phe Thr Asn Pro Glu Glu Gly Asp Leu
65                  70                  75                  80

Asn Pro Pro Pro Glu Ala Lys Gln Val Pro Val Ser Tyr Tyr Asp Ser
                85                  90                  95

Thr Tyr Leu Ser Thr Asp Asn Glu Lys Asp Asn Tyr Leu Lys Gly Val
            100                 105                 110

Thr Lys Leu Phe Glu Arg Ile Tyr Ser Thr Asp Leu Gly Arg Met Leu
        115                 120                 125

Leu Thr Ser Ile Val Arg Gly Ile Pro Phe Trp Gly Gly Ser Thr Ile
    130                 135                 140

Asp Thr Glu Leu Lys Val Ile Asp Thr Asn Cys Ile Asn Val Ile Gln
145                 150                 155                 160

Pro Asp Gly Ser Tyr Arg Ser Glu Glu Leu Asn Leu Val Ile Ile Gly
                165                 170                 175

Pro Ser Ala Asp Ile Ile Gln Phe Glu Cys Lys Ser Phe Gly His Glu
            180                 185                 190

Val Leu Asn Leu Thr Arg Asn Gly Tyr Gly Ser Thr Gln Tyr Ile Arg
        195                 200                 205

Phe Ser Pro Asp Phe Thr Phe Gly Phe Glu Glu Ser Leu Glu Val Asp
    210                 215                 220

Thr Asn Pro Leu Leu Gly Ala Gly Lys Phe Ala Thr Asp Pro Ala Val
225                 230                 235                 240

Thr Leu Ala His Glu Leu Ile His Ala Gly His Arg Leu Tyr Gly Ile
                245                 250                 255

Ala Ile Asn Pro Asn Arg Val Phe Lys Val Asn Thr Asn Ala Tyr Tyr
            260                 265                 270

Glu Met Ser Gly Leu Glu Val Ser Phe Glu Glu Leu Arg Thr Phe Gly
        275                 280                 285

Gly His Asp Ala Lys Phe Ile Asp Ser Leu Gln Glu Asn Glu Phe Arg
    290                 295                 300

Leu Tyr Tyr Tyr Asn Lys Phe Lys Asp Ile Ala Ser Thr Leu Asn Lys
305                 310                 315                 320

Ala Lys Ser Ile Val Gly Thr Thr Ala Ser Leu Gln Tyr Met Lys Asn
                325                 330                 335

Val Phe Lys Glu Lys Tyr Leu Leu Ser Glu Asp Thr Ser Gly Lys Phe
            340                 345                 350

Ser Val Asp Lys Leu Lys Phe Asp Lys Leu Tyr Lys Met Leu Thr Glu
        355                 360                 365

Ile Tyr Thr Glu Asp Asn Phe Val Lys Phe Phe Lys Val Leu Asn Arg
    370                 375                 380

Lys Thr Tyr Leu Asn Phe Asp Lys Ala Val Phe Lys Ile Asn Ile Val
385                 390                 395                 400

Pro Lys Val Asn Tyr Thr Ile Tyr Asp Gly Phe Asn Leu Arg Asn Thr
                405                 410                 415
```

```
Asn Leu Ala Ala Asn Phe Asn Gly Gln Asn Thr Glu Ile Asn Asn Met
            420                 425                 430

Asn Phe Thr Lys Leu Lys Asn Phe Thr Gly Leu Phe Glu Phe Tyr Lys
        435                 440                 445

Leu Leu Cys Val Arg Gly Ile Ile Thr Ser Lys Thr Lys Ser Leu Asp
    450                 455                 460

Lys Gly Tyr Asn Lys His His His His His His
465                 470                 475


<210> SEQ ID NO 12
<211> LENGTH: 1440
<212> TYPE: DNA
<213> ORGANISM: Artificial Sequence
<220> FEATURE:
<223> OTHER INFORMATION: gene cassette for cloning PEP1-(-M)BTX-L-His
      (E.coli codon optimization)

<400> SEQUENCE: 12

catatgaagg aaacttggtg ggaaacttgg tggaccgaat ggtctcaacc aaagaagaag      60

cgcaaggttc aatttgttaa taaacaattt aattataaag atccagtaaa tggtgtcgac     120

attgcttata tcaaaattcc aaatgtaggc caaatgcaac cagtaaaagc ttttaaaatt     180

cataataaaa tctgggttat tccagaacgc gataccttta ccaatccgga agaaggtgat     240

ctgaatccac caccagaagc aaaacaagtt ccagttagct attatgatag cacctatctg     300

agcaccgata atgaaaaaga taattatctg aagggcgtta ccaaactgtt tgagcgcatt     360

tatagcactg atctgggtcg catgctgctg accagcatcg tacgcggtat cccattttgg     420

ggtggtagca ccatcgatac cgaactgaaa gttattgata ctaattgtat taatgtgatc     480

caaccagatg gtagctatcg cagcgaagaa ctgaatctgg taatcatcgg tccgagcgct     540

gatattatcc agtttgaatg taaaagcttt ggtcatgaag ttctgaatct gacccgtaat     600

ggttatggca gcacccaata cattcgcttt agcccagatt ttacctttgg ttttgaggag     660

agcctggaag ttgataccaa tccgctgctg ggtgcaggca aatttgctac cgatccagca     720

gtaaccctgg cacatgaact gatacatgct ggccatcgcc tgtatggtat cgcaattaat     780

ccaaatcgcg tttttaaagt aaataccaat gcctattatg aaatgagcgg tctggaagta     840

agctttgagg aactgcgcac ctttggtggt catgatgcaa agtttatcga tagcctgcag     900

gaaaacgaat ttcgtctgta ttattataat aagtttaaag atatcgcaag caccctgaat     960

aaagctaaaa gcatcgtagg taccaccgct agcctgcagt atatgaaaaa tgtttttaaa    1020

gagaaatatc tgctgtctga agatacctct ggcaaattta gcgtagataa actgaaattt    1080

gataagctgt acaaaatgct gaccgagatt tacaccgagg ataattttgt taagtttttt    1140

aaagtactga accgcaaaac ctatctgaat tttgataaag ccgtatttaa gatcaatatc    1200

gtaccgaagg taaattacac catctatgat ggttttaatc tgcgcaatac caatctggca    1260

gcaaacttta atggtcaaaa taccgaaatt aataatatga attttaccaa actgaaaaat    1320

tttaccggtc tgtttgaatt ctataagctg ctgtgtgtac gcggtatcat caccagcaaa    1380

accaaaagcc tggataaagg ctacaataag catcaccatc accatcacta ataactcgag    1440


<210> SEQ ID NO 13
<211> LENGTH: 475
<212> TYPE: PRT
<213> ORGANISM: Artificial Sequence
<220> FEATURE:
<223> OTHER INFORMATION: PEP1-(-M)BTX-L((C430G))-His (E.coli codon
      optimization)
```

-continued

<400> SEQUENCE: 13

```
Met Lys Glu Thr Trp Trp Glu Thr Trp Trp Thr Glu Trp Ser Gln Pro
1               5                   10                  15

Lys Lys Lys Arg Lys Val Gln Phe Val Asn Lys Gln Phe Asn Tyr Lys
            20                  25                  30

Asp Pro Val Asn Gly Val Asp Ile Ala Tyr Ile Lys Ile Pro Asn Val
        35                  40                  45

Gly Gln Met Gln Pro Val Lys Ala Phe Lys Ile His Asn Lys Ile Trp
    50                  55                  60

Val Ile Pro Glu Arg Asp Thr Phe Thr Asn Pro Glu Glu Gly Asp Leu
65                  70                  75                  80

Asn Pro Pro Pro Glu Ala Lys Gln Val Pro Val Ser Tyr Tyr Asp Ser
                85                  90                  95

Thr Tyr Leu Ser Thr Asp Asn Glu Lys Asp Asn Tyr Leu Lys Gly Val
            100                 105                 110

Thr Lys Leu Phe Glu Arg Ile Tyr Ser Thr Asp Leu Gly Arg Met Leu
        115                 120                 125

Leu Thr Ser Ile Val Arg Gly Ile Pro Phe Trp Gly Gly Ser Thr Ile
    130                 135                 140

Asp Thr Glu Leu Lys Val Ile Asp Thr Asn Cys Ile Asn Val Ile Gln
145                 150                 155                 160

Pro Asp Gly Ser Tyr Arg Ser Glu Glu Leu Asn Leu Val Ile Ile Gly
                165                 170                 175

Pro Ser Ala Asp Ile Ile Gln Phe Glu Cys Lys Ser Phe Gly His Glu
            180                 185                 190

Val Leu Asn Leu Thr Arg Asn Gly Tyr Gly Ser Thr Gln Tyr Ile Arg
        195                 200                 205

Phe Ser Pro Asp Phe Thr Phe Gly Phe Glu Glu Ser Leu Glu Val Asp
    210                 215                 220

Thr Asn Pro Leu Leu Gly Ala Gly Lys Phe Ala Thr Asp Pro Ala Val
225                 230                 235                 240

Thr Leu Ala His Glu Leu Ile His Ala Gly His Arg Leu Tyr Gly Ile
                245                 250                 255

Ala Ile Asn Pro Asn Arg Val Phe Lys Val Asn Thr Asn Ala Tyr Tyr
            260                 265                 270

Glu Met Ser Gly Leu Glu Val Ser Phe Glu Glu Leu Arg Thr Phe Gly
        275                 280                 285

Gly His Asp Ala Lys Phe Ile Asp Ser Leu Gln Glu Asn Glu Phe Arg
    290                 295                 300

Leu Tyr Tyr Tyr Asn Lys Phe Lys Asp Ile Ala Ser Thr Leu Asn Lys
305                 310                 315                 320

Ala Lys Ser Ile Val Gly Thr Thr Ala Ser Leu Gln Tyr Met Lys Asn
                325                 330                 335

Val Phe Lys Glu Lys Tyr Leu Leu Ser Glu Asp Thr Ser Gly Lys Phe
            340                 345                 350

Ser Val Asp Lys Leu Lys Phe Asp Lys Leu Tyr Lys Met Leu Thr Glu
        355                 360                 365

Ile Tyr Thr Glu Asp Asn Phe Val Lys Phe Phe Lys Val Leu Asn Arg
    370                 375                 380

Lys Thr Tyr Leu Asn Phe Asp Lys Ala Val Phe Lys Ile Asn Ile Val
385                 390                 395                 400

Pro Lys Val Asn Tyr Thr Ile Tyr Asp Gly Phe Asn Leu Arg Asn Thr
```

```
                405                 410                 415

Asn Leu Ala Ala Asn Phe Asn Gly Gln Asn Thr Glu Ile Asn Asn Met
            420                 425                 430

Asn Phe Thr Lys Leu Lys Asn Phe Thr Gly Leu Phe Glu Phe Tyr Lys
        435                 440                 445

Leu Leu Gly Val Arg Gly Ile Ile Thr Ser Lys Thr Lys Ser Leu Asp
    450                 455                 460

Lys Gly Tyr Asn Lys His His His His His His
465                 470                 475


<210> SEQ ID NO 14
<211> LENGTH: 1440
<212> TYPE: DNA
<213> ORGANISM: Artificial Sequence
<220> FEATURE:
<223> OTHER INFORMATION: gene casstte for cloning PEP1-(-M)BTX-
      L((C430G))-His (E.coli codon optimization)

<400> SEQUENCE: 14

catatgaagg aaacttggtg ggaaacttgg tggaccgaat ggtctcaacc aaagaagaag     60

cgcaaggttc aatttgttaa taaacaattt aattataaag atccagtaaa tggtgtcgac    120

attgcttata tcaaaattcc aaatgtaggc caaatgcaac cagtaaaagc ttttaaaatt    180

cataataaaa tctgggttat tccagaacgc gataccttta ccaatccgga agaaggtgat    240

ctgaatccac caccagaagc aaaacaagtt ccagttagct attatgatag cacctatctg    300

agcaccgata atgaaaaaga taattatctg aagggcgtta ccaaactgtt tgagcgcatt    360

tatagcactg atctgggtcg catgctgctg accagcatcg tacgcggtat cccattttgg    420

ggtggtagca ccatcgatac cgaactgaaa gttattgata ctaattgtat taatgtgatc    480

caaccagatg gtagctatcg cagcgaagaa ctgaatctgg taatcatcgg tccgagcgct    540

gatattatcc agtttgaatg taaaagcttt ggtcatgaag ttctgaatct gacccgtaat    600

ggttatggca gcacccaata cattcgcttt agcccagatt ttacctttgg ttttgaggag    660

agcctggaag ttgataccaa tccgctgctg ggtgcaggca aatttgctac cgatccagca    720

gtaaccctgg cacatgaact gatacatgct ggccatcgcc tgtatggtat cgcaattaat    780

ccaaatcgcg tttttaaagt aaataccaat gcctattatg aaatgagcgg tctggaagta    840

agctttgagg aactgcgcac ctttggtggt catgatgcaa agtttatcga tagcctgcag    900

gaaaacgaat ttcgtctgta ttattataat aagtttaaag atatcgcaag caccctgaat    960

aaagctaaaa gcatcgtagg taccaccgct agcctgcagt atatgaaaaa tgtttttaaa   1020

gagaaatatc tgctgtctga agatacctct ggcaaattta gcgtagataa actgaaattt   1080

gataagctgt acaaaatgct gaccgagatt tacaccgagg ataattttgt taagtttttt   1140

aaagtactga accgcaaaac ctatctgaat tttgataaag ccgtatttaa gatcaatatc   1200

gtaccgaagg taaattacac catctatgat ggttttaatc tgcgcaatac caatctggca   1260

gcaaacttta atggtcaaaa taccgaaatt aataatatga attttaccaa actgaaaaat   1320

tttaccggtc tgtttgaatt ctataagctg ctgggcgtac gcggtatcat caccagcaaa   1380

accaaaagcc tggataaagg ctacaataag catcaccatc accatcacta ataactcgag   1440


<210> SEQ ID NO 15
<211> LENGTH: 475
<212> TYPE: PRT
<213> ORGANISM: Artificial Sequence
<220> FEATURE:
```

<223> OTHER INFORMATION: PEP1-(-M)BTX-L(C430A)-His (E.coli codon
      optimization)

<400> SEQUENCE: 15

Met Lys Glu Thr Trp Trp Glu Thr Trp Trp Thr Glu Trp Ser Gln Pro
1               5                   10                  15

Lys Lys Lys Arg Lys Val Gln Phe Val Asn Lys Gln Phe Asn Tyr Lys
            20                  25                  30

Asp Pro Val Asn Gly Val Asp Ile Ala Tyr Ile Lys Ile Pro Asn Val
        35                  40                  45

Gly Gln Met Gln Pro Val Lys Ala Phe Lys Ile His Asn Lys Ile Trp
    50                  55                  60

Val Ile Pro Glu Arg Asp Thr Phe Thr Asn Pro Glu Glu Gly Asp Leu
65                  70                  75                  80

Asn Pro Pro Pro Glu Ala Lys Gln Val Pro Val Ser Tyr Tyr Asp Ser
                85                  90                  95

Thr Tyr Leu Ser Thr Asp Asn Glu Lys Asp Asn Tyr Leu Lys Gly Val
            100                 105                 110

Thr Lys Leu Phe Glu Arg Ile Tyr Ser Thr Asp Leu Gly Arg Met Leu
        115                 120                 125

Leu Thr Ser Ile Val Arg Gly Ile Pro Phe Trp Gly Gly Ser Thr Ile
    130                 135                 140

Asp Thr Glu Leu Lys Val Ile Asp Thr Asn Cys Ile Asn Val Ile Gln
145                 150                 155                 160

Pro Asp Gly Ser Tyr Arg Ser Glu Glu Leu Asn Leu Val Ile Ile Gly
                165                 170                 175

Pro Ser Ala Asp Ile Ile Gln Phe Glu Cys Lys Ser Phe Gly His Glu
            180                 185                 190

Val Leu Asn Leu Thr Arg Asn Gly Tyr Gly Ser Thr Gln Tyr Ile Arg
        195                 200                 205

Phe Ser Pro Asp Phe Thr Phe Gly Phe Glu Glu Ser Leu Glu Val Asp
    210                 215                 220

Thr Asn Pro Leu Leu Gly Ala Gly Lys Phe Ala Thr Asp Pro Ala Val
225                 230                 235                 240

Thr Leu Ala His Glu Leu Ile His Ala Gly His Arg Leu Tyr Gly Ile
                245                 250                 255

Ala Ile Asn Pro Asn Arg Val Phe Lys Val Asn Thr Asn Ala Tyr Tyr
            260                 265                 270

Glu Met Ser Gly Leu Glu Val Ser Phe Glu Glu Leu Arg Thr Phe Gly
        275                 280                 285

Gly His Asp Ala Lys Phe Ile Asp Ser Leu Gln Glu Asn Glu Phe Arg
    290                 295                 300

Leu Tyr Tyr Tyr Asn Lys Phe Lys Asp Ile Ala Ser Thr Leu Asn Lys
305                 310                 315                 320

Ala Lys Ser Ile Val Gly Thr Thr Ala Ser Leu Gln Tyr Met Lys Asn
                325                 330                 335

Val Phe Lys Glu Lys Tyr Leu Leu Ser Glu Asp Thr Ser Gly Lys Phe
            340                 345                 350

Ser Val Asp Lys Leu Lys Phe Asp Lys Leu Tyr Lys Met Leu Thr Glu
        355                 360                 365

Ile Tyr Thr Glu Asp Asn Phe Val Lys Phe Phe Lys Val Leu Asn Arg
    370                 375                 380

Lys Thr Tyr Leu Asn Phe Asp Lys Ala Val Phe Lys Ile Asn Ile Val
385                 390                 395                 400

```
Pro Lys Val Asn Tyr Thr Ile Tyr Asp Gly Phe Asn Leu Arg Asn Thr
                405                 410                 415

Asn Leu Ala Ala Asn Phe Asn Gly Gln Asn Thr Glu Ile Asn Asn Met
            420                 425                 430

Asn Phe Thr Lys Leu Lys Asn Phe Thr Gly Leu Phe Glu Phe Tyr Lys
        435                 440                 445

Leu Leu Ala Val Arg Gly Ile Ile Thr Ser Lys Thr Lys Ser Leu Asp
    450                 455                 460

Lys Gly Tyr Asn Lys His His His His His His
465                 470                 475


<210> SEQ ID NO 16
<211> LENGTH: 1440
<212> TYPE: DNA
<213> ORGANISM: Artificial Sequence
<220> FEATURE:
<223> OTHER INFORMATION: gene casstte for cloning PEP1-(-M)BTX-L(C430A)-
      His (E.coli codon optimization)

<400> SEQUENCE: 16

catatgaagg aaacttggtg ggaaacttgg tggaccgaat ggtctcaacc aaagaagaag     60

cgcaaggttc aatttgttaa taaacaattt aattataaag atccagtaaa tggtgtcgac    120

attgcttata tcaaaattcc aaatgtaggc caaatgcaac cagtaaaagc ttttaaaatt    180

cataataaaa tctgggttat tccagaacgc gataccttta ccaatccgga agaaggtgat    240

ctgaatccac caccagaagc aaaacaagtt ccagttagct attatgatag cacctatctg    300

agcaccgata atgaaaaaga taattatctg aagggcgtta ccaaactgtt tgagcgcatt    360

tatagcactg atctgggtcg catgctgctg accagcatcg tacgcggtat cccattttgg    420

ggtggtagca ccatcgatac cgaactgaaa gttattgata ctaattgtat taatgtgatc    480

caaccagatg gtagctatcg cagcgaagaa ctgaatctgg taatcatcgg tccgagcgct    540

gatattatcc agtttgaatg taaaagcttt ggtcatgaag ttctgaatct gacccgtaat    600

ggttatggca gcacccaata cattcgcttt agcccagatt ttacctttgg ttttgaggag    660

agcctggaag ttgataccaa tccgctgctg ggtgcaggca aatttgctac cgatccagca    720

gtaaccctgg cacatgaact gatacatgct ggccatcgcc tgtatggtat cgcaattaat    780

ccaaatcgcg tttttaaagt aaataccaat gcctattatg aaatgagcgg tctggaagta    840

agctttgagg aactgcgcac ctttggtggt catgatgcaa agtttatcga tagcctgcag    900

gaaaacgaat ttcgtctgta ttattataat aagtttaaag atatcgcaag caccctgaat    960

aaagctaaaa gcatcgtagg taccaccgct agcctgcagt atatgaaaaa tgtttttaaa   1020

gagaaatatc tgctgtctga agatacctct ggcaaattta gcgtagataa actgaaattt   1080

gataagctgt acaaaatgct gaccgagatt tacaccgagg ataattttgt taagtttttt   1140

aaagtactga accgcaaaac ctatctgaat tttgataaag ccgtatttaa gatcaatatc   1200

gtaccgaagg taaattacac catctatgat ggttttaatc tgcgcaatac caatctggca   1260

gcaaacttta atggtcaaaa taccgaaatt aataatatga attttaccaa actgaaaaat   1320

tttaccggtc tgtttgaatt ctataagctg ctgagcgtac gcggtatcat caccagcaaa   1380

accaaaagcc tggataaagg ctacaataag catcaccatc accatcacta ataactcgag   1440


<210> SEQ ID NO 17
<211> LENGTH: 475
<212> TYPE: PRT
```

-continued

<213> ORGANISM: Artificial Sequence
<220> FEATURE:
<223> OTHER INFORMATION: PEP1-(-M)BTX-L(C430S)-His

<400> SEQUENCE: 17

```
Met Lys Glu Thr Trp Trp Glu Thr Trp Trp Thr Glu Trp Ser Gln Pro
1               5                   10                  15

Lys Lys Lys Arg Lys Val Gln Phe Val Asn Lys Gln Phe Asn Tyr Lys
            20                  25                  30

Asp Pro Val Asn Gly Val Asp Ile Ala Tyr Ile Lys Ile Pro Asn Val
        35                  40                  45

Gly Gln Met Gln Pro Val Lys Ala Phe Lys Ile His Asn Lys Ile Trp
    50                  55                  60

Val Ile Pro Glu Arg Asp Thr Phe Thr Asn Pro Glu Glu Gly Asp Leu
65                  70                  75                  80

Asn Pro Pro Pro Glu Ala Lys Gln Val Pro Val Ser Tyr Tyr Asp Ser
                85                  90                  95

Thr Tyr Leu Ser Thr Asp Asn Glu Lys Asp Asn Tyr Leu Lys Gly Val
            100                 105                 110

Thr Lys Leu Phe Glu Arg Ile Tyr Ser Thr Asp Leu Gly Arg Met Leu
        115                 120                 125

Leu Thr Ser Ile Val Arg Gly Ile Pro Phe Trp Gly Gly Ser Thr Ile
    130                 135                 140

Asp Thr Glu Leu Lys Val Ile Asp Thr Asn Cys Ile Asn Val Ile Gln
145                 150                 155                 160

Pro Asp Gly Ser Tyr Arg Ser Glu Glu Leu Asn Leu Val Ile Ile Gly
                165                 170                 175

Pro Ser Ala Asp Ile Ile Gln Phe Glu Cys Lys Ser Phe Gly His Glu
            180                 185                 190

Val Leu Asn Leu Thr Arg Asn Gly Tyr Gly Ser Thr Gln Tyr Ile Arg
        195                 200                 205

Phe Ser Pro Asp Phe Thr Phe Gly Phe Glu Glu Ser Leu Glu Val Asp
    210                 215                 220

Thr Asn Pro Leu Leu Gly Ala Gly Lys Phe Ala Thr Asp Pro Ala Val
225                 230                 235                 240

Thr Leu Ala His Glu Leu Ile His Ala Gly His Arg Leu Tyr Gly Ile
                245                 250                 255

Ala Ile Asn Pro Asn Arg Val Phe Lys Val Asn Thr Asn Ala Tyr Tyr
            260                 265                 270

Glu Met Ser Gly Leu Glu Val Ser Phe Glu Glu Leu Arg Thr Phe Gly
        275                 280                 285

Gly His Asp Ala Lys Phe Ile Asp Ser Leu Gln Glu Asn Glu Phe Arg
    290                 295                 300

Leu Tyr Tyr Tyr Asn Lys Phe Lys Asp Ile Ala Ser Thr Leu Asn Lys
305                 310                 315                 320

Ala Lys Ser Ile Val Gly Thr Thr Ala Ser Leu Gln Tyr Met Lys Asn
                325                 330                 335

Val Phe Lys Glu Lys Tyr Leu Leu Ser Glu Asp Thr Ser Gly Lys Phe
            340                 345                 350

Ser Val Asp Lys Leu Lys Phe Asp Lys Leu Tyr Lys Met Leu Thr Glu
        355                 360                 365

Ile Tyr Thr Glu Asp Asn Phe Val Lys Phe Phe Lys Val Leu Asn Arg
    370                 375                 380

Lys Thr Tyr Leu Asn Phe Asp Lys Ala Val Phe Lys Ile Asn Ile Val
```

-continued

```
385                 390                 395                 400

Pro Lys Val Asn Tyr Thr Ile Tyr Asp Gly Phe Asn Leu Arg Asn Thr
                405                 410                 415

Asn Leu Ala Ala Asn Phe Asn Gly Gln Asn Thr Glu Ile Asn Asn Met
            420                 425                 430

Asn Phe Thr Lys Leu Lys Asn Phe Thr Gly Leu Phe Glu Phe Tyr Lys
        435                 440                 445

Leu Leu Ser Val Arg Gly Ile Ile Thr Ser Lys Thr Lys Ser Leu Asp
    450                 455                 460

Lys Gly Tyr Asn Lys His His His His His His
465                 470                 475


<210> SEQ ID NO 18
<211> LENGTH: 1440
<212> TYPE: DNA
<213> ORGANISM: Artificial Sequence
<220> FEATURE:
<223> OTHER INFORMATION: gene cassette for cloning PEP1-(-M)BTX-
      L(C430S)-His

<400> SEQUENCE: 18

catatgaagg aaacttggtg ggaaacttgg tggaccgaat ggtctcaacc aaagaagaag      60

cgcaaggttc aatttgttaa taaacaattt aattataaag atccagtaaa tggtgtcgac     120

attgcttata tcaaaattcc aaatgtaggc caaatgcaac cagtaaaagc ttttaaaatt     180

cataataaaa tctgggttat tccagaacgc gatacettta ccaatccgga agaaggtgat     240

ctgaatccac caccagaagc aaaacaagtt ccagttagct attatgatag cacctatctg     300

agcaccgata atgaaaaaga taattatctg aagggcgtta ccaaactgtt tgagcgcatt     360

tatagcactg atctgggtcg catgctgctg accagcatcg tacgcggtat cccattttgg     420

ggtggtagca ccatcgatac cgaactgaaa gttattgata ctaattgtat taatgtgatc     480

caaccagatg gtagctatcg cagcgaagaa ctgaatctgg taatcatcgg tccgagcgct     540

gatattatcc agtttgaatg taaaagcttt ggtcatgaag ttctgaatct gacccgtaat     600

ggttatggca gcacccaata cattcgcttt agcccagatt ttacctttgg ttttgaggag     660

agcctggaag ttgataccaa tccgctgctg ggtgcaggca aatttgctac cgatccagca     720

gtaaccctgg cacatgaact gatacatgct ggccatcgcc tgtatggtat cgcaattaat     780

ccaaatcgcg tttttaaagt aaataccaat gcctattatg aaatgagcgg tctggaagta     840

agctttgagg aactgcgcac ctttggtggt catgatgcaa agtttatcga tagcctgcag     900

gaaaacgaat ttcgtctgta ttattataat aagtttaaag atatcgcaag caccctgaat     960

aaagctaaaa gcatcgtagg taccaccgct agcctgcagt atatgaaaaa tgtttttaaa    1020

gagaaatatc tgctgtctga agatacctct ggcaaattta gcgtagataa actgaaattt    1080

gataagctgt acaaaatgct gaccgagatt tacaccgagg ataattttgt taagtttttt    1140

aaagtactga accgcaaaac ctatctgaat tttgataaag ccgtatttaa gatcaatatc    1200

gtaccgaagg taaattacac catctatgat ggttttaatc tgcgcaatac caatctggca    1260

gcaaacttta atggtcaaaa taccgaaatt aataatatga attttaccaa actgaaaaat    1320

tttaccggtc tgtttgaatt ctataagctg ctgagcgtac gcggtatcat caccagcaaa    1380

accaaaagcc tggataaagg ctacaataag catcaccatc accatcacta ataactcgag    1440


<210> SEQ ID NO 19
<211> LENGTH: 486
```

<212> TYPE: PRT
<213> ORGANISM: Artificial Sequence
<220> FEATURE:
<223> OTHER INFORMATION: PEP1-(-M)BTX-L(C430G)-BFGFRP-His
<220> FEATURE:
<221> NAME/KEY: MISC_FEATURE
<222> LOCATION: (477)..(477)
<223> OTHER INFORMATION: X is S or T

<400> SEQUENCE: 19

```
Met Lys Glu Thr Trp Trp Glu Thr Trp Trp Thr Glu Trp Ser Gln Pro
1               5                   10                  15

Lys Lys Lys Arg Lys Val Gln Phe Val Asn Lys Gln Phe Asn Tyr Lys
            20                  25                  30

Asp Pro Val Asn Gly Val Asp Ile Ala Tyr Ile Lys Ile Pro Asn Val
        35                  40                  45

Gly Gln Met Gln Pro Val Lys Ala Phe Lys Ile His Asn Lys Ile Trp
    50                  55                  60

Val Ile Pro Glu Arg Asp Thr Phe Thr Asn Pro Glu Glu Gly Asp Leu
65                  70                  75                  80

Asn Pro Pro Pro Glu Ala Lys Gln Val Pro Val Ser Tyr Tyr Asp Ser
                85                  90                  95

Thr Tyr Leu Ser Thr Asp Asn Glu Lys Asp Asn Tyr Leu Lys Gly Val
            100                 105                 110

Thr Lys Leu Phe Glu Arg Ile Tyr Ser Thr Asp Leu Gly Arg Met Leu
        115                 120                 125

Leu Thr Ser Ile Val Arg Gly Ile Pro Phe Trp Gly Gly Ser Thr Ile
    130                 135                 140

Asp Thr Glu Leu Lys Val Ile Asp Thr Asn Cys Ile Asn Val Ile Gln
145                 150                 155                 160

Pro Asp Gly Ser Tyr Arg Ser Glu Glu Leu Asn Leu Val Ile Ile Gly
                165                 170                 175

Pro Ser Ala Asp Ile Ile Gln Phe Glu Cys Lys Ser Phe Gly His Glu
            180                 185                 190

Val Leu Asn Leu Thr Arg Asn Gly Tyr Gly Ser Thr Gln Tyr Ile Arg
        195                 200                 205

Phe Ser Pro Asp Phe Thr Phe Gly Phe Glu Glu Ser Leu Glu Val Asp
    210                 215                 220

Thr Asn Pro Leu Leu Gly Ala Gly Lys Phe Ala Thr Asp Pro Ala Val
225                 230                 235                 240

Thr Leu Ala His Glu Leu Ile His Ala Gly His Arg Leu Tyr Gly Ile
                245                 250                 255

Ala Ile Asn Pro Asn Arg Val Phe Lys Val Asn Thr Asn Ala Tyr Tyr
            260                 265                 270

Glu Met Ser Gly Leu Glu Val Ser Phe Glu Glu Leu Arg Thr Phe Gly
        275                 280                 285

Gly His Asp Ala Lys Phe Ile Asp Ser Leu Gln Glu Asn Glu Phe Arg
    290                 295                 300

Leu Tyr Tyr Tyr Asn Lys Phe Lys Asp Ile Ala Ser Thr Leu Asn Lys
305                 310                 315                 320

Ala Lys Ser Ile Val Gly Thr Thr Ala Ser Leu Gln Tyr Met Lys Asn
                325                 330                 335

Val Phe Lys Glu Lys Tyr Leu Leu Ser Glu Asp Thr Ser Gly Lys Phe
            340                 345                 350

Ser Val Asp Lys Leu Lys Phe Asp Lys Leu Tyr Lys Met Leu Thr Glu
        355                 360                 365
```

```
Ile Tyr Thr Glu Asp Asn Phe Val Lys Phe Phe Lys Val Leu Asn Arg
    370                 375                 380

Lys Thr Tyr Leu Asn Phe Asp Lys Ala Val Phe Lys Ile Asn Ile Val
385                 390                 395                 400

Pro Lys Val Asn Tyr Thr Ile Tyr Asp Gly Phe Asn Leu Arg Asn Thr
                405                 410                 415

Asn Leu Ala Ala Asn Phe Asn Gly Gln Asn Thr Glu Ile Asn Asn Met
            420                 425                 430

Asn Phe Thr Lys Leu Lys Asn Phe Thr Gly Leu Phe Glu Phe Tyr Lys
        435                 440                 445

Leu Leu Gly Val Arg Gly Ile Ile Thr Ser Lys Thr Lys Ser Leu Asp
    450                 455                 460

Lys Gly Tyr Asn Lys Thr Tyr Arg Ser Arg Lys Tyr Xaa Ser Trp Tyr
465                 470                 475                 480

His His His His His His
                485


<210> SEQ ID NO 20
<211> LENGTH: 1473
<212> TYPE: DNA
<213> ORGANISM: Artificial Sequence
<220> FEATURE:
<223> OTHER INFORMATION: gene cassette for cloning PEP1-(-M)BTX-
      L(C430G)-BFGFRP-His

<400> SEQUENCE: 20

catatgaagg aaacttggtg ggaaacttgg tggaccgaat ggtctcaacc aaagaagaag      60

cgcaaggttc aatttgttaa taaacaattt aattataaag atccagtaaa tggtgtcgac     120

attgcttata tcaaaattcc aaatgtaggc caaatgcaac cagtaaaagc ttttaaaatt     180

cataataaaa tctgggttat tccagaacgc gataccttta ccaatccgga agaaggtgat     240

ctgaatccac caccagaagc aaaacaagtt ccagttagct attatgatag cacctatctg     300

agcaccgata atgaaaaaga taattatctg aagggcgtta ccaaactgtt tgagcgcatt     360

tatagcactg atctgggtcg catgctgctg accagcatcg tacgcggtat cccattttgg     420

ggtggtagca ccatcgatac cgaactgaaa gttattgata ctaattgtat taatgtgatc     480

caaccagatg gtagctatcg cagcgaagaa ctgaatctgg taatcatcgg tccgagcgct     540

gatattatcc agtttgaatg taaaagcttt ggtcatgaag ttctgaatct gacccgtaat     600

ggttatggca gcacccaata cattcgcttt agcccagatt ttacctttgg ttttgaggag     660

agcctggaag ttgataccaa tccgctgctg ggtgcaggca aatttgctac cgatccagca     720

gtaaccctgg cacatgaact gatacatgct ggccatcgcc tgtatggtat cgcaattaat     780

ccaaatcgcg tttttaaagt aaataccaat gcctattatg aaatgagcgg tctggaagta     840

agctttgagg aactgcgcac ctttggtggt catgatgcaa agtttatcga tagcctgcag     900

gaaaacgaat ttcgtctgta ttattataat aagtttaaag atatcgcaag caccctgaat     960

aaagctaaaa gcatcgtagg taccaccgct agcctgcagt atatgaaaaa tgtttttaaa    1020

gagaaatatc tgctgtctga agatacctct ggcaaattta gcgtagataa actgaaattt    1080

gataagctgt acaaaatgct gaccgagatt tacaccgagg ataattttgt taagtttttt    1140

aaagtactga accgcaaaac ctatctgaat tttgataaag ccgtatttaa gatcaatatc    1200

gtaccgaagg taaattacac catctatgat ggttttaatc tgcgcaatac caatctggca    1260

gcaaacttta atggtcaaaa taccgaaatt aataatatga attttaccaa actgaaaaat    1320
```

```
tttaccggtc tgtttgaatt ctataagctg ctgggcgtac gcggtatcat caccagcaaa   1380

accaaaagcc tggataaagg ctacaataag acctatcgca gccgcaaata tascagctgg   1440

tatcatcacc atcaccatca ctaataactc gag                                1473


<210> SEQ ID NO 21
<211> LENGTH: 486
<212> TYPE: PRT
<213> ORGANISM: Artificial Sequence
<220> FEATURE:
<223> OTHER INFORMATION: PEP1-(-M)BTX-L(C430A)-BFGFRP-His
<220> FEATURE:
<221> NAME/KEY: MISC_FEATURE
<222> LOCATION: (477)..(477)
<223> OTHER INFORMATION: X is S or T

<400> SEQUENCE: 21

Met Lys Glu Thr Trp Trp Glu Thr Trp Trp Thr Glu Trp Ser Gln Pro
1               5                   10                  15

Lys Lys Lys Arg Lys Val Gln Phe Val Asn Lys Gln Phe Asn Tyr Lys
            20                  25                  30

Asp Pro Val Asn Gly Val Asp Ile Ala Tyr Ile Lys Ile Pro Asn Val
        35                  40                  45

Gly Gln Met Gln Pro Val Lys Ala Phe Lys Ile His Asn Lys Ile Trp
    50                  55                  60

Val Ile Pro Glu Arg Asp Thr Phe Thr Asn Pro Glu Glu Gly Asp Leu
65                  70                  75                  80

Asn Pro Pro Pro Glu Ala Lys Gln Val Pro Val Ser Tyr Tyr Asp Ser
                85                  90                  95

Thr Tyr Leu Ser Thr Asp Asn Glu Lys Asp Asn Tyr Leu Lys Gly Val
            100                 105                 110

Thr Lys Leu Phe Glu Arg Ile Tyr Ser Thr Asp Leu Gly Arg Met Leu
        115                 120                 125

Leu Thr Ser Ile Val Arg Gly Ile Pro Phe Trp Gly Gly Ser Thr Ile
    130                 135                 140

Asp Thr Glu Leu Lys Val Ile Asp Thr Asn Cys Ile Asn Val Ile Gln
145                 150                 155                 160

Pro Asp Gly Ser Tyr Arg Ser Glu Glu Leu Asn Leu Val Ile Ile Gly
                165                 170                 175

Pro Ser Ala Asp Ile Ile Gln Phe Glu Cys Lys Ser Phe Gly His Glu
            180                 185                 190

Val Leu Asn Leu Thr Arg Asn Gly Tyr Gly Ser Thr Gln Tyr Ile Arg
        195                 200                 205

Phe Ser Pro Asp Phe Thr Phe Gly Phe Glu Glu Ser Leu Glu Val Asp
    210                 215                 220

Thr Asn Pro Leu Leu Gly Ala Gly Lys Phe Ala Thr Asp Pro Ala Val
225                 230                 235                 240

Thr Leu Ala His Glu Leu Ile His Ala Gly His Arg Leu Tyr Gly Ile
                245                 250                 255

Ala Ile Asn Pro Asn Arg Val Phe Lys Val Asn Thr Asn Ala Tyr Tyr
            260                 265                 270

Glu Met Ser Gly Leu Glu Val Ser Phe Glu Glu Leu Arg Thr Phe Gly
        275                 280                 285

Gly His Asp Ala Lys Phe Ile Asp Ser Leu Gln Glu Asn Glu Phe Arg
    290                 295                 300

Leu Tyr Tyr Tyr Asn Lys Phe Lys Asp Ile Ala Ser Thr Leu Asn Lys
```

-continued

```
305                 310                 315                 320

Ala Lys Ser Ile Val Gly Thr Thr Ala Ser Leu Gln Tyr Met Lys Asn
                325                 330                 335

Val Phe Lys Glu Lys Tyr Leu Leu Ser Glu Asp Thr Ser Gly Lys Phe
            340                 345                 350

Ser Val Asp Lys Leu Lys Phe Asp Lys Leu Tyr Lys Met Leu Thr Glu
        355                 360                 365

Ile Tyr Thr Glu Asp Asn Phe Val Lys Phe Phe Lys Val Leu Asn Arg
    370                 375                 380

Lys Thr Tyr Leu Asn Phe Asp Lys Ala Val Phe Lys Ile Asn Ile Val
385                 390                 395                 400

Pro Lys Val Asn Tyr Thr Ile Tyr Asp Gly Phe Asn Leu Arg Asn Thr
                405                 410                 415

Asn Leu Ala Ala Asn Phe Asn Gly Gln Asn Thr Glu Ile Asn Asn Met
            420                 425                 430

Asn Phe Thr Lys Leu Lys Asn Phe Thr Gly Leu Phe Glu Phe Tyr Lys
        435                 440                 445

Leu Leu Ala Val Arg Gly Ile Ile Thr Ser Lys Thr Lys Ser Leu Asp
    450                 455                 460

Lys Gly Tyr Asn Lys Thr Tyr Arg Ser Arg Lys Tyr Xaa Ser Trp Tyr
465                 470                 475                 480

His His His His His His
                485

<210> SEQ ID NO 22
<211> LENGTH: 1473
<212> TYPE: DNA
<213> ORGANISM: Artificial Sequence
<220> FEATURE:
<223> OTHER INFORMATION: gene cassette for cloning PEP1-(-M)BTX-
      L(C430A)-BFGFRP-His

<400> SEQUENCE: 22
catatgaagg aaacttggtg ggaaacttgg tggaccgaat ggtctcaacc aaagaagaag     60
cgcaaggttc aatttgttaa taaacaattt aattataaag atccagtaaa tggtgtcgac    120
attgcttata tcaaaattcc aaatgtaggc caaatgcaac cagtaaaagc ttttaaaatt    180
cataataaaa tctgggttat tccagaacgc gataccttta ccaatccgga agaaggtgat    240
ctgaatccac caccagaagc aaaacaagtt ccagttagct attatgatag cacctatctg    300
agcaccgata atgaaaaaga taattatctg aagggcgtta ccaaactgtt tgagcgcatt    360
tatagcactg atctgggtcg catgctgctg accagcatcg tacgcggtat cccattttgg    420
ggtggtagca ccatcgatac cgaactgaaa gttattgata ctaattgtat taatgtgatc    480
caaccagatg gtagctatcg cagcgaagaa ctgaatctgg taatcatcgg tccgagcgct    540
gatattatcc agtttgaatg taaaagcttt ggtcatgaag ttctgaatct gacccgtaat    600
ggttatggca gcacccaata cattcgcttt agcccagatt ttacctttgg ttttgaggag    660
agcctggaag ttgataccaa tccgctgctg ggtgcaggca aatttgctac cgatccagca    720
gtaaccctgg cacatgaact gatacatgct ggccatcgcc tgtatggtat cgcaattaat    780
ccaaatcgcg tttttaaagt aaataccaat gcctattatg aaatgagcgg tctggaagta    840
agctttgagg aactgcgcac ctttggtggt catgatgcaa agtttatcga tagcctgcag    900
gaaaacgaat ttcgtctgta ttattataat aagtttaaag atatcgcaag caccctgaat    960
aaagctaaaa gcatcgtagg taccaccgct agcctgcagt atatgaaaaa tgtttttaaa   1020
```

-continued

```
gagaaatatc tgctgtctga agatacctct ggcaaattta gcgtagataa actgaaattt   1080

gataagctgt acaaaatgct gaccgagatt tacaccgagg ataattttgt taagtttttt   1140

aaagtactga accgcaaaac ctatctgaat tttgataaag ccgtatttaa gatcaatatc   1200

gtaccgaagg taaattacac catctatgat ggttttaatc tgcgcaatac caatctggca   1260

gcaaacttta atggtcaaaa taccgaaatt aataatatga attttaccaa actgaaaaat   1320

tttaccggtc tgtttgaatt ctataagctg ctggcggtac gcggtatcat caccagcaaa   1380

accaaaagcc tggataaagg ctacaataag acctatcgca gccgcaaata tascagctgg   1440

tatcatcacc atcaccatca ctaataactc gag                                 1473


<210> SEQ ID NO 23
<211> LENGTH: 486
<212> TYPE: PRT
<213> ORGANISM: Artificial Sequence
<220> FEATURE:
<223> OTHER INFORMATION: PEP1-(-M)BTX-L(C430S)-BFGFRP-His
<220> FEATURE:
<221> NAME/KEY: MISC_FEATURE
<222> LOCATION: (477)..(477)
<223> OTHER INFORMATION: X is S or T

<400> SEQUENCE: 23

Met Lys Glu Thr Trp Trp Glu Thr Trp Trp Thr Glu Trp Ser Gln Pro
1               5                   10                  15

Lys Lys Lys Arg Lys Val Gln Phe Val Asn Lys Gln Phe Asn Tyr Lys
            20                  25                  30

Asp Pro Val Asn Gly Val Asp Ile Ala Tyr Ile Lys Ile Pro Asn Val
        35                  40                  45

Gly Gln Met Gln Pro Val Lys Ala Phe Lys Ile His Asn Lys Ile Trp
    50                  55                  60

Val Ile Pro Glu Arg Asp Thr Phe Thr Asn Pro Glu Glu Gly Asp Leu
65                  70                  75                  80

Asn Pro Pro Pro Glu Ala Lys Gln Val Pro Val Ser Tyr Tyr Asp Ser
                85                  90                  95

Thr Tyr Leu Ser Thr Asp Asn Glu Lys Asp Asn Tyr Leu Lys Gly Val
            100                 105                 110

Thr Lys Leu Phe Glu Arg Ile Tyr Ser Thr Asp Leu Gly Arg Met Leu
        115                 120                 125

Leu Thr Ser Ile Val Arg Gly Ile Pro Phe Trp Gly Gly Ser Thr Ile
    130                 135                 140

Asp Thr Glu Leu Lys Val Ile Asp Thr Asn Cys Ile Asn Val Ile Gln
145                 150                 155                 160

Pro Asp Gly Ser Tyr Arg Ser Glu Glu Leu Asn Leu Val Ile Ile Gly
                165                 170                 175

Pro Ser Ala Asp Ile Ile Gln Phe Glu Cys Lys Ser Phe Gly His Glu
            180                 185                 190

Val Leu Asn Leu Thr Arg Asn Gly Tyr Gly Ser Thr Gln Tyr Ile Arg
        195                 200                 205

Phe Ser Pro Asp Phe Thr Phe Gly Phe Glu Glu Ser Leu Glu Val Asp
    210                 215                 220

Thr Asn Pro Leu Leu Gly Ala Gly Lys Phe Ala Thr Asp Pro Ala Val
225                 230                 235                 240

Thr Leu Ala His Glu Leu Ile His Ala Gly His Arg Leu Tyr Gly Ile
                245                 250                 255
```

-continued

```
Ala Ile Asn Pro Asn Arg Val Phe Lys Val Asn Thr Asn Ala Tyr Tyr
            260                 265                 270

Glu Met Ser Gly Leu Glu Val Ser Phe Glu Glu Leu Arg Thr Phe Gly
        275                 280                 285

Gly His Asp Ala Lys Phe Ile Asp Ser Leu Gln Glu Asn Glu Phe Arg
    290                 295                 300

Leu Tyr Tyr Tyr Asn Lys Phe Lys Asp Ile Ala Ser Thr Leu Asn Lys
305                 310                 315                 320

Ala Lys Ser Ile Val Gly Thr Thr Ala Ser Leu Gln Tyr Met Lys Asn
                325                 330                 335

Val Phe Lys Glu Lys Tyr Leu Leu Ser Glu Asp Thr Ser Gly Lys Phe
            340                 345                 350

Ser Val Asp Lys Leu Lys Phe Asp Lys Leu Tyr Lys Met Leu Thr Glu
        355                 360                 365

Ile Tyr Thr Glu Asp Asn Phe Val Lys Phe Phe Lys Val Leu Asn Arg
    370                 375                 380

Lys Thr Tyr Leu Asn Phe Asp Lys Ala Val Phe Lys Ile Asn Ile Val
385                 390                 395                 400

Pro Lys Val Asn Tyr Thr Ile Tyr Asp Gly Phe Asn Leu Arg Asn Thr
                405                 410                 415

Asn Leu Ala Ala Asn Phe Asn Gly Gln Asn Thr Glu Ile Asn Asn Met
            420                 425                 430

Asn Phe Thr Lys Leu Lys Asn Phe Thr Gly Leu Phe Glu Phe Tyr Lys
        435                 440                 445

Leu Leu Ser Val Arg Gly Ile Ile Thr Ser Lys Thr Lys Ser Leu Asp
    450                 455                 460

Lys Gly Tyr Asn Lys Thr Tyr Arg Ser Arg Lys Tyr Xaa Ser Trp Tyr
465                 470                 475                 480

His His His His His His
                485
```

<210> SEQ ID NO 24
<211> LENGTH: 1473
<212> TYPE: DNA
<213> ORGANISM: Artificial Sequence
<220> FEATURE:
<223> OTHER INFORMATION: gene cassette for cloning PEP1-(-M)BTX-L(C430S)-BFGFRP-His

<400> SEQUENCE: 24

```
catatgaagg aaacttggtg ggaaacttgg tggaccgaat ggtctcaacc aaagaagaag     60
cgcaaggttc aatttgttaa taaacaattt aattataaag atccagtaaa tggtgtcgac    120
attgcttata tcaaaattcc aaatgtaggc caaatgcaac cagtaaaagc ttttaaaatt    180
cataataaaa tctgggttat tccagaacgc gataccttta ccaatccgga agaaggtgat    240
ctgaatccac caccagaagc aaaacaagtt ccagttagct attatgatag cacctatctg    300
agcaccgata atgaaaaaga taattatctg aagggcgtta ccaaactgtt tgagcgcatt    360
tatagcactg atctgggtcg catgctgctg accagcatcg tacgcggtat cccattttgg    420
ggtggtagca ccatcgatac cgaactgaaa gttattgata ctaattgtat taatgtgatc    480
caaccagatg gtagctatcg cagcgaagaa ctgaatctgg taatcatcgg tccgagcgct    540
gatattatcc agtttgaatg taaaagcttt ggtcatgaag ttctgaatct gacccgtaat    600
ggttatggca gcacccaata cattcgcttt agcccagatt ttacctttgg ttttgaggag    660
agcctggaag ttgataccaa tccgctgctg ggtgcaggca aatttgctac cgatccagca    720
```

-continued

```
gtaaccctgg cacatgaact gatacatgct ggccatcgcc tgtatggtat cgcaattaat    780

ccaaatcgcg tttttaaagt aaataccaat gcctattatg aaatgagcgg tctggaagta    840

agctttgagg aactgcgcac ctttggtggt catgatgcaa agtttatcga tagcctgcag    900

gaaaacgaat ttcgtctgta ttattataat aagtttaaag atatcgcaag caccctgaat    960

aaagctaaaa gcatcgtagg taccaccgct agcctgcagt atatgaaaaa tgtttttaaa   1020

gagaaatatc tgctgtctga agatacctct ggcaaattta gcgtagataa actgaaattt   1080

gataagctgt acaaaatgct gaccgagatt tacaccgagg ataattttgt taagtttttt   1140

aaagtactga accgcaaaac ctatctgaat tttgataaag ccgtatttaa gatcaatatc   1200

gtaccgaagg taaattacac catctatgat ggttttaatc tgcgcaatac caatctggca   1260

gcaaacttta atggtcaaaa taccgaaatt aataatatga attttaccaa actgaaaaat   1320

tttaccggtc tgtttgaatt ctataagctg ctgagcgtac gcggtatcat caccagcaaa   1380

accaaaagcc tggataaagg ctacaataag acctatcgca gccgcaaata tascagctgg   1440

tatcatcacc atcaccatca ctaataactc gag                                1473
```

<210> SEQ ID NO 25
<211> LENGTH: 4
<212> TYPE: PRT
<213> ORGANISM: Artificial Sequence
<220> FEATURE:
<223> OTHER INFORMATION: Linker

<400> SEQUENCE: 25

Gly Gly Gly Gly
1

<210> SEQ ID NO 26
<211> LENGTH: 12
<212> TYPE: DNA
<213> ORGANISM: Artificial Sequence
<220> FEATURE:
<223> OTHER INFORMATION: Linker

<400> SEQUENCE: 26
ggtggtggtg gt    12

<210> SEQ ID NO 27
<211> LENGTH: 6
<212> TYPE: PRT
<213> ORGANISM: Artificial Sequence
<220> FEATURE:
<223> OTHER INFORMATION: Cleavage Peptide

<400> SEQUENCE: 27

Leu Val Pro Arg Gly Ser
1               5

<210> SEQ ID NO 28
<211> LENGTH: 18
<212> TYPE: DNA
<213> ORGANISM: Artificial Sequence
<220> FEATURE:
<223> OTHER INFORMATION: Cleavage Peptide

<400> SEQUENCE: 28
ctggtaccac gcggtagc    18

<210> SEQ ID NO 29

<211> LENGTH: 448
<212> TYPE: PRT
<213> ORGANISM: Artificial Sequence
<220> FEATURE:
<223> OTHER INFORMATION: BTX-L(C430G)

<400> SEQUENCE: 29

```
Met Gln Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380
```

-continued

```
Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Gly Val Arg
            420                 425                 430

Gly Ile Ile Thr Ser Lys Thr Lys Ser Leu Asp Lys Gly Tyr Asn Lys
        435                 440                 445
```

<210> SEQ ID NO 30
<211> LENGTH: 1344
<212> TYPE: DNA
<213> ORGANISM: Artificial Sequence
<220> FEATURE:
<223> OTHER INFORMATION: BTX-L(C430G)

<400> SEQUENCE: 30

```
atgcaatttg ttaataaaca atttaattat aaagatccag taaatggtgt cgacattgct     60
tatatcaaaa ttccaaatgt aggccaaatg caaccagtaa aagcttttaa aattcataat    120
aaaatctggg ttattccaga acgcgatacc tttaccaatc cggaagaagg tgatctgaat    180
ccaccaccag aagcaaaaca agttccagtt agctattatg atagcaccta tctgagcacc    240
gataatgaaa aagataatta tctgaagggc gttaccaaac tgtttgagcg catttatagc    300
actgatctgg gtcgcatgct gctgaccagc atcgtacgcg gtatcccatt ttggggtggt    360
agcaccatcg ataccgaact gaaagttatt gatactaatt gtattaatgt gatccaacca    420
gatggtagct atcgcagcga agaactgaat ctggtaatca tcggtccgag cgctgatatt    480
atccagtttg aatgtaaaag ctttggtcat gaagttctga atctgacccg taatggttat    540
ggcagcaccc aatacattcg ctttagccca gattttacct ttggttttga ggagagcctg    600
gaagttgata ccaatccgct gctgggtgca ggcaaatttg ctaccgatcc agcagtaacc    660
ctggcacatg aactgataca tgctggccat cgcctgtatg gtatcgcaat taatccaaat    720
cgcgttttta aagtaaatac caatgcctat tatgaaatga gcggtctgga agtaagcttt    780
gaggaactgc gcacctttgg tggtcatgat gcaaagttta tcgatagcct gcaggaaaac    840
gaatttcgtc tgtattatta taataagttt aaagatatcg caagcaccct gaataaagct    900
aaaagcatcg taggtaccac cgctagcctg cagtatatga aaaatgtttt taaagagaaa    960
tatctgctgt ctgaagatac ctctggcaaa tttagcgtag ataaactgaa atttgataag   1020
ctgtacaaaa tgctgaccga gatttacacc gaggataatt ttgttaagtt ttttaaagta   1080
ctgaaccgca aaacctatct gaattttgat aaagccgtat ttaagatcaa tatcgtaccg   1140
aaggtaaatt acaccatcta tgatggtttt aatctgcgca ataccaatct ggcagcaaac   1200
tttaatggtc aaaataccga aattaataat atgaatttta ccaaactgaa aaattttacc   1260
ggtctgtttg aattctataa gctgctgggc gtacgcggta tcatcaccag caaaaccaaa   1320
agcctggata aaggctacaa taag                                          1344
```

<210> SEQ ID NO 31
<211> LENGTH: 448
<212> TYPE: PRT
<213> ORGANISM: Artificial Sequence
<220> FEATURE:
<223> OTHER INFORMATION: BTX-L(C430A)

<400> SEQUENCE: 31

-continued

```
Met Gln Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Ala Val Arg
```

420 425 430

Gly Ile Ile Thr Ser Lys Thr Lys Ser Leu Asp Lys Gly Tyr Asn Lys
435 440 445

<210> SEQ ID NO 32
<211> LENGTH: 1344
<212> TYPE: DNA
<213> ORGANISM: Artificial Sequence
<220> FEATURE:
<223> OTHER INFORMATION: BTX-L(C430A)

<400> SEQUENCE: 32
atgcaatttg ttaataaaca atttaattat aaagatccag taaatggtgt cgacattgct 60
tatatcaaaa ttccaaatgt aggccaaatg caaccagtaa aagcttttaa aattcataat 120
aaaatctggg ttattccaga acgcgatacc tttaccaatc cggaagaagg tgatctgaat 180
ccaccaccag aagcaaaaca agttccagtt agctattatg atagcaccta tctgagcacc 240
gataatgaaa aagataatta tctgaagggc gttaccaaac tgtttgagcg catttatagc 300
actgatctgg gtcgcatgct gctgaccagc atcgtacgcg gtatcccatt ttggggtggt 360
agcaccatcg ataccgaact gaaagttatt gatactaatt gtattaatgt gatccaacca 420
gatggtagct atcgcagcga agaactgaat ctggtaatca tcggtccgag cgctgatatt 480
atccagtttg aatgtaaaag ctttggtcat gaagttctga atctgacccg taatggttat 540
ggcagcaccc aatacattcg ctttagccca gattttacct ttggttttga ggagagcctg 600
gaagttgata ccaatccgct gctgggtgca ggcaaatttg ctaccgatcc agcagtaacc 660
ctggcacatg aactgataca tgctggccat cgcctgtatg gtatcgcaat taatccaaat 720
cgcgttttta aagtaaatac caatgcctat tatgaaatga gcggtctgga agtaagcttt 780
gaggaactgc gcacctttgg tggtcatgat gcaaagttta tcgatagcct gcaggaaaac 840
gaatttcgtc tgtattatta taataagttt aaagatatcg caagcaccct gaataaagct 900
aaaagcatcg taggtaccac cgctagcctg cagtatatga aaaatgtttt taaagagaaa 960
tatctgctgt ctgaagatac ctctggcaaa tttagcgtag ataaactgaa atttgataag 1020
ctgtacaaaa tgctgaccga gatttacacc gaggataatt ttgttaagtt ttttaaagta 1080
ctgaaccgca aaacctatct gaattttgat aaagccgtat ttaagatcaa tatcgtaccg 1140
aaggtaaatt acaccatcta tgatggtttt aatctgcgca ataccaatct ggcagcaaac 1200
tttaatggtc aaaataccga aattaataat atgaatttta ccaaactgaa aaattttacc 1260
ggtctgtttg aattctataa gctgctggcg gtacgcggta tcatcaccag caaaaccaaa 1320
agcctggata aaggctacaa taag 1344

<210> SEQ ID NO 33
<211> LENGTH: 448
<212> TYPE: PRT
<213> ORGANISM: Artificial Sequence
<220> FEATURE:
<223> OTHER INFORMATION: BTX-L(C430S)

<400> SEQUENCE: 33

Met Gln Phe Val Asn Lys Gln Phe Asn Tyr Lys Asp Pro Val Asn Gly
1 5 10 15

Val Asp Ile Ala Tyr Ile Lys Ile Pro Asn Val Gly Gln Met Gln Pro
20 25 30

Val Lys Ala Phe Lys Ile His Asn Lys Ile Trp Val Ile Pro Glu Arg
35 40 45

-continued

```
Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Ser Val Arg
            420                 425                 430

Gly Ile Ile Thr Ser Lys Thr Lys Ser Leu Asp Lys Gly Tyr Asn Lys
        435                 440                 445
```

<210> SEQ ID NO 34
<211> LENGTH: 1344

<212> TYPE: DNA
<213> ORGANISM: Artificial Sequence
<220> FEATURE:
<223> OTHER INFORMATION: BTX-L(C430S)

<400> SEQUENCE: 34
atgcaatttg ttaataaaca atttaattat aaagatccag taaatggtgt cgacattgct 60
tatatcaaaa ttccaaatgt aggccaaatg caaccagtaa aagcttttaa aattcataat 120
aaaatctggg ttattccaga acgcgatacc tttaccaatc cggaagaagg tgatctgaat 180
ccaccaccag aagcaaaaca agttccagtt agctattatg atagcaccta tctgagcacc 240
gataatgaaa aagataatta tctgaagggc gttaccaaac tgtttgagcg catttatagc 300
actgatctgg gtcgcatgct gctgaccagc atcgtacgcg gtatcccatt ttggggtggt 360
agcaccatcg ataccgaact gaaagttatt gatactaatt gtattaatgt gatccaacca 420
gatggtagct atcgcagcga agaactgaat ctggtaatca tcggtccgag cgctgatatt 480
atccagtttg aatgtaaaag ctttggtcat gaagttctga atctgacccg taatggttat 540
ggcagcaccc aatacattcg ctttagccca gattttacct ttggttttga ggagagcctg 600
gaagttgata ccaatccgct gctgggtgca ggcaaatttg ctaccgatcc agcagtaacc 660
ctggcacatg aactgataca tgctggccat cgcctgtatg gtatcgcaat taatccaaat 720
cgcgttttta aagtaaatac caatgcctat tatgaaatga gcggtctgga agtaagcttt 780
gaggaactgc gcacctttgg tggtcatgat gcaaagttta tcgatagcct gcaggaaaac 840
gaatttcgtc tgtattatta taataagttt aaagatatcg caagcaccct gaataaagct 900
aaaagcatcg taggtaccac cgctagcctg cagtatatga aaaatgtttt taaagagaaa 960
tatctgctgt ctgaagatac ctctggcaaa tttagcgtag ataaactgaa atttgataag 1020
ctgtacaaaa tgctgaccga gatttacacc gaggataatt ttgttaagtt ttttaaagta 1080
ctgaaccgca aaacctatct gaattttgat aaagccgtat ttaagatcaa tatcgtaccg 1140
aaggtaaatt acaccatcta tgatggtttt aatctgcgca ataccaatct ggcagcaaac 1200
tttaatggtc aaaataccga aattaataat atgaatttta ccaaactgaa aaattttacc 1260
ggtctgtttg aattctataa gctgctgagc gtacgcggta tcatcaccag caaaaccaaa 1320
agcctggata aaggctacaa taag 1344

<210> SEQ ID NO 35
<211> LENGTH: 105
<212> TYPE: DNA
<213> ORGANISM: Artificial Sequence
<220> FEATURE:
<223> OTHER INFORMATION: gene cassette for cloning C430G

<400> SEQUENCE: 35
gaattctata agctgctggg cgtacgcggt atcatcacca gcaaaaccaa aagcctggat 60
aaaggctaca ataagcatca ccatcaccat cactaataac tcgag 105

<210> SEQ ID NO 36
<211> LENGTH: 105
<212> TYPE: DNA
<213> ORGANISM: Artificial Sequence
<220> FEATURE:
<223> OTHER INFORMATION: gene cassette for cloining C430A

<400> SEQUENCE: 36
gaattctata agctgctggc ggtacgcggt atcatcacca gcaaaaccaa aagcctggat 60
aaaggctaca ataagcatca ccatcaccat cactaataac tcgag 105

<210> SEQ ID NO 37
<211> LENGTH: 105
<212> TYPE: DNA
<213> ORGANISM: Artificial Sequence
<220> FEATURE:
<223> OTHER INFORMATION: gene cassette for cloining C430S

<400> SEQUENCE: 37
gaattctata agctgctgag cgtacgcggt atcatcacca gcaaaaccaa aagcctggat 60
aaaggctaca ataagcatca ccatcaccat cactaataac tcgag 105

<210> SEQ ID NO 38
<211> LENGTH: 138
<212> TYPE: DNA
<213> ORGANISM: Artificial Sequence
<220> FEATURE:
<223> OTHER INFORMATION: gene cassette for cloining C430G-BFGRP

<400> SEQUENCE: 38
gaattctata agctgctggg cgtacgcggt atcatcacca gcaaaaccaa aagcctggat 60
aaaggctaca ataagaccta tcgcagccgc aaatatasca gctggtatca tcaccatcac 120
catcactaat aactcgag 138

<210> SEQ ID NO 39
<211> LENGTH: 138
<212> TYPE: DNA
<213> ORGANISM: Artificial Sequence
<220> FEATURE:
<223> OTHER INFORMATION: gene cassette for cloning C430A-BFGRP

<400> SEQUENCE: 39
gaattctata agctgctggc ggtacgcggt atcatcacca gcaaaaccaa aagcctggat 60
aaaggctaca ataagaccta tcgcagccgc aaatatasca gctggtatca tcaccatcac 120
catcactaat aactcgag 138

<210> SEQ ID NO 40
<211> LENGTH: 138
<212> TYPE: DNA
<213> ORGANISM: Artificial Sequence
<220> FEATURE:
<223> OTHER INFORMATION: gene cassette for cloning C430S-BFGRP

<400> SEQUENCE: 40
gaattctata agctgctgag cgtacgcggt atcatcacca gcaaaaccaa aagcctggat 60
aaaggctaca ataagaccta tcgcagccgc aaatatasca gctggtatca tcaccatcac 120
catcactaat aactcgag 138

<210> SEQ ID NO 41
<211> LENGTH: 123
<212> TYPE: DNA
<213> ORGANISM: Artificial Sequence
<220> FEATURE:
<223> OTHER INFORMATION: gene cassette for cloning belt'

<400> SEQUENCE: 41
gaattctata agctgctgtg tgtacgcggt atcatcacca gcaaaaccaa aagcctggat 60
aaaggctaca ataaggcgct gaacgatctg tgccatcacc atcaccatca ctaataactc 120
gag 123

<210> SEQ ID NO 42
<211> LENGTH: 453
<212> TYPE: PRT
<213> ORGANISM: Artificial Sequence
<220> FEATURE:
<223> OTHER INFORMATION: His-SNAP25-ANNEXIN V

<400> SEQUENCE: 42

Met Gly Gly Ser His His His His His His Glu Asn Leu Tyr Phe Gln
1 5 10 15

Gly Ser Gly Gly Asn Lys Leu Lys Ser Ser Asp Ala Tyr Lys Lys Ala
20 25 30

Trp Gly Asn Asn Gln Asp Gly Val Val Ala Ser Gln Pro Ala Arg Val
35 40 45

Val Asp Glu Arg Glu Gln Met Ala Ile Ser Gly Gly Phe Ile Arg Arg
50 55 60

Val Thr Asn Asp Ala Arg Glu Asn Glu Met Asp Glu Asn Leu Glu Gln
65 70 75 80

Val Ser Gly Ile Ile Gly Asn Leu Arg His Met Ala Leu Asp Met Gly
85 90 95

Asn Glu Ile Asp Thr Gln Asn Arg Gln Ile Asp Arg Ile Met Glu Lys
100 105 110

Ala Asp Ser Asn Lys Thr Arg Ile Asp Glu Ala Asn Gln Arg Ala Thr
115 120 125

Lys Met Leu Gly Ser Gly Ala Gln Val Leu Arg Gly Thr Val Thr Asp
130 135 140

Phe Pro Gly Phe Asp Glu Arg Ala Asp Ala Glu Thr Leu Arg Lys Ala
145 150 155 160

Met Lys Gly Leu Gly Thr Asp Glu Glu Ser Ile Leu Thr Leu Leu Thr
165 170 175

Ser Arg Ser Asn Ala Gln Arg Gln Glu Ile Ser Ala Ala Phe Lys Thr
180 185 190

Leu Phe Gly Arg Asp Leu Leu Asp Asp Leu Lys Ser Glu Leu Thr Gly
195 200 205

Lys Phe Glu Lys Leu Ile Val Ala Leu Met Lys Pro Ser Arg Leu Tyr
210 215 220

Asp Ala Tyr Glu Leu Lys His Ala Leu Lys Gly Ala Gly Thr Asn Glu
225 230 235 240

Lys Val Leu Thr Glu Ile Ile Ala Ser Arg Thr Pro Glu Glu Leu Arg
245 250 255

Ala Ile Lys Gln Val Tyr Glu Glu Glu Tyr Gly Ser Ser Leu Glu Asp
260 265 270

Asp Val Val Gly Asp Thr Ser Gly Tyr Tyr Gln Arg Met Leu Val Val
275 280 285

Leu Leu Gln Ala Asn Arg Asp Pro Asp Ala Gly Ile Asp Glu Ala Gln
290 295 300

Val Glu Gln Asp Ala Gln Ala Leu Phe Gln Ala Gly Glu Leu Lys Trp
305 310 315 320

Gly Thr Asp Glu Glu Lys Phe Ile Thr Ile Phe Gly Thr Arg Ser Val
325 330 335

Ser His Leu Arg Lys Val Phe Asp Lys Tyr Met Thr Ile Ser Gly Phe
340 345 350

Gln Ile Glu Glu Thr Ile Asp Arg Glu Thr Ser Gly Asn Leu Glu Gln
355 360 365

```
Leu Leu Leu Ala Val Val Lys Ser Ile Arg Ser Ile Pro Ala Tyr Leu
    370                 375                 380

Ala Glu Thr Leu Tyr Tyr Ala Met Lys Gly Ala Gly Thr Asp Asp His
385                 390                 395                 400

Thr Leu Ile Arg Val Met Val Ser Arg Ser Glu Ile Asp Leu Phe Asn
                405                 410                 415

Ile Arg Lys Glu Phe Arg Lys Asn Phe Ala Thr Ser Leu Tyr Ser Met
            420                 425                 430

Ile Lys Gly Asp Thr Ser Gly Asp Tyr Lys Lys Ala Leu Leu Leu Leu
        435                 440                 445

Cys Gly Glu Asp Asp
    450


<210> SEQ ID NO 43
<211> LENGTH: 1371
<212> TYPE: DNA
<213> ORGANISM: Artificial Sequence
<220> FEATURE:
<223> OTHER INFORMATION: His-SNAP25-ANNEXIN V

<400> SEQUENCE: 43

catatgggcg gcagccatca tcatcatcat catgaaaacc tgtattttca gggctctggc      60

ggcaacaagc tgaaatctag cgatgcttac aaaaaagcct ggggcaataa tcaggacggc     120

gtggtggcca gccagcctgc tcgtgtagtg gacgaacgtg agcagatggc catcagcggc     180

ggcttcatcc gtcgtgtaac caatgatgcc cgtgaaaatg aaatggatga aaacctggag     240

caggtgagcg gcatcatcgg caacctgcgt cacatggccc tggatatggg caatgagatc     300

gatacccaga atcgtcagat cgaccgtatc atggagaagg ctgattccaa caaaacccgt     360

atcgatgagg ccaaccaacg tgcaaccaag atgctgggca gcggcgcaca ggttctgcgt     420

ggcactgtga ccgacttccc tggctttgat gagcgtgctg atgcagaaac cctgcgtaag     480

gctatgaaag gcctgggcac cgatgaggag agcatcctga ccctgctgac ctcccgtagc     540

aatgctcagc gtcaggaaat ctctgcagct tttaagaccc tgtttggccg tgatctgctg     600

gatgacctga aatccgaact gaccggcaaa tttgaaaaac tgatcgtggc tctgatgaaa     660

ccttctcgtc tgtatgatgc ttatgaactg aaacatgccc tgaagggcgc tggcaccaat     720

gaaaaagtac tgaccgaaat cattgcttct cgtacccctg aagaactgcg tgccatcaaa     780

caagtttatg aagaagaata tggctctagc ctggaagatg acgtggtggg cgacacttct     840

ggctactacc agcgtatgct ggtggttctg ctgcaggcta accgtgaccc tgatgctggc     900

atcgatgaag ctcaagttga acaagatgct caggctctgt ttcaggctgg cgaactgaaa     960

tggggcaccg atgaagaaaa gtttatcacc atctttggca cccgtagcgt gtctcatctg    1020

agaaaggtgt ttgacaagta catgaccatc tctggctttc aaatcgagga aaccatcgac    1080

cgtgagactt ctggcaatct ggagcaactg ctgctggctg ttgtgaaatc tatccgtagc    1140

atccctgcct acctggcaga gaccctgtat tatgctatga agggcgctgg caccgatgat    1200

cataccctga tccgtgtcat ggtttcccgt agcgagatcg atctgtttaa catccgtaag    1260

gagtttcgta agaattttgc cacctctctg tattccatga tcaagggcga tacctctggc    1320

gactataaga aagctctgct gctgctgtgt ggcgaagatg actaactcga g             1371


<210> SEQ ID NO 44
<211> LENGTH: 567
<212> TYPE: PRT
```

<213> ORGANISM: Artificial Sequence
<220> FEATURE:
<223> OTHER INFORMATION: SMF-(-M)BTX-L-PEP1-TEV-His

<400> SEQUENCE: 44

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Gln Phe Val Asn Lys Gln Phe Asn Tyr Lys Asp
                85                  90                  95

Pro Val Asn Gly Val Asp Ile Ala Tyr Ile Lys Ile Pro Asn Val Gly
            100                 105                 110

Gln Met Gln Pro Val Lys Ala Phe Lys Ile His Asn Lys Ile Trp Val
        115                 120                 125

Ile Pro Glu Arg Asp Thr Phe Thr Asn Pro Glu Glu Gly Asp Leu Asn
    130                 135                 140

Pro Pro Pro Glu Ala Lys Gln Val Pro Val Ser Tyr Tyr Asp Ser Thr
145                 150                 155                 160

Tyr Leu Ser Thr Asp Asn Glu Lys Asp Asn Tyr Leu Lys Gly Val Thr
                165                 170                 175

Lys Leu Phe Glu Arg Ile Tyr Ser Thr Asp Leu Gly Arg Met Leu Leu
            180                 185                 190

Thr Ser Ile Val Arg Gly Ile Pro Phe Trp Gly Gly Ser Thr Ile Asp
        195                 200                 205

Thr Glu Leu Lys Val Ile Asp Thr Asn Cys Ile Asn Val Ile Gln Pro
    210                 215                 220

Asp Gly Ser Tyr Arg Ser Glu Glu Leu Asn Leu Val Ile Ile Gly Pro
225                 230                 235                 240

Ser Ala Asp Ile Ile Gln Phe Glu Cys Lys Ser Phe Gly His Glu Val
                245                 250                 255

Leu Asn Leu Thr Arg Asn Gly Tyr Gly Ser Thr Gln Tyr Ile Arg Phe
            260                 265                 270

Ser Pro Asp Phe Thr Phe Gly Phe Glu Glu Ser Leu Glu Val Asp Thr
        275                 280                 285

Asn Pro Leu Leu Gly Ala Gly Lys Phe Ala Thr Asp Pro Ala Val Thr
    290                 295                 300

Leu Ala His Glu Leu Ile His Ala Gly His Arg Leu Tyr Gly Ile Ala
305                 310                 315                 320

Ile Asn Pro Asn Arg Val Phe Lys Val Asn Thr Asn Ala Tyr Tyr Glu
                325                 330                 335

Met Ser Gly Leu Glu Val Ser Phe Glu Glu Leu Arg Thr Phe Gly Gly
            340                 345                 350

His Asp Ala Lys Phe Ile Asp Ser Leu Gln Glu Asn Glu Phe Arg Leu
        355                 360                 365

Tyr Tyr Tyr Asn Lys Phe Lys Asp Ile Ala Ser Thr Leu Asn Lys Ala
    370                 375                 380

Lys Ser Ile Val Gly Thr Thr Ala Ser Leu Gln Tyr Met Lys Asn Val
```

-continued

```
385                 390                 395                 400

Phe Lys Glu Lys Tyr Leu Leu Ser Glu Asp Thr Ser Gly Lys Phe Ser
                405                 410                 415

Val Asp Lys Leu Lys Phe Asp Lys Leu Tyr Lys Met Leu Thr Glu Ile
            420                 425                 430

Tyr Thr Glu Asp Asn Phe Val Lys Phe Phe Lys Val Leu Asn Arg Lys
        435                 440                 445

Thr Tyr Leu Asn Phe Asp Lys Ala Val Phe Lys Ile Asn Ile Val Pro
    450                 455                 460

Lys Val Asn Tyr Thr Ile Tyr Asp Gly Phe Asn Leu Arg Asn Thr Asn
465                 470                 475                 480

Leu Ala Ala Asn Phe Asn Gly Gln Asn Thr Glu Ile Asn Asn Met Asn
                485                 490                 495

Phe Thr Lys Leu Lys Asn Phe Thr Gly Leu Phe Glu Phe Tyr Lys Leu
            500                 505                 510

Leu Cys Val Arg Gly Ile Ile Thr Ser Lys Thr Lys Ser Leu Asp Lys
        515                 520                 525

Gly Tyr Asn Lys Lys Glu Thr Trp Trp Glu Thr Trp Trp Thr Glu Trp
    530                 535                 540

Ser Gln Pro Lys Lys Lys Arg Lys Val Glu Asn Leu Tyr Phe Gln Ser
545                 550                 555                 560

Asn His His His His His His
                565


<210> SEQ ID NO 45
<211> LENGTH: 1704
<212> TYPE: DNA
<213> ORGANISM: Artificial Sequence
<220> FEATURE:
<223> OTHER INFORMATION: SMF-(-M)BTX-L-PEP1-TEV-His

<400> SEQUENCE: 45

atgagatttc catctatttt tactgcagtt ttgtttgcag catcttctgc attggcagca     60

ccagttaaca ctactactga agatgaaact gcacaaattc cagcagaagc agttattggt    120

tactctgatt tggaaggtga ttttgatgtt gctgttttgc cattttctaa ctctactaat    180

aacggtttgt tgtttattaa tactactatt gcatctattg cagcaaagga agaaggtgtt    240

tctttggaaa aaagacagtt tgttaacaag caattcaatt acaaagatcc agttaatggt    300

gttgacattg cttatattaa aattccaaac gttggtcaga tgcagccagt taaagctttc    360

aagatccata acaaaatttg ggttatccca gagagagaca ctttcactaa tccagaggaa    420

ggtgatttga acccaccacc agaagcaaaa caggttccag ttagttatta tgacagtact    480

tatctttcca ctgataacga gaaagataac tatttgaaag gtgttactaa gctgtttgaa    540

agaatttaca gtactgactt gggaagaatg ttgctgactt caattgttag aggaattcca    600

ttttggggtg gatctactat tgacactgaa ttgaaagtta tcgatactaa ttgtattaac    660

gttatccaac cagacggttc ctacagatct gaggagctta acttggttat tattggtcca    720

tccgctgaca ttattcaatt tgagtgtaag tcattcggac atgaggtttt gaacctgact    780

cgtaatggtt atggttccac tcaatatatt agattttccc cagattttac ttttggtttc    840

gaggaaagtt tggaggttga tactaaccca ttgctgggtg caggtaagtt tgctactgat    900

ccagcagtta ctcttgctca tgagctgatc catgcaggtc atagattgta tggtattgca    960

attaatccaa accgtgtttt taaagttaat actaatgctt attatgaaat gtcaggtttg   1020
```

-continued

```
gaagtttctt tcgaagagtt gagaactttc ggaggacatg atgctaagtt cattgactct   1080

ttgcaggaaa acgagttccg tctgtactac tataacaagt tcaaggacat cgcatctact   1140

ttgaacaagg caaagtcaat tgttggtact actgcttcac tgcaatatat gaagaacgtt   1200

ttcaaggaga agtacttgtt gtccgaggat actagtggta aattctctgt tgacaaattg   1260

aagttcgaca aattgtacaa aatgctgact gagatctata ctgaagacaa cttcgttaag   1320

tttttaaag ttctgaacag aaagacttat ttgaactttg ataaggctgt ttttaagatt   1380

aacattgttc caaaggttaa ctatactatt tatgacggtt tcaatctgag aaacactaat   1440

cttgcagcta atttcaatgg tcagaatact gagattaata atatgaactt cactaagttg   1500

aaaaatttta ctggtttgtt tgaattttac aagttgttgt gtgttcgtgg aattattact   1560

tccaagacta aatctttgga taagggttac aacaaaaagg aaacttggtg ggaaacttgg   1620

tggactgaat ggtctcaacc aaagaagaag agaaaggttg agaacctgta cttccaatcc   1680

aatcatcacc atcaccatca ctaa                                           1704
```

<210> SEQ ID NO 46
<211> LENGTH: 85
<212> TYPE: PRT
<213> ORGANISM: Artificial Sequence
<220> FEATURE:
<223> OTHER INFORMATION: SMF

<400> SEQUENCE: 46

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg
                85
```

<210> SEQ ID NO 47
<211> LENGTH: 255
<212> TYPE: DNA
<213> ORGANISM: Artificial Sequence
<220> FEATURE:
<223> OTHER INFORMATION: SMF

<400> SEQUENCE: 47

```
atgagatttc catctatttt tactgcagtt ttgtttgcag catcttctgc attggcagca     60

ccagttaaca ctactactga agatgaaact gcacaaattc cagcagaagc agttattggt    120

tactctgatt tggaaggtga ttttgatgtt gctgttttgc cattttctaa ctctactaat    180

aacggtttgt tgtttattaa tactactatt gcatctattg cagcaaagga agaaggtgtt    240

tctttggaaa aaaga                                                     255
```

<210> SEQ ID NO 48
<211> LENGTH: 8
<212> TYPE: PRT
<213> ORGANISM: Artificial Sequence
<220> FEATURE:
<223> OTHER INFORMATION: TEV

<400> SEQUENCE: 48

Glu Asn Leu Tyr Phe Gln Ser Asn
1 5

<210> SEQ ID NO 49
<211> LENGTH: 24
<212> TYPE: DNA
<213> ORGANISM: Artificial Sequence
<220> FEATURE:
<223> OTHER INFORMATION: TEV

<400> SEQUENCE: 49
gagaacctgt acttccaatc caat 24

<210> SEQ ID NO 50
<211> LENGTH: 5
<212> TYPE: PRT
<213> ORGANISM: Artificial Sequence
<220> FEATURE:
<223> OTHER INFORMATION: Protease Cleavage Site

<400> SEQUENCE: 50

Asp Asp Asp Asp Lys
1 5

<210> SEQ ID NO 51
<211> LENGTH: 4
<212> TYPE: PRT
<213> ORGANISM: Artificial Sequence
<220> FEATURE:
<223> OTHER INFORMATION: Protease Cleavage Site

<400> SEQUENCE: 51

Ile Glu Gly Arg
1

<210> SEQ ID NO 52
<211> LENGTH: 4
<212> TYPE: PRT
<213> ORGANISM: Artificial Sequence
<220> FEATURE:
<223> OTHER INFORMATION: Protease Cleavage Site

<400> SEQUENCE: 52

Ile Asp Gly Arg
1

<210> SEQ ID NO 53
<211> LENGTH: 7
<212> TYPE: PRT
<213> ORGANISM: Artificial Sequence
<220> FEATURE:
<223> OTHER INFORMATION: Protease Cleavage Site

<400> SEQUENCE: 53

Glu Asn Leu Tyr Phe Gln Gly
1 5

<210> SEQ ID NO 54
<211> LENGTH: 6
<212> TYPE: PRT
<213> ORGANISM: Artificial Sequence
<220> FEATURE:
<223> OTHER INFORMATION: Protease Cleavage Site

<400> SEQUENCE: 54

```
Leu Val Pro Arg Gly Ser
1               5


<210> SEQ ID NO 55
<211> LENGTH: 8
<212> TYPE: PRT
<213> ORGANISM: Artificial Sequence
<220> FEATURE:
<223> OTHER INFORMATION: Protease Cleavage Site

<400> SEQUENCE: 55

Leu Glu Val Leu Phe Gln Gly Pro
1               5


<210> SEQ ID NO 56
<211> LENGTH: 16
<212> TYPE: PRT
<213> ORGANISM: Artificial Sequence
<220> FEATURE:
<223> OTHER INFORMATION: Cell Penetrating Peptide(Protein-derived
      Penetration)

<400> SEQUENCE: 56

Arg Gln Ile Lys Ile Trp Phe Gln Asn Arg Arg Met Lys Trp Lys Lys
1               5                   10                  15


<210> SEQ ID NO 57
<211> LENGTH: 13
<212> TYPE: PRT
<213> ORGANISM: Artificial Sequence
<220> FEATURE:
<223> OTHER INFORMATION: Cell Penetrating Peptide(Tat peptide)

<400> SEQUENCE: 57

Gly Arg Lys Lys Arg Arg Gln Arg Arg Arg Pro Pro Gln
1               5                   10


<210> SEQ ID NO 58
<211> LENGTH: 16
<212> TYPE: PRT
<213> ORGANISM: Artificial Sequence
<220> FEATURE:
<223> OTHER INFORMATION: Cell Penetrating Peptide(pVEC)

<400> SEQUENCE: 58

Leu Leu Ile Ile Leu Arg Arg Arg Ile Arg Lys Gln Ala His Ala His
1               5                   10                  15


<210> SEQ ID NO 59
<211> LENGTH: 27
<212> TYPE: PRT
<213> ORGANISM: Artificial Sequence
<220> FEATURE:
<223> OTHER INFORMATION: Cell Penetrating Peptide(Transportan)

<400> SEQUENCE: 59

Gly Trp Thr Leu Asn Ser Ala Gly Tyr Leu Leu Gly Lys Ile Asn Leu
1               5                   10                  15
```

-continued

```
Lys Ala Leu Ala Ala Leu Ala Lys Lys Ile Leu
            20                  25


<210> SEQ ID NO 60
<211> LENGTH: 27
<212> TYPE: PRT
<213> ORGANISM: Artificial Sequence
<220> FEATURE:
<223> OTHER INFORMATION: Cell Penetrating Peptide(MPG)

<400> SEQUENCE: 60

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25


<210> SEQ ID NO 61
<211> LENGTH: 21
<212> TYPE: PRT
<213> ORGANISM: Artificial Sequence
<220> FEATURE:
<223> OTHER INFORMATION: Cell Penetrating Peptide(Pep1)

<400> SEQUENCE: 61

Lys Glu Thr Trp Trp Glu Thr Trp Trp Thr Glu Trp Ser Gln Pro Lys
1               5                   10                  15

Lys Lys Arg Lys Val
            20


<210> SEQ ID NO 62
<211> LENGTH: 18
<212> TYPE: PRT
<213> ORGANISM: Artificial Sequence
<220> FEATURE:
<223> OTHER INFORMATION: Cell Penetrating Peptide(MAP)

<400> SEQUENCE: 62

Lys Leu Ala Leu Lys Leu Ala Leu Lys Ala Leu Lys Ala Ala Leu Lys
1               5                   10                  15

Leu Ala


<210> SEQ ID NO 63
<211> LENGTH: 9
<212> TYPE: PRT
<213> ORGANISM: Artificial Sequence
<220> FEATURE:
<223> OTHER INFORMATION: Cell Penetrating Peptide(R6W3)

<400> SEQUENCE: 63

Arg Arg Trp Trp Arg Arg Trp Arg Arg
1               5
```